(12) United States Patent
Nemecek et al.

(10) Patent No.: US 8,110,571 B2
(45) Date of Patent: Feb. 7, 2012

(54) BENZIMIDAZOLE AND BENZOTHIAZOLE DERIVATIVES, METHOD FOR PREPARING SAME, USE THEREOF AS DRUGS, PHARMACEUTICAL COMPOSITIONS AND NOVEL USE ESPECIALLY AS C-MET INHIBITORS

(75) Inventors: Conception Nemecek, Thiais (FR); Francois Clerc, Antony (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 12/054,719

(22) Filed: Mar. 25, 2008

(65) Prior Publication Data

US 2008/0194555 A1 Aug. 14, 2008

Related U.S. Application Data

(63) Continuation of application No. PCT/FR2006/002183, filed on Sep. 25, 2006.

(30) Foreign Application Priority Data

Sep. 27, 2005 (FR) .................................. 05 09850

(51) Int. Cl.
*A01N 43/52* (2006.01)
*A61K 31/415* (2006.01)
(52) U.S. Cl. ..................... 514/233.8; 514/395; 544/135
(58) Field of Classification Search .......................... None
See application file for complete search history.

(56) References Cited

U.S. PATENT DOCUMENTS

| 4,639,463 | A  | * | 1/1987  | Rosner et al. ............... 514/395 |
| 6,693,125 | B2 | * | 2/2004  | Borisy et al. ............... 514/388 |
| 7,632,952 | B2 |   | 12/2009 | Deprets et al. |
| 2007/0093488 | A1 |   | 4/2007 | Deprets et al. |

FOREIGN PATENT DOCUMENTS

| DE | 25 41 752       | 3/1977  |
| EP | 0 115 039       | 8/1984  |
| EP | 1298125         | * 9/2001 |
| FR | 2868421         | * 7/2005 |
| WO | WO 00/41669     | 7/2000  |
| WO | WO 02/076454    | 10/2002 |
| WO | WO 03/028721    | 4/2003  |
| WO | WO 2005/097787  | 10/2005 |

OTHER PUBLICATIONS

Jordan, V.C. Nature Reviews: Drug Discovery, 2, 2003, p. 205.*
Dorwald F. Zaragoza. Side Reviews in Organic Synthesis: A guide to successful synthesis design, Weinheim: Wiley-VCH, Verlag, GMBH & Co. KGaA, 2005, Preface.*
Wolff et al. Burger's Medicinal Chemistry and Drug Discovery—Fifth Edition, New York: John Wiley & Songs, 1996, vol. 1, pp. 975-976.*
Vippagunta et al. Advanced Drug Delivery Reviews, 48, 2001, p. 18.*
Remington's Pharmaceutical Sciences, pp. 420-425, 1980.*
Kassai et al. Activity of luxabendazole against liver flukes, gastrointestinal roundworms, and lungworms in naturally infected sheep. Parasitol. Res. 1988. 75: 14-18.*
Bach et al, Synthesis of Ansa-Bridged Macrocyclic Lactams Related to the Antitumor Antibiotic Geldanamycin by Ring Closing Metathesis, Synlett 2002, No. 8, 1302-1304.
Bischoff, J. R., et. al., A homologue of Drosophila aurora kinase is oncogenic and amplified in human colorectal cancers, EMBO Journal, vol. 17, No. 11, 1998, pp. 3052-3065 (1998).
Davies, T. G., et. al., Inhibitor Binding to Active and Inactive CDK2: The Crystal Structure of CDK2-Cyclin A/Indirubin-5-Sulphonate, Structure, vol. 9, pp. 389-397, (2001).
Folkman, J., et. al., Angiogenesis in cancer, vascular, rheumatoid and other disease, Nature Med., vol. 1, (1995), pp. 27-31.
Lee, C.-G., et. al., Anti-Vascular Endothelial Growth Factor Treatment Augments Tumor Radiation Response under Normoxic or Hypoxic Conditions, Cancer Research, (2000) vol. 60 pp. 5565-5570.
Merenmies, J., et. al., Receptor Tyrosine Kinase Signaling in Vascular Development, Cell Growth & Differentiation, vol. 8, (1997), pp. 3-10.
Millauer, B., et. al., Dominant-Negative Inhibition of Flk-1 Suppresses the Growth of Many Tumor Types in Vivo, Cancer Research, (1998) vol. 56, pp. 1615-1620.
Strawn, L.M., et. al., Flk-1 as a Target for Tumor Growth Inhibition, Cancer Research, vol. 56, (1996), pp. 3540-3545.
Toogood, P. L., et. al., Cyclin-Dependent Kinase Inhibitors for Treating Cancer, Med. Res. Rev., vol. 21, No. 6, 487-498, (2001).
Roy, K. K., Early Development of Cyclin Dependent Kinase Modulators, Current Pharmaceutical Design, (2001), vol. 7, pp. 1669-1687.

* cited by examiner

*Primary Examiner* — Brandon Fetterolf
*Assistant Examiner* — Anna Pagonakis
(74) *Attorney, Agent, or Firm* — Scully, Scott, Murphy & Presser, P.C.

(57) ABSTRACT

This invention relates to benzimidazole and benzothiazole compounds of formula (I)

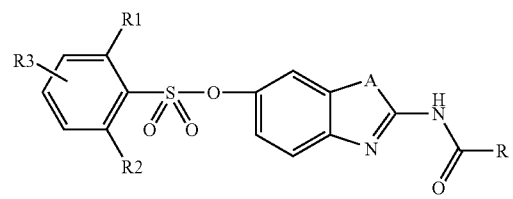

to methods of preparing such compounds, pharmaceutical compositions comprising such compounds, and to methods of treatment comprising administering of such compounds.

15 Claims, No Drawings

BENZIMIDAZOLE AND BENZOTHIAZOLE DERIVATIVES, METHOD FOR PREPARING SAME, USE THEREOF AS DRUGS, PHARMACEUTICAL COMPOSITIONS AND NOVEL USE ESPECIALLY AS C-MET INHIBITORS

The present invention relates to novel benzimidazole and benzothiazole derivatives, to a process for preparing them, to the novel intermediates obtained, to their use as medicaments, to pharmaceutical compositions containing them and to the novel use of such benzimidazole and benzothiazole derivatives.

The present invention more particularly relates to novel sulfonic ester derivatives of benzimidazoles and benzothiazoles.

One subject of the present invention is novel derivatives with inhibitory effects on protein kinases. The products according to the present invention may thus be used especially for preventing or treating diseases that may be modulated by inhibition of protein kinases.

The products according to the present invention especially show anticancer activity, via modulation of the activity of proteins, in particular kinases.

The present invention thus relates to the use of these derivatives as kinase inhibitors and more particularly as anticancer agents.

The present invention also relates to the use of the said derivatives for the preparation of a medicament for human therapy.

To date, most of the commercial compounds used in chemotherapy are cytotoxic, which poses major problems of side effects and of patient tolerance. These effects could be limited if the medicaments used acted selectively on cancer cells, to the exclusion of healthy cells. One of the solutions for limiting the adverse effects of a chemotherapy may thus consist in using medicaments that act on metabolic pathways or constituent elements of these pathways, predominantly expressed in the cancer cells, and which are sparingly expressed or not expressed in healthy cells.

Such protein kinases belong especially to the following group: AuroraA, AuroraB, the members of the family of CDKs (CDK1, 2, 4, 5, 7 and 9), RON, Tie2, the members of the family of VEGFRs (VEGFR1 or flt-1, VEGFR2 or KDR or flk-1, and VEGFR3), FGFRs (FGFR1, FGFR2, FGFR3, FGFR4 and FGFR5), MET and also mutants of the protein MET, EGFR, Fak, IGF-1R, PDGFR.

Mention is made more particularly of the protein kinase MET.

Protein kinases are a family of enzymes that catalyse the phosphorylation of hydroxyl groups of specific residues of proteins such as tyrosine, serine or threonine residues. Such phosphorylations can largely modify the function of proteins; thus, protein kinases play an important role in regulating a wide variety of cell processes, especially including metabolism, cell proliferation, cell adhesion and motility, cell differentiation or cell survival, certain protein kinases playing a central role in the initiation, development and accomplishment of cell cycle events.

Among the various cellular functions in which the activity of a protein kinase is involved, certain processes represent attractive targets for treating certain diseases. As an example, mention may be made especially of angiogenesis and the control of the cell cycle and also that of cell proliferation, in which protein kinases can play an essential role. These processes are especially essential for the growth of solid tumours and also for other diseases: in particular, molecules that inhibit such kinases are capable of limiting undesired cell proliferations such as those observed in cancers, and may play a part in preventing, regulating or treating neurodegenerative diseases such as Alzheimer's disease or neuronal apoptosis.

Angiogenesis is the process in which new vessels are formed from already-existing vessels. Should the need arise, the vascular system has the potential to generate a network of new vessels so as to maintain the correct functioning of the tissues and organs.

Angiogenesis is a complex multi-step process involving activation, migration, proliferation and survival of endothelial cells.

In adults, angiogenesis is fairly limited, appearing mainly only in the processes of repair after an injury or of vascularization of the endometrium (Merenmies and al., Cell Growth & Differentiation, 8, 3-10, 1997). However, uncontrolled angiogenesis is found in certain pathologies such as retinopathy, psoriasis, rheumatoid arthritis, diabetes, muscle degeneration or cancer (solid tumours) (Folkman, Nature Med., 1, 27-31, 1995). The kinase proteins whose involvement it has been possible to demonstrate in the angiogenesis process include three members of the family of growth factor receptor tyrosine kinases: VEGF-R2 (vascular endothelial growth factor receptor 2, also known as KDR, kinase insert domain receptor, or FLK-1), FGF-R (fibroblast growth factor receptor) and TEK (also known as Tie-2).

In conjunction with other systems, the Vascular Endothelial Growth Factor receptors (VEGFRs) transmit signals involved in the migration, proliferation and survival of endothelial cells. The family VEGFR includes VEGFR-1 (Flt-1), VEGFR-2 (KDR) and VEGFR3 (Flt4).

The receptor VEGF-R2, which is expressed only in the endothelial cells, binds to the angiogenic growth factor VEGF, and thus serves as a transduction signal mediator via the activation of its intracellular kinase domain. Thus, the direct inhibition of the kinase activity of VEGF-R2 makes it possible to reduce the phenomenon of angiogenesis in the presence of exogenous VEGF (Strawn and al., Cancer Research, 56, 3540-3545, 1996), this process being demonstrated especially with the aid of VEGF-R2 mutants (Millauer and al., Cancer Research, 56, 1615-1620, 1996). The VEGFR-2 receptor appears to have no other function in adults than that associated with the angiogenic activity of VEGF. Thus, a selective inhibitor of the kinase activity of VEGF-R2 should show only little toxicity.

In addition to this central role in the dynamic angiogenic process, recent results suggest that the expression of VEGF contributes towards the survival of tumoral cells after chemotherapy and radiotherapy, underlining the potential synergy of KDR inhibitors with other agents (Lee C. G., Heijn M. and al., (2000), Cancer Research, 60 (19), 5565-70).

Angiogenesis inhibitors might thus be used as a first line treatment against the emergence or regrowth of malignant tumours.

The inhibition or regulation of VEGFR-2 (KDR) thus provides a powerful new mechanism of action for the treatment of a large number of solid tumours.

Among the kinases for which modulation of activity is desired, the cyclin-dependent kinases and Aurora-2 may (or Aurora-A) be mentioned.

The progress of the cell cycle is often governed by cyclin-dependent kinases (CDKs), which are activated by means of an interaction with proteins belonging to the cyclin family, this activation terminating with the phosphorylation of substrates and finally with cell division. In addition, the endogenous CDK inhibitors that are activated (INK4 and KIP/CIP family) negatively regulate the activity of CDKs. The growth of normal cells is due to a balance between the CDK activators (the cyclins) and the endogenous CDK inhibitors. In several types of cancer, the aberrant activity or expression of several of these cell cycle regulators has been described.

Cyclin E activates the kinase CDK2, which then acts to phosphorylate the protein pRb (retinoblastoma protein), resulting in an engagement in irreversible cell division and transition towards the S phase (P L Toogood, Medicinal Research Reviews (2001), 21(6); 487-498. The kinase CDK2 and possibly CDK3 are necessary for progress in the G1 phase and entry into the S phase. During the formation of a complex with cyclin E, they maintain the hyperphosphorylation of pRb to aid the progress of the G1 phase into the S phase. In complexes with cyclin A, CDK2 plays a role in inactivating E2F and is necessary for producing the S phase (T. D. Davies and al. (2001) Structure 9, 389-3).

The CDK1/cyclin B complex regulates the progress of the cell cycle between the G2 phase and the M phase. Negative regulation of the CDK1/cyclin B complex prevents normal cells from entering the S phase before the G2 phase has been correctly and fully performed (K. K. Roy and E. A. Sausville Current Pharmaceutical Design, 2001, 7, 1669-1687).

A level of regulation of the activity of CDKs exists. Cyclin-dependent kinase activators (CAK) have a positive regulatory action on CDKs. CAK phosphorylates CDKs on the threonine residue to render the target enzyme fully active.

The presence of defects in molecules participating in the cell cycle results in activation of the CDKs and progress of the cycle; it is normal to wish to inhibit the activity of the CDK enzymes in order to block the cellular growth of cancer cells.

Many proteins involved in chromosome segregation and spindle assembly have been identified in yeast and *drosophila*. Disorganization of these proteins leads to the absence of segregation of the chromosomes and to monopolar or disorganized spindles. Among these proteins, certain kinases, including Aurora and Ipl1, originating from *drosophila* and from *S. cerevisiae*, respectively, are necessary for segregation of the chromosomes and separation of the centrosome. A human analogue of yeast Ipl1 has recently been cloned and characterized by various laboratories. This kinase, known as Aurora 2, STK15 or BTAK, belongs to the serine/threonine kinase family. Bischoff and al. have shown that Aurora 2 is oncogenic, and is amplified in human colorectal cancers (EMBO J, 1998, 17, 3052-3065). This has also been illustrated in cancers involving epithelial tumours such as breast cancer.

The present invention also relates to molecules that inhibit the tyrosine kinase activity of various kinases and most particularly that inhibit the activity of MET.

In the pharmacological section below, it is shown in biochemical tests and on cell lines that the products of the present patent application thus especially inhibit the autophosphorylation activity of MET and cell proliferation.

MET, or Hepatocyte Growth Factor Receptor, is a receptor with tyrosine kinase activity expressed in particular by epithelial and endothelial cells. HGF, Hepatocyte Growth Factor, is described as the specific ligand for MET. HGF is secreted by the mesenchymal cells and activates the MET receptor, which homodimerizes. Consequently, the receptor autophosphorylates on the tyrosines of the catalytic region Y1230, Y1234 and Y1235.

Stimulation of MET with HGF induces cell proliferation, scattering and motility, and resistance to apoptosis, invasion and angiogenesis.

MET and likewise HGF are found to be overexpressed in many human tumours and a wide variety of cancers. MET is also found to be amplified in gastric tumours and glioblastomas. Many point mutations of the MET gene have also been described in tumours, in particular in the kinase domain, but also in the juxtamembrane domain and the SEMA domain. Overexpression, amplification or mutations bring about constitutive activation of the receptor and deregulation of its functions.

The present invention thus concerns novel protein kinase inhibitors as defined above, especially having antiproliferative activity.

The present invention thus especially concerns novel protein kinase inhibitors as defined above, which may be used for an antiproliferative and anti-metastatic treatment, especially in oncology.

The present invention also concerns novel protein kinase inhibitors as defined above, which may be used for anti-angiogenic treatment, especially in oncology.

One subject of the present invention is thus the products of formula (I):

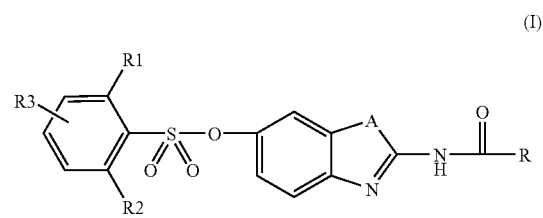

in which
A represents NH or S;
R1 and R2, which may be identical or different, are chosen from a hydrogen atom, an $NH_2$ radical, halogen atoms and alkyl radicals optionally substituted with one or more halogen atoms,
and R3 represents a hydrogen atom or is chosen from the values of R1 and R2,
it being understood that at least one from among R1, R2 and R3 does not represent hydrogen,
R represents:
  a cycloalkyl radical or an alkyl radical optionally substituted with a phenyl, heteroaryl, NR6R7 or heterocycloalkyl radical, which are themselves optionally substituted,
  an alkoxy, O-phenyl or O—CH$_2$-phenyl radical, with phenyl optionally substituted,
  or the radical NR4R5 in which R4 and R5 are such that one from among R4 and R5 represents a hydrogen atom or an alkyl radical and the other from among R4 and R5 represents a cycloalkyl radical or an alkyl radical optionally substituted with one or more radicals, which may be identical or different, chosen from hydroxyl, alkoxy, heteroaryl, heterocycloalkyl, NR6R7, optionally substituted phenyl, phenyl-NR6R7 and CONR6R7 radicals, with R6 and R7, which may be identical or different, representing a hydrogen atom, an alkyl radical or an optionally substituted phenyl radical, or alternatively R6 and R7 form, with the nitrogen atom to which they are attached, a cyclic radical optionally containing one or more other heteroatoms chosen from O, S, N and NH, this radical, including the possible NH it contains, being optionally substituted; or alternatively, R4 and R5 form, with the nitrogen atom to which they are attached, a cyclic radical optionally containing one or more other heteroatoms chosen from O, S, N and NH, this radical, including the possible NH it contains, being optionally substituted, all the cycloalkyl and heterocycloalkyl radicals being 3- to 7-membered, all the heterocycloalkyl, heteroaryl and phenyl radicals above being optionally substituted with one or more radicals chosen from halogen atoms, hydroxyl, oxo, alkoxy, $NH_2$; NHalk, $N(alk)_2$ radicals and alkyl, $CH_2$-heterocycloalkyl, $CH_2$-phenyl and CO-phenyl radicals, such that in these latter radicals the alkyl, heterocycloalkyl and phenyl radicals are themselves optionally substituted with one or more radicals chosen from halogen atoms and hydroxyl, oxo, alkyl and alkoxy containing from 1 to 4 carbon atoms, $NH_2$; NHalk and $N(alk)_2$ radicals, all the alkyl and alkoxy radicals containing from 1 to 6 carbon atoms, the said products of formula (I) being in any possible racemic, enantiomeric or diastereoisomeric isomer form, and also the addition salts with mineral and organic acids or with mineral and organic bases of the said products of formula (I).

One subject of the present invention is thus the products of formula (I) as defined above in which A, R1, R2 and R3 represent the values defined above and R represents:

a cycloalkyl radical or an alkyl radical optionally substituted with an optionally substituted pyridyl, NR6R7 or heterocycloalkyl radical, an alkoxy radical, or the radical NR4R5 in which R4 and R5 are such that one from among R4 and R5 represents a hydrogen atom or an alkyl radical and the other from among R4 and R5 represents a cycloalkyl radical or an alkyl radical optionally substituted with one or more radicals, which may be identical or different, chosen from hydroxyl; alkoxy; pyridyl; heterocycloalkyl; NR6R7; phenyl; phenyl-NR6R7 and CONR6R7 radicals, with R6 and R7, which may be identical or different, representing a hydrogen atom, an alkyl radical or an optionally substituted phenyl radical, or alternatively R6 and R7 form, with the nitrogen atom to which they are attached, a cyclic radical optionally containing one or more other heteroatoms chosen from O, S, N and NH, this radical, including the possible NH it contains, being optionally substituted; or alternatively R4 and R5 form, with the nitrogen atom to which they are attached, a cyclic radical optionally containing one or more other heteroatoms chosen from O, S, N and NH, this radical, including the possible NH it contains, being optionally substituted, all the cycloalkyl and heterocycloalkyl radicals being 3- to 7-membered, all the heterocycloalkyl and phenyl radicals above being optionally substituted with one or more radicals chosen from halogen atoms, hydroxyl, oxo, alkoxy, $NH_2$; NHalk and $N(alk)_2$ radicals, and alkyl, $CH_2$-pyrrolidinyl, $CH_2$-phenyl and CO-phenyl radicals in which the alkyl, pyrrolidinyl and phenyl radicals are themselves optionally substituted with one or more radicals chosen from halogen atoms and hydroxyl, oxo, alkyl and alkoxy containing from 1 to 4 carbon atoms, $NH_2$; NHalk and $N(alk)_2$ radicals, all the alkyl and alkoxy radicals containing from 1 to 6 carbon atoms, the said products of formula (I) being in any possible racemic, enantiomeric or diastereoisomeric isomer form, and also the addition salts with mineral and organic acids or with mineral and organic bases of the said products of formula (I).

One subject of the present invention is thus the products of formula (I) as defined above, in which:

A represents NH or S;

R1 and R2, which may be identical or different, are chosen from halogen atoms and alkyl radicals optionally substituted with one or more halogen atoms and R3 represents a hydrogen atom or is chosen from the values of R1 and R2, R represents the radical NR4R5 in which R4 and R5 are such that one from among R4 and R5 represents a hydrogen atom or an alkyl radical and the other from among R4 and R5 represents an alkyl radical optionally substituted with one or more radicals, which may be identical or different, chosen from hydroxyl, alkoxy and NR6R7 radicals, with R6 and R7, which may be identical or different, representing hydrogen or alkyl, or alternatively R6 and R7 form, with the nitrogen atom to which they are attached, a cyclic radical optionally containing one or more other heteroatoms chosen from O, S, N and NH, this radical, including the possible NH it contains, being optionally substituted; or alternatively R4 and R5 form, with the nitrogen atom to which they are attached, a cyclic radical optionally containing one or more other heteroatoms chosen from O, S, N and NH, this radical, including the possible NH it contains, being optionally substituted;

all the alkyl and alkoxy radicals containing from 1 to 6 carbon atoms, the said products of formula (I) being in any possible racemic, enantiomeric or diastereoisomeric isomer form, and also the addition salts with mineral and organic acids or with mineral and organic bases of the said products of formula (I).

In the products of formula (I) and in the text hereinbelow:

the term "alkyl radical" denotes linear and, where appropriate, branched methyl, ethyl, propyl, isopropyl, butyl, isobutyl, sec-butyl, tert-butyl, pentyl, isopentyl, hexyl, isohexyl, heptyl, octyl, nonyl and decyl radicals and also the linear or branched regioisomers thereof: alkyl radicals containing from 1 to 6 carbon atoms and more particularly alkyl radicals containing from 1 to 4 carbon atoms from the above list are preferred;

the term "alkoxy radical" denotes linear and, where appropriate, branched methoxy, ethoxy, propoxy, isopropoxy, linear, secondary or tertiary butoxy, pentoxy or hexoxy radicals, and also the linear or branched regioisomers thereof: alkoxy radicals containing from 1 to 4 carbon atoms from the above list are preferred;

the term "halogen atom" denotes chlorine, bromine, iodine or fluorine atoms and preferably a chlorine, bromine or fluorine atom.

The carboxyl radical(s) of the products of formula (I) may be salified or esterified with various groups known to those skilled in the art, among which examples that may be mentioned include:

among the salification compounds, mineral bases, for instance one equivalent of sodium, potassium, lithium, calcium, magnesium or ammonium, or organic bases, for instance methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine and N-methylglucamine, among the esterification compounds, alkyl radicals to form alkoxycarbonyl groups, for instance methoxycarbonyl, ethoxycarbonyl, tert-butoxycarbonyl or benzyloxycarbonyl, these alkyl radicals possibly being substituted with radicals chosen, for example, from halogen atoms and hydroxyl, alkoxy, acyl, acyloxy, alkylthio, amino and aryl radicals, for instance from the group: chloromethyl, hydroxypropyl, methoxymethyl, propionyloxymethyl, methylthiomethyl, dimethylaminoethyl, benzyl and phenethyl.

The addition salts with mineral or organic acids of the products of formula (I) may be, for example, the salts formed with hydrochloric, hydrobromic, hydriodic, nitric, sulfuric, phosphoric, propionic, acetic, trifluoroacetic, formic, benzoic, maleic, fumaric, succinic, tartaric, citric, oxalic, glyoxylic, aspartic or ascorbic acid, alkylmonosulfonic acids, for instance methanesulfonic acid, ethanesulfonic acid, propanesulfonic acid, alkyldisulfonic acids, for instance methanedisulfonic acid, $\alpha,\beta$-ethanedisulfonic acid, arylmonosulfonic acids such as benzenesulfonic acid, and aryldisulfonic acids.

It may be recalled that stereoisomerism may be defined in its broadest sense as the isomerism of compounds having the same structural formulae, but in which the various groups are arranged differently in space, especially such as in the case of monosubstituted cyclohexanes whose substituent may be in an axial or equatorial position, and the various possible rotational conformations of ethane derivatives. However, there is another type of stereoisomerism, due to the various spatial arrangements of fixed substituents, either on double bonds or on rings, which is often referred to as geometrical isomerism or cis-trans isomerism. The term "stereoisomers" is used in the present application in its broadest sense and thus concerns all of the compounds indicated above.

One subject of the present invention is thus products of formula (I) in which:
R1 and R2, which may be identical or different, are chosen from fluorine or chlorine atoms and alkyl radicals, and R3 represents a hydrogen atom or an alkyl radical optionally substituted with one or more fluorine atoms,
the radicals A and R being chosen from the values defined for these radicals,
all the alkyl and alkoxy radicals containing from 1 to 4 carbon atoms,
the said products of formula (I) being in any possible racemic, enantiomeric or diastereoisomeric isomer form, and also the addition salts with mineral and organic acids or with mineral and organic bases of the said products of formula (I).

One subject of the present invention is thus products of formula (I) in which
R1 and R2, which may be identical or different, are chosen from fluorine or chlorine atoms and a methyl radical, and R3 represents a hydrogen atom, a methyl radical or $CF_3$,
the radicals A and R being chosen from the values defined for these radicals,
all the alkyl and alkoxy radicals containing from 1 to 4 carbon atoms,
the said products of formula (I) being in any possible racemic, enantiomeric or diastereoisomeric isomer form, and also the addition salts with mineral and organic acids or with mineral and organic bases of the said products of formula (I).

One subject of the present invention is thus products of formula (I) in which:
R represents the radical NR4R5 in which R4 and R5 are such that one from among R4 and R5 represents a hydrogen atom or an alkyl radical and the other from among R4 and R5 represents an alkyl radical substituted with one or more radicals, which may be identical or different, chosen from hydroxyl, alkoxy and NR6R7 radicals, with R6 and R7, which may be identical or different, representing hydrogen or alkyl, or alternatively R6 and R7 form, with the nitrogen atom to which they are attached, a cyclic radical optionally containing one or more other heteroatoms chosen from O, S, N and NH, this radical, including the possible NH it contains, being optionally substituted;
the radicals A, R1, R2 and R3 being chosen from the values defined for these radicals,
all the alkyl and alkoxy radicals containing from 1 to 4 carbon atoms,
the said products of formula (I) being in any possible racemic, enantiomeric or diastereoisomeric isomer form, and also the addition salts with mineral and organic acids or with mineral and organic bases of the said products of formula (I).

The cyclic radicals that R4 and R5 may form, on the one hand, with the nitrogen atom to which they are attached and, on the other hand, which R6 and R7 may form with the nitrogen atom to which they are attached, are optionally substituted with one or more radicals chosen from those indicated above for the possible substituents of the heterocycloalkyl radicals, i.e. one or more radicals chosen from halogen atoms, hydroxyl, oxo, alkoxy, $NH_2$; NHalk and $N(alk)_2$ radicals, and alkyl, $CH_2$-heterocycloalkyl, $CH_2$-phenyl and CO-phenyl radicals, such that, in the latter radicals, the alkyl, heterocycloalkyl and phenyl radicals are themselves optionally substituted with one or more radicals chosen from halogen atoms and hydroxyl, oxo, alkyl and alkoxy containing from 1 to 4 carbon atoms, $NH_2$; NHalk and $N(alk)_2$ radicals.

The cyclic radicals that, on the one hand, R4 and R5 may form with the nitrogen atom to which they are attached and, on the other hand, that R6 and R7 may form with the nitrogen atom to which they are attached are especially optionally substituted with one or more radicals, which may be identical or different, chosen from halogen atoms and alkyl, hydroxyl, alkoxy, $CH_2$-pyrrolidinyl, $CH_2$-phenyl and phenyl radicals, in which the alkyl, pyrrolidinyl and phenyl radicals are themselves optionally substituted with one or more radicals, which may be identical or different, chosen from halogen atoms and alkyl, hydroxyl, oxo and alkoxy radicals.

When R as defined above represents the radical NR4R5 and when this radical is not cyclized, the present invention especially relates to products of formula (I) as defined above, in which R4 and R5 are such that one from among R4 and R5 represents a hydrogen atom or an alkyl radical and the other from among from R4 and R5 represents a cycloalkyl radical or an alkyl radical optionally substituted with a radical chosen from hydroxyl; alkoxy; pyridyl; heterocycloalkyl; NR6R7; phenyl; phenyl-NR6R7 and CONR6R7 radicals, as defined above or below.

The heterocycloalkyl radicals as defined above especially represent azepanyl, morpholinyl and pyrrolidinyl radicals, and piperidyl and piperazinyl radicals, which are themselves optionally substituted, as defined above or below.

The heteroaryl radicals especially represent a pyridyl radical.

When NR4R5 or NR6R7 forms a ring as defined above, such an amino ring may be chosen especially from pyrrolidinyl, pyrazolidinyl, pyrazolinyl, piperidyl, morpholino and piperazinyl radicals, these radicals themselves being optionally substituted as indicated above or below, for example with one or more radicals, which may be identical or different, chosen from halogen atoms and alkyl, hydroxyl, alkoxy and phenyl radicals, the alkyl or phenyl radicals being themselves optionally substituted with one or more radicals, which may be identical or different, chosen from halogen atoms and alkyl, hydroxyl and alkoxy radicals.

The ring NR4R5 or NR6R7 may be chosen more particularly from pyrrolidinyl, morpholino or piperazinyl radicals optionally substituted on the second nitrogen atom with an alkyl or phenyl radical, which are themselves optionally substituted with one or more radicals, which may be identical or different, chosen from halogen atoms and alkyl, hydroxyl and alkoxy radicals.

A subject of the present invention is particularly products of formula (I) as defined above in which A, R1, R2 and R3 represent the values defined above and R represents:
  a cycloalkyl radical or an alkyl radical optionally substituted with a pyridyl, morpholinyl or piperidyl radical optionally substituted with CO-phenyl, with phenyl itself optionally substituted,
  an alkoxy radical,
  or the radical NR4R5 in which R4 and R5 are such that one from among R4 and R5 represents a hydrogen atom or an alkyl radical and the other from among R4 and R5 represents a cycloalkyl radical or an alkyl radical optionally substituted with a radical chosen from hydroxyl; alkoxy; pyridyl; NHalk; N(alk)$_2$; Nalkphenyl; azepanyl; morpholinyl; pyrrolidinyl; piperidyl; piperazinyl; CO-piperazinyl; phenyl; phenyl substituted with morpholinyl, N(alk)$_2$ or piperazinyl radicals;
  or R4 and R5 form, with the nitrogen atom to which they are attached, a pyrrolidinyl radical;
all the pyrrolidinyl, piperidyl and piperazinyl radicals above being optionally substituted with 1 or 2 CH$_3$, CH$_2$-pyrrolidinyl, CH$_2$-phenyl or CO-phenyl;
all the pyrrolidinyl radicals above also being optionally substituted with oxo,
all the phenyl radicals above themselves being optionally substituted with one or more radicals, which may be identical or different, chosen from halogen atoms and alkyl, hydroxyl and alkoxy radicals,
all the alkyl and alkoxy radicals containing from 1 to 4 carbon atoms,
the said products of formula (I) being in any possible racemic, enantiomeric or diastereoisomeric isomer form, and also the addition salts with mineral and organic acids or with mineral and organic bases of the said products of formula (I).

One subject of the present invention is thus products of formula (I) in which:
  R represents a radical NHalkyl with alkyl containing 1 or 2 carbon atoms substituted with an alkoxy or morpholino radical,
  the radicals A, R1, R2 and R3 being chosen from the values defined for these radicals,
the said products of formula (I) being in any possible racemic, enantiomeric or diastereoisomeric isomer form, and also the addition salts with mineral and organic acids or with mineral and organic bases of the said products of formula (I).

A subject of the present invention is especially products of formula (I) in which A represents NH, the radicals R1, R2, R3 and R being chosen from all the values defined for these radicals above or below, the said products of formula (I) being in any possible racemic, enantiomeric or diastereoisomeric isomer form, and also the addition salts with mineral and organic acids or with mineral and organic bases of the said products of formula (I).

A subject of the present invention is especially products of formula (I) as defined above in which A represents S, the radicals R1, R2, R3 and R being chosen from all the values defined for these radicals above or below, the said products of formula (I) being in any possible racemic, enantiomeric or diastereoisomeric isomer form, and also the addition salts with mineral and organic acids or with mineral and organic bases of the said products of formula (I).

A subject of the present invention is especially products of formula (I) as defined above in which R1 and R2, which may be identical or different, represent a chlorine atom or a methyl radical, the radicals R3, A and R being chosen from the values defined above for these radicals.

A subject of the present invention is especially products of formula (I) as defined above in which R1 and R2 both represent a chlorine atom, the radicals R3, A and R being chosen from the values defined above for these radicals.

A subject of the present invention is especially products of formula (I) as defined above in which R1 and R2 both represent a fluorine atom and R represents a radical NR4R5 in which R4 and R5 are such that one from among R4 and R5 represents a hydrogen atom or an alkyl radical and the other from among R4 and R5 represents a substituted alkyl radical as defined above, the radicals R3 and A being chosen from the values defined above for these radicals.

A subject of the present invention is most particularly products of formula (I) as defined above corresponding to the following formulae:
  2-({[2-(4-benzylpiperazin-1-yl)ethyl]carbamoyl}amino)-1,3-benzothiazol-6-yl 2,6-dichlorobenzenesulfonate
  2-{[(3-morpholin-4-ylpropyl)carbamoyl]amino}-1,3-benzothiazol-6-yl 2,6-dichlorobenzenesulfonate
  2-{[(2-pyrrolidin-1-ylethyl)carbamoyl]amino}-1,3-benzothiazol-6-yl 2,6-dichlorobenzenesulfonate
  2-{[(3-pyrrolidin-1-ylpropyl)carbamoyl]amino}-1,3-benzothiazol-6-yl 2,6-dichlorobenzenesulfonate
  2-({[2-(4-methylpiperazin-1-yl)ethyl]carbamoyl}amino)-1,3-benzothiazol-6-yl 2,6-dichlorobenzenesulfonate
  2-({[2-(1-methylpyrrolidin-2-yl)ethyl]carbamoyl}amino)-1,3-benzothiazol-6-yl 2,6-dichlorobenzenesulfonate
  2-({[3-(dimethylamino)propyl]carbamoyl}amino)-1,3-benzothiazol-6-yl 2,6-dichlorobenzenesulfonate
  2-({[2-(2,6-dimethylpiperidin-1-yl)ethyl]carbamoyl}amino)-1,3-benzothiazol-6-yl 2,6-dichlorobenzenesulfonate
  2-{[(2-piperidin-1-ylethyl)carbamoyl]amino}-1,3-benzothiazol-6-yl 2,6-dichlorobenzenesulfonate
  2-({[3-(2-oxopyrrolidin-1-yl)propyl]carbamoyl}amino)-1,3-benzothiazol-6-yl 2,6-dichlorobenzenesulfonate
  2-({[3-(4-benzylpiperazin-1-yl)propyl]carbamoyl}amino)-1,3-benzothiazol-6-yl 2,6-dichlorobenzenesulfonate
  2-({[3-(4-methylpiperazin-1-yl)propyl]carbamoyl}amino)-1,3-benzothiazol-6-yl 2,6-dichlorobenzenesulfonate
  2-[(methylcarbamoyl)amino]-1,3-benzothiazol-6-yl 2,6-dichlorobenzenesulfonate
  2-{[(2-azepan-1-ylethyl)carbamoyl]amino}-1,3-benzothiazol-6-yl 2,6-dichlorobenzenesulfonate
and also the addition salts with mineral and organic acids or with mineral and organic bases of the said products of formula (I).

A subject of the present invention is particularly products of formula (I) as defined above corresponding to the following formulae:
  2-{[(2-methoxyethyl)carbamoyl]amino}-1H-benzimidazol-5-yl 2,6-dichlorobenzenesulfonate
  2-{[(2-methoxyethyl)carbamoyl]amino}-1H-benzimidazol-5-yl 2-chloro-6-methyl benzenesulfonate
  2-{[(2-methoxyethyl)carbamoyl]amino}-1H-benzimidazol-5-yl 2,4,6-trimethylbenzenesulfonate
  2-{[(2-methoxyethyl)carbamoyl]amino}-1H-benzimidazol-5-yl 2,6-dichloro-4-(trifluoromethyl)benzenesulfonate
  2-{[(2-morpholin-4-ylethyl)carbamoyl]amino}-1H-benzimidazol-5-yl 2,6-dichlorobenzenesulfonate 2-{[(2-morpholin-4-ylethyl)carbamoyl]amino}-1,3-benzothiazol-6-yl 2,6-dichlorobenzenesulfonate
2-{[(2-morpholin-4-ylethyl)carbamoyl]amino}-1,3-benzothiazol-6-yl 2,6-difluorobenzenesulfonate
2-{[(2-methoxyethyl)carbamoyl]amino}-1,3-benzothiazol-6-yl 2,6-difluorobenzenesulfonate and also the addition salts with mineral and organic acids or with mineral and organic bases of the said products of formula (I).

A subject of the present invention is particularly products of formula (I) as defined above corresponding to the following formulae:

2-{[(2-methoxyethyl)carbamoyl]amino}-1H-benzimidazol-5-yl 2,6-dichlorobenzenesulfonate
2-{[(2-methoxyethyl)carbamoyl]amino}-1H-benzimidazol-5-yl 2-chloro-6-methylbenzenesulfonate
2-{[(2-methoxyethyl)carbamoyl]amino}-1H-benzimidazol-5-yl 2,6-dichloro-4-(trifluoromethyl)benzenesulfonate
2-{[(2-morpholin-4-ylethyl)carbamoyl]amino}-1H-benzimidazol-5-yl 2,6-dichlorobenzenesulfonate
2-{[(2-morpholin-4-ylethyl)carbamoyl]amino}-1,3-benzothiazol-6-yl 2,6-dichlorobenzenesulfonate
2-({[2-(4-benzylpiperazin-1-yl)ethyl]carbamoyl}amino)-1,3-benzothiazol-6-yl 2,6-dichlorobenzenesulfonate
2-{[(3-morpholin-4-ylpropyl)carbamoyl]amino}-1,3-benzothiazol-6-yl 2,6-dichlorobenzenesulfonate
2-{[(3-pyrrolidin-1-ylpropyl)carbamoyl]amino}-1,3-benzothiazol-6-yl 2,6-dichlorobenzenesulfonate
2-({[2-(4-methylpiperazin-1-yl)ethyl]carbamoyl}amino)-1,3-benzothiazol-6-yl 2,6-dichlorobenzenesulfonate
2-({[2-(1-methylpyrrolidin-2-yl)ethyl]carbamoyl}amino)-1,3-benzothiazol-6-yl 2,6-dichlorobenzenesulfonate
2-({[3-(dimethylamino)propyl]carbamoyl}amino)-1,3-benzothiazol-6-yl 2,6-dichlorobenzenesulfonate
2-{[(2-azepan-1-ylethyl)carbamoyl]amino}-1,3-benzothiazol-6-yl 2,6-dichlorobenzenesulfonate and also the addition salts with mineral and organic acids or with mineral and organic bases of the said products of formula (I).

A subject of the present invention is particularly products of formula (I) as defined above corresponding to the following formulae:

2-{[(2-methoxyethyl)carbamoyl]amino}-1H-benzimidazol-5-yl 2,6-dichlorobenzenesulfonate
2-{[(2-methoxyethyl)carbamoyl]amino}-1H-benzimidazol-5-yl 2-chloro-6-methylbenzenesulfonate
2-{[(2-methoxyethyl)carbamoyl]amino}-1H-benzimidazol-5-yl 2,6-dichloro-4-(trifluoromethyl)benzenesulfonate
2-{[(2-morpholin-4-ylethyl)carbamoyl]amino}-1H-benzimidazol-5-yl 2,6-dichlorobenzenesulfonate
2-({[2-(4-benzylpiperazin-1-yl)ethyl]carbamoyl}amino)-1,3-benzothiazol-6-yl 2,6-dichlorobenzenesulfonate
2-{[(3-morpholin-4-ylpropyl)carbamoyl]amino}-1,3-benzothiazol-6-yl 2,6-dichlorobenzenesulfonate
2-{[(3-pyrrolidin-1-ylpropyl)carbamoyl]amino}-1,3-benzothiazol-6-yl 2,6-dichlorobenzenesulfonate
2-({[2-(4-methylpiperazin-1-yl)ethyl]carbamoyl}amino)-1,3-benzothiazol-6-yl 2,6-dichlorobenzenesulfonate
2-({[2-(1-methylpyrrolidin-2-yl)ethyl]carbamoyl}amino)-1,3-benzothiazol-6-yl 2,6-dichlorobenzenesulfonate
2-({[3-(dimethylamino)propyl]carbamoyl}amino)-1,3-benzothiazol-6-yl 2,6-dichlorobenzenesulfonate and also the addition salts with mineral and organic acids or with mineral and organic bases of the said products of formula (I).

A subject of the present invention is particularly products of formula (I) as defined above corresponding to the following formulae:

2-[3(2-morpholin-4-yl-ethyl)-ureido]-benzothiazol-6-yl 2,6-dichlorobenzenesulfonate
2-({[2-(4-benzylpiperazin-1-yl)ethyl]carbamoyl}amino)-1,3-benzothiazol-6-yl 2,6-dichlorobenzenesulfonate
2-{[(3-morpholin-4-ylpropyl)carbamoyl]amino}-1,3-benzothiazol-6-yl 2,6-dichlorobenzenesulfonate
2-{[(3-pyrrolidin-1-ylpropyl)carbamoyl]amino}-1,3-benzothiazol-6-yl 2,6-dichlorobenzenesulfonate and also the addition salts with mineral and organic acids or with mineral and organic bases of the said product of formula (I).

The products of formula (I) as defined above according to the present invention may be prepared according to the usual methods known to those skilled in the art.

The products of formula (I) as defined above according to the present invention may be prepared according to the processes described in Schemes 1 and 2 below.

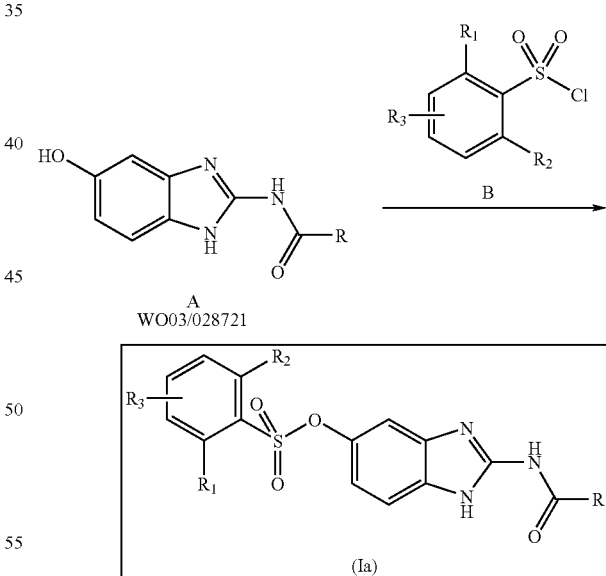

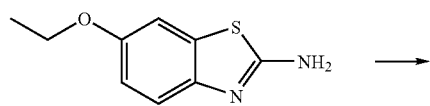

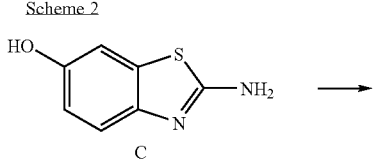

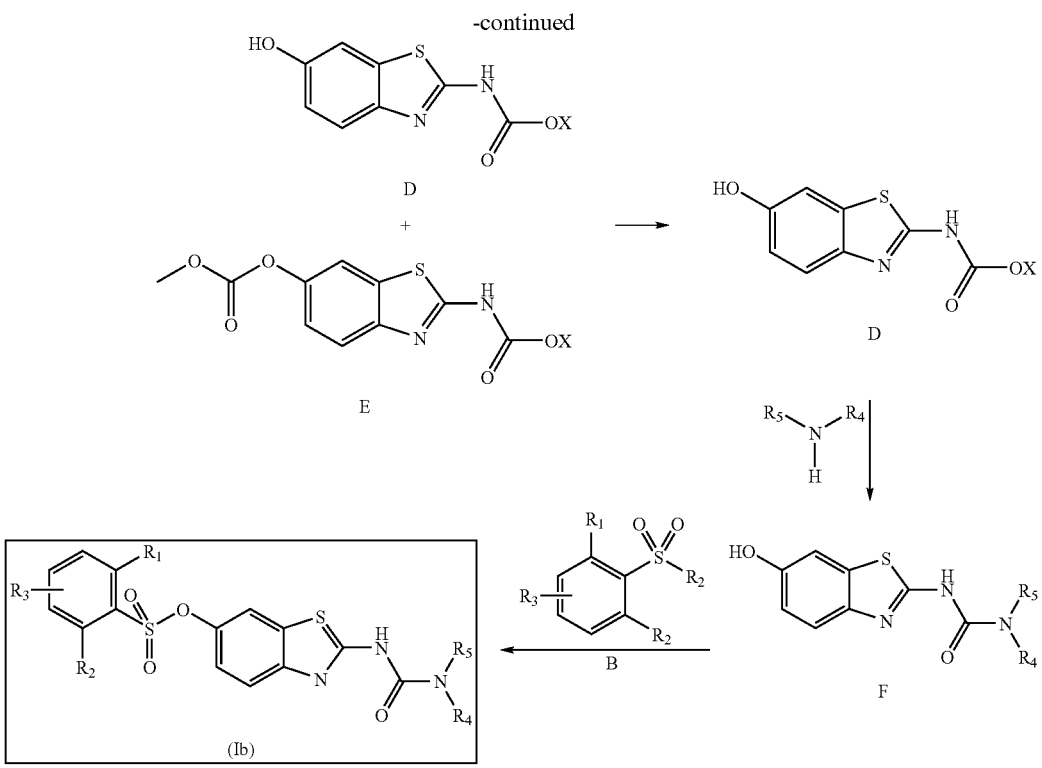

A subject of the present invention is thus also a process, according to Scheme 1 above, for preparing the products of formula (I) as defined above, characterized in that a compound of formula (A):

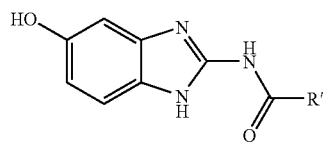

(A)

in which R' has the meaning given above for R in which the potentially reactive functions are optionally protected,
is reacted with a compound of formula (B):

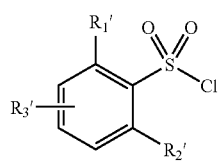

(B)

in which R1', R2' and R3' have the meanings given above, respectively, for R1, R2 and R3 in which the potentially reactive functions are optionally protected, to obtain a product of formula (Ia):

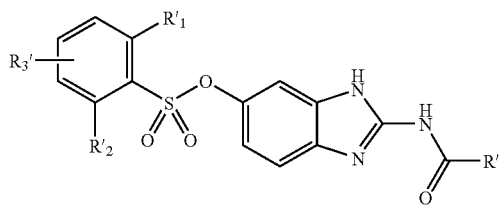

(Ia)

in which R1', R2', R3' and R' have the meanings given above, which products of formula (Ia) thus obtained may be products of formula (I) in which A represents NH and which, in order to obtain products or other products of formula (I), may be subjected, if desired and if necessary, to one or more of the following conversion reactions, in any order:

a) an esterification reaction of an acid function,
b) a saponification reaction of an ester function to an acid function,
c) a reduction reaction of the free or esterified carboxyl function to an alcohol function,
d) a conversion reaction of an alkoxy function to a hydroxyl function, or alternatively of a hydroxyl function to an alkoxy function,
e) a reaction for removal of the protecting groups that the protected reactive functions may bear,
f) a salification reaction with a mineral or organic acid or with a base to obtain the corresponding salt,
g) a reaction for resolution of racemic forms as resolved products,
the said products of formula (I) thus obtained being in any possible racemic, enantiomeric or diastereoisomeric isomer form.

The compounds of the present invention of general formula (Ia) may thus be prepared by reaction between benzimidazoles of general formula (A) and a sulfonyl chloride of formula (B) in the presence of a base such as aqueous sodium hydroxide.

The benzimidazole derivatives of general formula (A) may be prepared especially as described in patent WO 03028 721 A2.

A subject of the present invention is thus also a process, according to Scheme 2 above, for preparing the products of formula (I) as defined above, characterized in that the compound of formula (D):

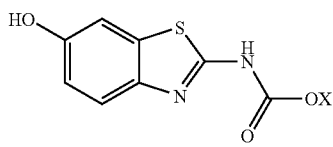

in which COOX represents an $NH_2$ protecting group, is reacted with an amine of formula (G): H—NR4'R5' (G)

in which R4' and R5' have the meanings indicated above for R4 and R5 in which the potentially reactive functions are optionally protected, to obtain a compound of formula (F):

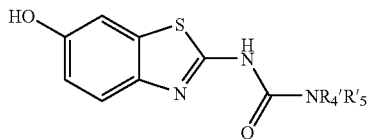

in which R4' and R5' have the meanings given above, which compound of formula F is reacted with the compound of formula (B) as defined above to obtain a product of formula (Ib):

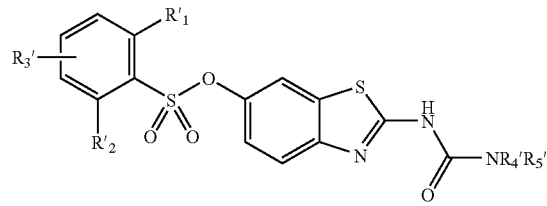

in which R1', R2', R3', R4' and R5' have the meanings given above, which products of formula (Ib) thus obtained may be products of formula (I) in which A represents S and which, in order to obtain products or other products of formula (I), may be subjected, if desired and if necessary, to one or more of the following conversion reactions, in any order:

a) an esterification reaction of an acid function, b) a saponification reaction of an ester function to an acid function, c) a reduction reaction of the free or esterified carboxyl function to an alcohol function, d) a conversion reaction of an alkoxy function to a hydroxyl function, or alternatively of a hydroxyl function to an alkoxy function, e) a reaction for removal of the protecting groups that the protected reactive functions may bear, f) a salification reaction with a mineral or organic acid or with a base to obtain the corresponding salt, g) a reaction for resolution of racemic forms as resolved products, the said products of formula (I) thus obtained being in any possible racemic, enantiomeric or diastereoisomeric isomer form.

In Scheme 2 above, the compounds of general formula (Ib) may be prepared from 6-ethoxy-1,3-benzothiazol-2-amine (commercial compound).

2-Amino-1,3-benzothiazol-6-ol (C) may be obtained by cleaving 6-ethoxy-1,3-benzothiazol-2-amine, in acidic medium, preferentially in an acetic acid/aqueous hydrobromic acid mixture.

The ester derivatives of (6-hydroxy-benzothiazol-2-yl)carbamic acid, i.e. the carbamates of general formula (D), may be obtained, after treatment with an aqueous potassium hydroxide solution, from a mixture of ester derivatives of 2-methoxycarbonylaminobenzothiazol-6-ylcarbonic acid (E) and of ester derivatives of (6-hydroxybenzothiazol-2-yl) carbamic acid (D), and thus a mixture of derivatives of general formulae (E) and (D).

The mixture of compounds (E) and (D) may be obtained by reacting an alkyl chloroformate in the presence of a base such as pyridine at a temperature in the region of 20° C.

The compounds of general formula (F) are obtained by reaction between the carbamic derivative of general formula (D) and an amine (R'' as defined in the general formula (I)) in the presence of an aprotic solvent such as 1-methylpyrrolidin-2-one. The reaction may be performed at a temperature ranging from 90 to 150° C. in a sealed microwave tube.

The sulfono esters of formula (Ib) are obtained by reaction between the compounds of general formula (F) and a sulfonyl chloride of formula (B) (R1, R2 and R3 as defined in the general formula (I) in the presence of a base such as aqueous sodium hydroxide.

The products of formula (I) as defined above according to the present invention may also be prepared according to the processes described in Schemes 1a and 2a below.

Scheme 1a is split below into two parts, Scheme 1aa and Scheme 1ab for greater clarity in its presentation.

Scheme 1aa
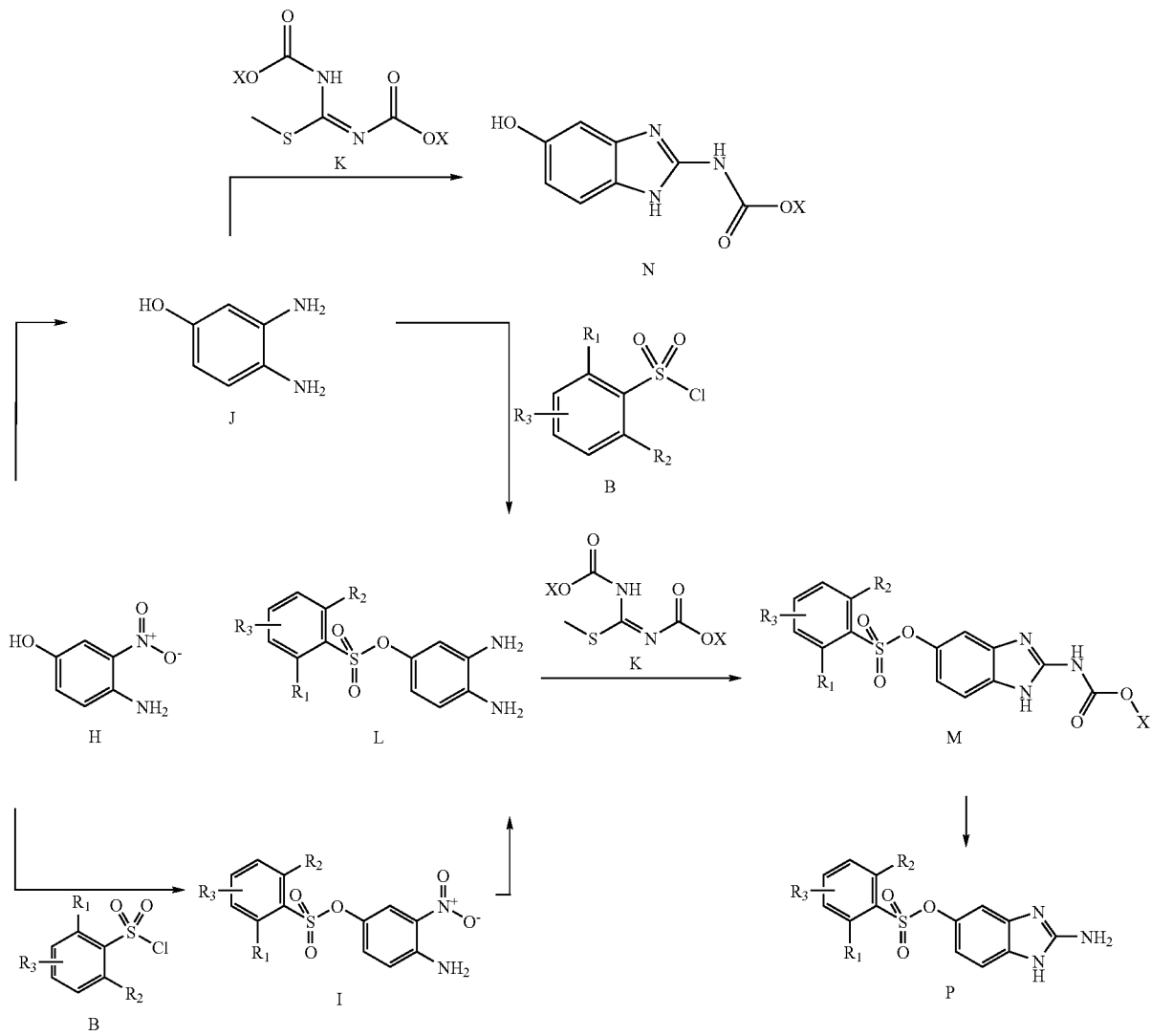
Scheme 1ab
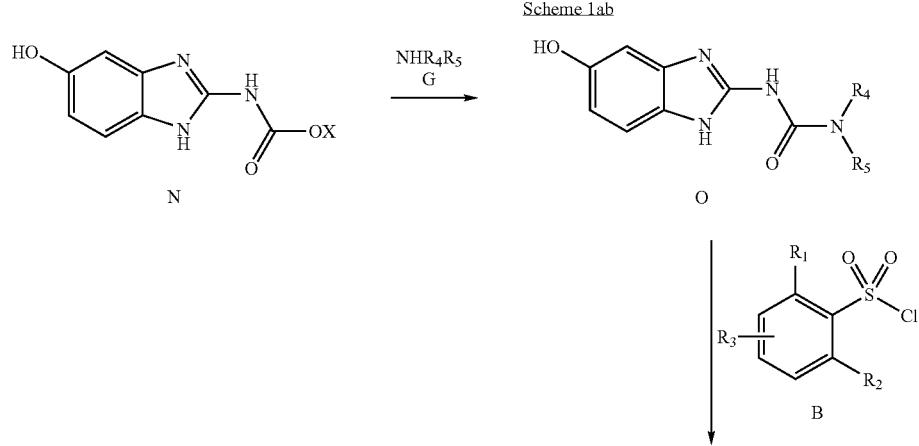

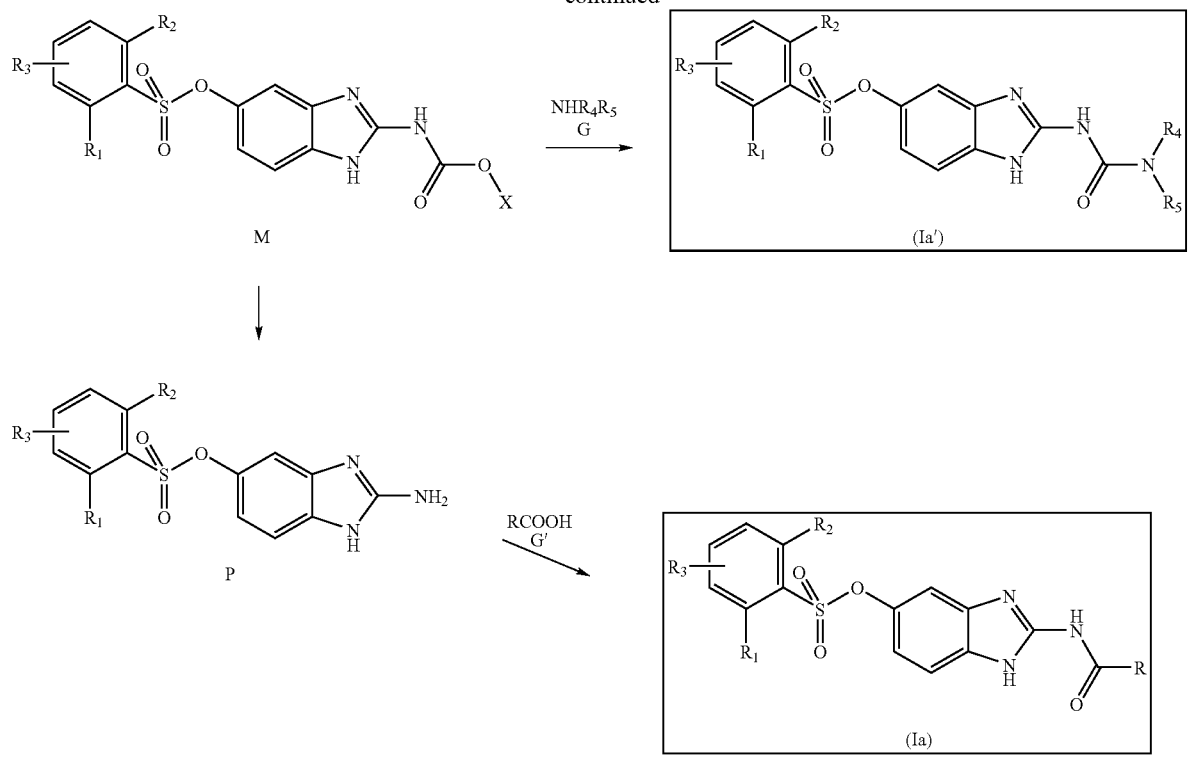
Scheme 2a is split below into two parts, Scheme 2aa and Scheme 2ab for greater clarity in its presentation.
Scheme 2aa
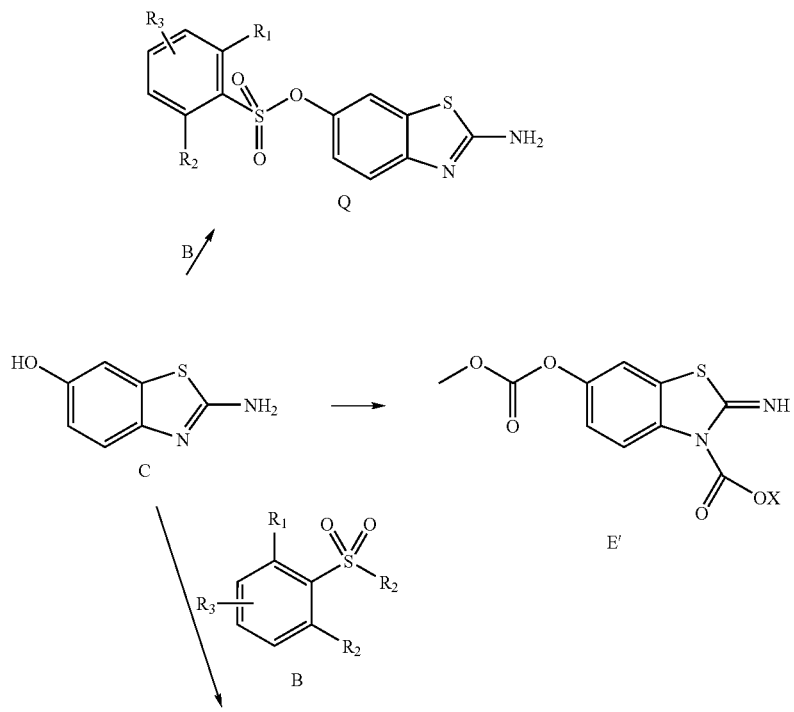

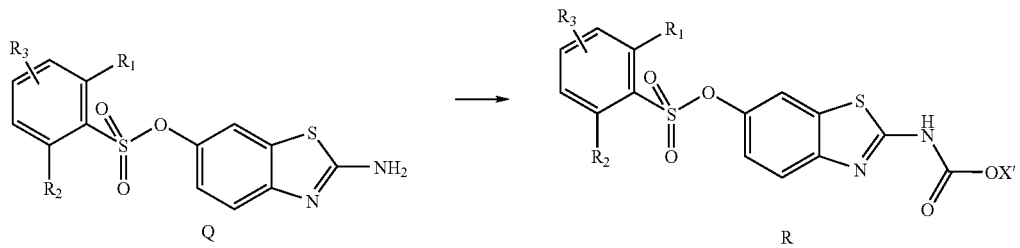
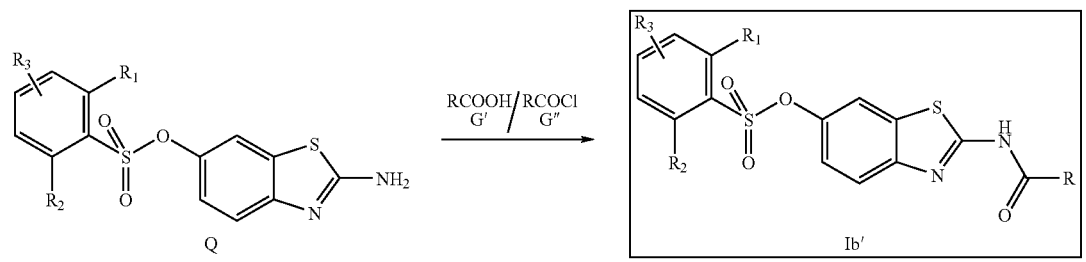
Scheme 2ab
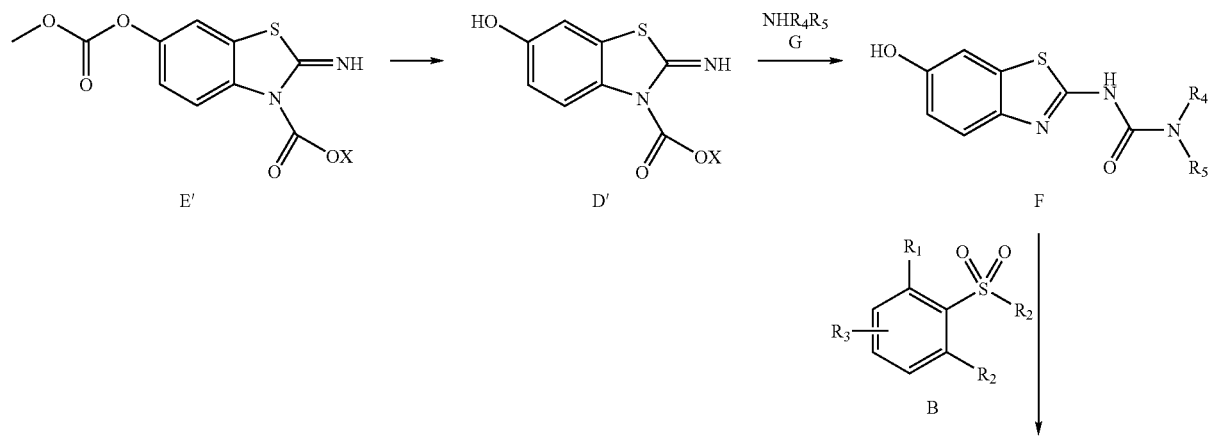
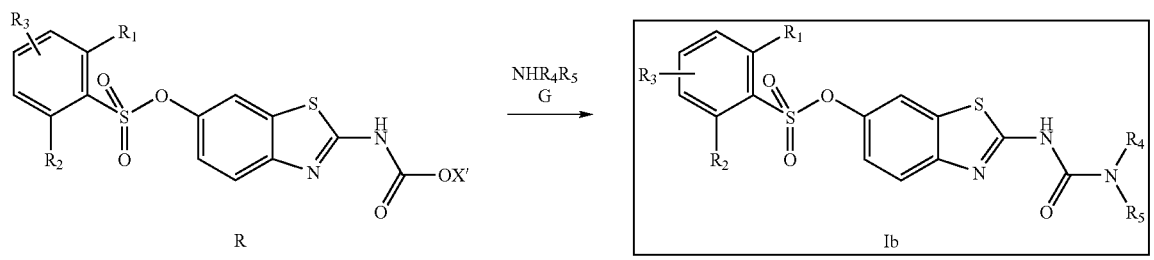

A subject of the present invention is thus also a process, according to Scheme 1a above, for preparing products of formula (Ia) and (Ia') as defined above, characterized in that either a product of formula (H) or a product of formula (J)

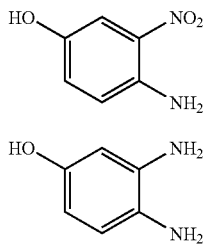

(H)

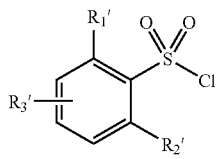

(J)

is reacted with a compound of formula (B):

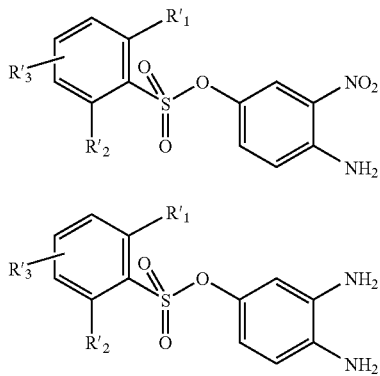

(B)

in which R1', R2' and R3' have the meanings given above, respectively, for R1, R2 and R3 in which the potentially reactive functions are optionally protected,
to obtain, respectively, a product of formula (I) or (L):

(I)

(L)

in which R1', R2' and R3' have the meanings given above.

The compound of formula (L) may also be obtained by reduction of the compound of formula (I).

A product of formula (L) is then reacted with a compound of formula (K):

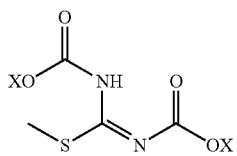

(K)

in which COOX represents an NH$_2$-protecting group, to obtain a product of formula (M):

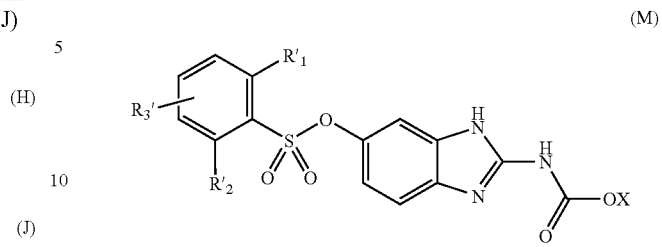

(M)

in which R1', R2' and R3' have the meanings given above.

The compound of formula (M) may give, after deprotection of the group COOX, a product of formula (P):

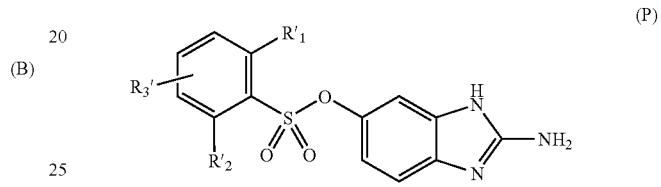

(P)

in which R1', R2' and R3' have the meanings given above.

This compound of formula (P) may react with an acid of formula (G'): R'COOH (G') in which R' has the meanings given above for R in which the potentially reactive functions are optionally protected,
to obtain a compound of formula (Ia):

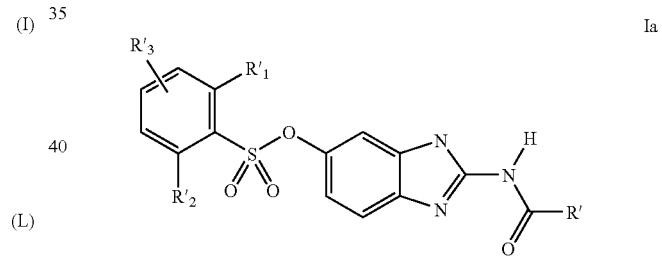

Ia in which R', R'1, R'2 and R'3 have the meanings given above,

The product of formula (M) may also react with an amine of formula (G):
H—NR4'R5' (G) in which R4' and R5' have the meanings given above for R4 and R5 in which the potentially reactive functions are optionally protected,
to obtain a compound of formula (Ia'):

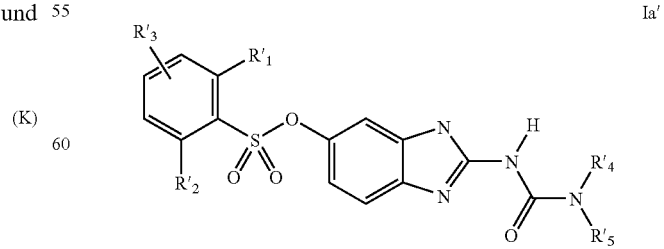

Ia' in which R'1, R2, R'3, R4' and R5' have the meanings given above.

The products of formula (Ia') may also be obtained from a compound of formula (J) on which is reacted a compound of formula (K) to obtain a product of formula (N):

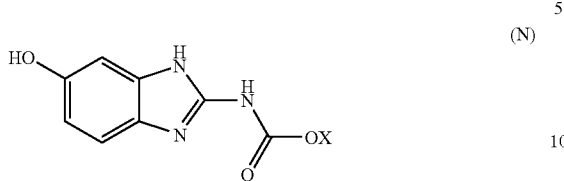

in which COOX has the meanings given above.

The product of formula (N) may then react with an amine of formula (G): to obtain a product of formula (O):

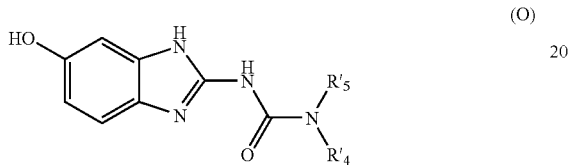

in which R4' and R5' have the meanings given above.

The product of formula (O) may then react with a compound of formula (B): to obtain a product of formula (Ia').

The products of formulae (Ia) and (Ia') thus obtained, which may be products of formula (I) in which A represents NH and which, in order to obtain products or other products of formula (I), may be subjected, if desired and if necessary, to one or more of the conversion reactions from (a) to (g), in any order, as defined above.

More particularly, the dianilines of general formula (L) may be obtained, for example:
by reacting a 3,4-diaminophenol of formula (J) and a sulfonyl chloride of formula (B) (R1, R2 and R3 as defined in the general formula (IA) in the presence of a base such as aqueous sodium hydroxide or triethylamine in a solvent, for instance acetone, at a temperature in the region of 20° C.

The products of formula (J) may be obtained, for example,
by reduction in an autoclave of a 4-amino-3-nitrophenol of formula (IA) in the presence of hydrogen under an atmosphere of several bar, and of a catalyst, for instance palladium-on-charcoal, in a protic solvent such as methanol.
by reduction of a 4-amino-3-nitrobenzene sulfonate ester of formula (I), for example in the presence of iron powder and acetic acid, in a protic solvent such as methanol, at a temperature in the region of 65° C. The products of formula (I) may be obtained by reacting a 4-amino-3-nitrophenol of formula (H) and a sulfonyl chloride of formula (B) in the presence of a base such as aqueous sodium hydroxide or triethylamine in a solvent, for instance acetone, at a temperature in the region of 20° C.

More particularly, the benzimidazoles of general formula (Ia') may be obtained, for example:
by reacting an amine NHR4R5 (with R4 and R5 as defined above) with a carbamate of formula (M) in the presence of an aprotic solvent such as 1-methylpyrrolidin-2-one. The reaction is performed at a temperature ranging from 90° C. to 150° C. in a sealed microwave tube. The carbamates of formula (M) may be obtained especially as described in patent WO 03/028 721 A2, by cyclization of the products of formula (L) in the presence of a pseudothiourea of formula (K) in the presence of acetic acid and in a protic solvent such as methanol, at a temperature in the region of 65° C.

by reacting a urea of formula (O) and a sulfonyl chloride of formula (B) in the presence of a base such as aqueous sodium hydroxide or triethylamine in a solvent, for instance acetone, at a temperature in the region of 20° C.

The ureas of formula (O) may be obtained from carbamates of formula (N) in the presence of amines NHR4R5 and an aprotic solvent such as 1-methylpyrrolidin-2-one. The reaction is performed at a temperature ranging from 90° C. to 150° C. in a sealed microwave tube.

The carbamates of formula (N) may be prepared especially as described in patent WO 03/028 721 A2, starting with a 3,4-diaminophenol of formula (J) and a thiopseudourea of formula (K) in the presence of acetic acid and in a protic solvent such as methanol, at a temperature in the region of 65° C.

More particularly, the benzimidazoles of general formula (Ia) may be obtained, for example, by coupling a 2-aminobenzimidazole of formula (P) with an acid R'COOH for which R' has the meanings given above for R in which the potentially reactive functions are optionally protected.

The benzimidazoles of formula (Ia) may be obtained by coupling under the conditions described, for example, by Bach T. and al. (Synlett, 2002, (8), 1302-1304) in the presence of O-(7-azabenzotriazol-1-yl)-N,N,N',N'-tetramethyluronium hexafluorophosphate, in a solvent such as dimethylformamide and in the presence of a base such as diisopropylethylamine, at a temperature in the region of 20° C. The potentially reactive functions are then optionally deprotected under the standard conditions described by Greene and Wuts in Protective Group in Organic Synthesis, $3^{rd}$ edition, Wiley-Interscience, 1999. More particularly, when the protecting group is a tert-butoxycarbonyl (BOC), the deprotection may be performed, for example, with trifluoroacetic acid in dichloromethane.

The benzimidazoles of formula (P) may be obtained by deprotecting the benzimidazoles of formula (M) under the standard conditions described by Greene and Wuts in Protective Group in Organic Synthesis, $3^{rd}$ edition, Wiley-Interscience, 1999. More particularly, when the protecting group is a tert-butoxycarbonyl (BOC), the deprotection may be performed, for example, with trifluoroacetic acid in dichloromethane.

A subject of the present invention is thus a process, according to Scheme 2a above, for preparing the products of formulae (Ib) and (Ib') as defined above, characterized in that the compound of formula (D'):

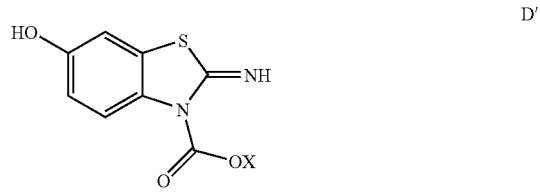

in which COOX represents an NH$_2$-protecting group,
is reacted with an amine of formula (G): H—NR4'R5' (G)
in which R4' and R5' have the meanings given above for R4 and R5 in which the potentially reactive functions are optionally protected,
to obtain a compound of formula (F):

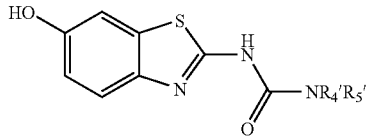
F in which R4' and R5' have the meanings given above,
which compound of formula F is reacted with the compound of formula (B) as defined above,
to obtain a product of formula (Ib):

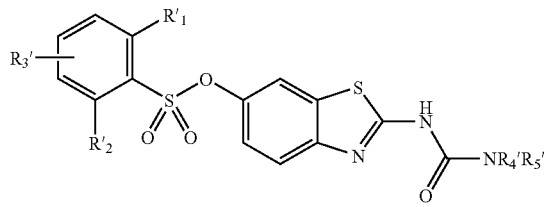
(Ib)

in which R1', R2', R3', R4' and R5' have the meanings given above.

The products of formula (Ib) and (Ib') may also be obtained by reacting the aminobenzothiazole of formula (C) with compounds of formula (B)

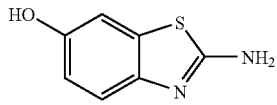
C to obtain products of formula (Q):

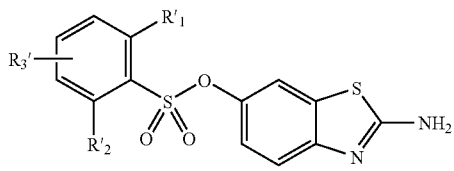
Q in which R1', R2' and R3' have the meanings given above.

The products of formula (Q) may then be reacted either:
with an acid of formula (G') or an acid chloride of formula (G") to obtain the products of formula (Ib')
with an aryl chloroformate to obtain the products of formula (R):

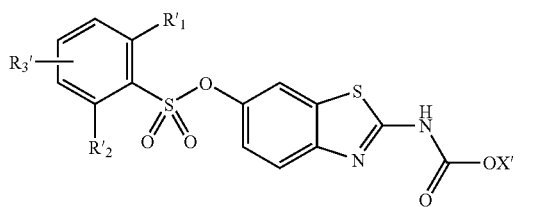
R in which COOX represents an NH$_2$-protecting group.

The products of formula (R) may then react with an amine of formula (G): H—NR4'R5' (G)) to obtain the products of formula (Ib)
in which R4' and R5' have the meanings given above.

The products of formulae (Ib) and (Ib') thus obtained, which may be products of formula (I) in which A represents S and which, in order to obtain products or other products of formula (I), may be subjected, if desired and if necessary, to one or more of the conversion reactions (a) to (g), in any order, as defined above.

In Scheme 2a above, the benzothiazoles of general formula (Ib) may be prepared from 2-aminobenzothiazol-6-ol (C).

The compounds of general formula (E') may be obtained by reacting an excess of alkyl chloroformate with the compound of formula (C), for example in the presence of a base such as pyridine, at a temperature in the region of 20° C.

More particularly, the ester derivatives of (6-hydroxybenzothiazol-2-yl)-carbamic acid of general formula (D') may be obtained, after treating the ester of 2-methoxycarbonylaminobenzothiazol-6-ylcarbonic acid (E') with, for example, an aqueous potassium hydroxide solution.

The compounds of general formula (F) may be obtained by reaction between the carbamic derivative of general formula (D') and an amine (G) in the presence of an aprotic solvent such as 1-methylpyrrolidin-2-one. The reaction may be performed at a temperature ranging from 90 to 150° C. in a sealed microwave tube.

The benzothiazoles of formula (Ib) may be obtained by reaction between the compounds of general formula (F) and a sulfonyl chloride of formula (B) (R1, R2 and R3 as defined in the general formula (I)) in the presence of a base such as aqueous sodium hydroxide or triethylamine, in a solvent, for instance acetone, at a temperature in the region of 20° C.

The benzothiazoles of formula (Ib) may also be obtained, for example, by reaction between a compound of general formula (R) and an amine (G) in the presence of a solvent such as tetrahydrofuran, at a temperature in the region of 20° C.

The benzothiazoles of formula (R) may be obtained by reaction between a compound of general formula (Q) and an excess of an aryl chloroformate in the presence of a base such as sodium hydrogen carbonate in a solvent such as tetrahydrofuran at a temperature in the region of 20° C.

The benzothiazoles of formula (Q) may be obtained by reacting 2-aminobenzothiazole of formula (C) and a sulfonyl chloride of formula (B) in the presence of a base such as aqueous sodium hydroxide or triethylamine, in a solvent, for instance acetone, at a temperature in the region of 20° C.

More particularly, the benzothiazoles of general formula (Ib') may be obtained, for example, by coupling a 2-aminobenzothiazole of formula (Q) with an acid R'COOH or by reaction with an acid chloride R'COCl for which R' has the meanings given above for R in which the potentially reactive functions may be optionally protected.

The benzothiazoles of general formula (Ib') may be obtained from 2-aminobenzothiazole of formula (Q):

by coupling under the conditions described, for example, by Bach T. and al. (Synlett, 2002, (8), 1302-1304) in the presence of O-(7-azabenzotriazol-1-yl)-N,N,N',N'-tetramethyluronium hexafluorophosphate, in a solvent such as dimethylformamide and in the presence of a base such as diisopropylethylamine at a temperature in the region of 20° C. The potentially reactive functions are then optionally deprotected under the standard conditions described by Greene and Wuts in Protective Group in Organic Synthesis, 3$^{rd}$ edition, Wiley-Interscience, 1999. More particularly, when the protecting group is a tert-butoxycarbonyl (BOC), the deprotection may be performed, for example, with trifluoroacetic acid in dichloromethane;

by reaction with an acid chloride R'COCl in the presence, for example, of a solvent such as pyridine at a temperature in the region of 20° C.

Among the starting materials of formulae B, G, G', G", H and K, some are known and may be obtained commercially: the starting materials may also be prepared according to the usual methods known to those skilled in the art, for example starting with commercial products.

The experimental section below gives examples of such starting materials.

Thus, the various reactive functions that certain compounds of the reactions defined above may bear may, if necessary, be protected with the appropriate protecting groups.

The following non-exhaustive list of examples of protection of reactive functions may be mentioned:

hydroxyl groups may be protected, for example, with alkyl radicals such as tert-butyl, trimethylsilyl, tert-butyldimethylsilyl, methoxymethyl, tetrahydropyranyl, benzyl or acetyl, the amino groups may be protected, for example, with acetyl, trityl, benzyl, tert-butoxycarbonyl, BOC, benzyloxycarbonyl, phthalimido or other radicals known in peptide chemistry.

The acid functions may be protected, for example, in the form of esters formed with readily cleavable esters such as benzyl or tert-butyl esters or esters known in peptide chemistry.

A list of various protecting groups that may be used will be found in the textbooks known to those skilled in the art and, for example, in patent BF 2 499 995.

The reactions a) to g) may be performed under the usual conditions known to those skilled in the art, for instance those indicated below.

a) The products described above may, if desired, undergo, on the possible carboxyl functions, esterification reactions that may be performed according to the usual methods known to those skilled in the art.

b) The possible conversions of ester functions to acid functions of the products described above may be performed, if desired, under the usual conditions known to those skilled in the art, especially by acid or alkaline hydrolysis, for example with sodium hydroxide or potassium hydroxide in alcoholic medium, for instance in methanol, or alternatively with hydrochloric acid or sulfuric acid.

The saponification reaction may be performed according to the usual methods known to those skilled in the art, for instance in a solvent such as methanol or ethanol, dioxane or dimethoxyethane, in the presence of sodium hydroxide or potassium hydroxide.

c) The possible free or esterified carboxyl functions in the products described above may be reduced, if desired, to alcohol functions via the methods known to those skilled in the art: the possible esterified carboxyl functions may be reduced, if desired, to alcohol functions via the methods known to those skilled in the art and especially with lithium aluminium hydride in a solvent, for instance tetrahydrofuran, dioxane or ethyl ether.

The possible free carboxyl functions in the products described above may be reduced, if desired, to alcohol functions especially with boron hydride.

d) The possible alkoxy functions especially such as methoxy in the products described above may be converted, if desired, into hydroxyl functions under the usual conditions known to those skilled in the art, for example with boron tribromide in a solvent such as, for example, methylene chloride, with pyridine hydrochloride or hydrobromide, or alternatively with hydrobromic or hydrochloric acid in water or trifluoroacetic acid at reflux.

e) The removal of protecting groups, for instance those indicated above, may be performed under the usual conditions known to those skilled in the art, especially via an acid hydrolysis performed with an acid such as hydrochloric acid, benzenesulfonic or para-toluenesulfonic acid, formic acid or trifluoroacetic acid, or alternatively via catalytic hydrogenation.

The phthalimido group may be removed with hydrazine.

f) The products described above may undergo, if desired, salification reactions, for example with a mineral or organic acid or with a mineral or organic base according to the usual methods known to those skilled in the art: such a salification reaction may be performed, for example, in the presence of hydrochloric acid, or alternatively of tartaric acid, citric acid or methanesulfonic acid, in an alcohol, for instance ethanol or methanol.

g) The possible optically active forms of the products described above may be prepared by resolution of the racemic mixtures according to the usual methods known to those skilled in the art.

The products of formula (I) as defined above and the acid-addition salts thereof show advantageous pharmacological properties especially on account of their kinase-inhibiting properties as indicated above.

The products of the present invention are especially useful for treating tumours.

The products of the invention may thus also increase the therapeutic effects of commonly used anti-tumoral agents.

These properties justify their therapeutic use, and a subject of the invention is particularly, as medicaments, the products of formula (I) as defined above, the said products of formula (I) being in any possible racemic, enantiomeric or diastereoisomeric isomer form, and also the addition salts with pharmaceutically acceptable mineral and organic acids or with pharmaceutically acceptable mineral and organic bases of the said products of formula (I).

A subject of the invention is most particularly, as medicaments, products corresponding to the following formulae:

2-({[2-(4-benzylpiperazin-1-yl)ethyl]carbamoyl}amino)-1,3-benzothiazol-6-yl 2,6-dichlorobenzenesulfonate 2-{[(3-morpholin-4-ylpropyl)carbamoyl]amino}-1,3-benzothiazol-6-yl 2,6-dichlorobenzenesulfonate 2-{[(2-pyrrolidin-1-ylethyl)carbamoyl]amino}-1,3-benzothiazol-6-yl 2,6-dichlorobenzenesulfonate 2-{[(3-pyrrolidin-1-ylpropyl)carbamoyl]amino}-1,3-benzothiazol-6-yl 2,6-dichlorobenzenesulfonate 2-({[2-(4-methylpiperazin-1-yl)ethyl]carbamoyl}amino)-1,3-benzothiazol-6-yl 2,6-dichlorobenzenesulfonate 2-({[2-(1-methylpyrrolidin-2-yl)ethyl]carbamoyl}amino)-1,3-benzothiazol-6-yl 2,6-dichlorobenzenesulfonate 2-({[3-(dimethylamino)propyl]carbamoyl}amino)-1,3-benzothiazol-6-yl 2,6-dichlorobenzenesulfonate
2-({[2-(2,6-dimethylpiperidin-1-yl)ethyl]carbamoyl}amino)-1,3-benzothiazol-6-yl 2,6-dichlorobenzenesulfonate
2-{[(2-piperidin-1-ylethyl)carbamoyl]amino}-1,3-benzothiazol-6-yl 2,6-dichlorobenzenesulfonate
2-({[3-(2-oxopyrrolidin-1-yl)propyl]carbamoyl}amino)-1,3-benzothiazol-6-yl 2,6-dichlorobenzenesulfonate
2-({[3-(4-benzylpiperazin-1-yl)propyl]carbamoyl}amino)-1,3-benzothiazol-6-yl 2,6-dichlorobenzenesulfonate
2-({[3-(4-methylpiperazin-1-yl)propyl]carbamoyl}amino)-1,3-benzothiazol-6-yl 2,6-dichlorobenzenesulfonate
2-[(methylcarbamoyl)amino]-1,3-benzothiazol-6-yl 2,6-dichlorobenzenesulfonate
2-{[(2-azepan-1-ylethyl)carbamoyl]amino}-1,3-benzothiazol-6-yl 2,6-dichlorobenzenesulfonate
and also the addition salts with pharmaceutically acceptable mineral and organic acids or with pharmaceutically acceptable mineral and organic bases of the said products of formula (I).

A subject of the invention is most particularly, as medicaments, products corresponding to the following formulae:
2-{[(2-methoxyethyl)carbamoyl]amino}-1H-benzimidazol-5-yl 2,6-dichlorobenzenesulfonate
2-{[(2-methoxyethyl)carbamoyl]amino}-1H-benzimidazol-5-yl 2-chloro-6-methylbenzenesulfonate
2-{[(2-methoxyethyl)carbamoyl]amino}-1H-benzimidazol-5-yl 2,4,6-trimethylbenzenesulfonate
2-{[(2-methoxyethyl)carbamoyl]amino}-1H-benzimidazol-5-yl 2,6-dichloro-4-(trifluoromethyl)benzenesulfonate
2-{[(2-morpholin-4-ylethyl)carbamoyl]amino}-1H-benzimidazol-5-yl 2,6-dichlorobenzenesulfonate
2-{[(2-morpholin-4-ylethyl)carbamoyl]amino}-1,3-benzothiazol-6-yl 2,6-dichlorobenzenesulfonate
2-{[(2-morpholin-4-ylethyl)carbamoyl]amino}-1,3-benzothiazol-6-yl 2,6-difluorobenzenesulfonate
2-{[(2-methoxyethyl)carbamoyl]amino}-1,3-benzothiazol-6-yl 2,6-difluorobenzenesulfonate
and also the addition salts with pharmaceutically acceptable mineral and organic acids or with pharmaceutically acceptable mineral and organic bases of the said products of formula (I).

A subject of the invention is most particularly, as medicaments, products corresponding to the following formulae:
2-{[(2-methoxyethyl)carbamoyl]amino}-1H-benzimidazol-5-yl 2,6-dichlorobenzenesulfonate
2-{[(2-methoxyethyl)carbamoyl]amino}-1H-benzimidazol-5-yl 2-chloro-6-methylbenzenesulfonate
2-{[(2-methoxyethyl)carbamoyl]amino}-1H-benzimidazol-5-yl 2,6-dichloro-4-(trifluoromethyl)benzenesulfonate
2-{[(2-morpholin-4-ylethyl)carbamoyl]amino}-1H-benzimidazol-5-yl 2,6-dichlorobenzenesulfonate
2-{[(2-morpholin-4-ylethyl)carbamoyl]amino}-1,3-benzothiazol-6-yl 2,6-dichlorobenzenesulfonate
2-({[2-(4-benzylpiperazin-1-yl)ethyl]carbamoyl}amino)-1,3-benzothiazol-6-yl 2,6-dichlorobenzenesulfonate
2-{[(3-morpholin-4-ylpropyl)carbamoyl]amino}-1,3-benzothiazol-6-yl 2,6-dichlorobenzenesulfonate
2-{[(3-pyrrolidin-1-ylpropyl)carbamoyl]amino}-1,3-benzothiazol-6-yl 2,6-dichlorobenzenesulfonate
2-({[2-(4-methylpiperazin-1-yl)ethyl]carbamoyl}amino)-1,3-benzothiazol-6-yl 2,6-dichlorobenzenesulfonate
2-({[2-(1-methylpyrrolidin-2-yl)ethyl]carbamoyl}amino)-1,3-benzothiazol-6-yl 2,6-dichlorobenzenesulfonate
2-({[3-(dimethylamino)propyl]carbamoyl}amino)-1,3-benzothiazol-6-yl 2,6-dichlorobenzenesulfonate
2-{[(2-azepan-1-ylethyl)carbamoyl]amino}-1,3-benzothiazol-6-yl 2,6-dichlorobenzenesulfonate
and also the addition salts with pharmaceutically acceptable mineral and organic acids or with pharmaceutically acceptable mineral and organic bases of the said products of formula (I).

A subject of the invention is most particularly, as medicaments, products corresponding to the following formulae:
2-{[(2-methoxyethyl)carbamoyl]amino}-1H-benzimidazol-5-yl 2,6-dichlorobenzenesulfonate
2-{[(2-methoxyethyl)carbamoyl]amino}-1H-benzimidazol-5-yl 2-chloro-6-methylbenzenesulfonate
2-{[(2-methoxyethyl)carbamoyl]amino}-1H-benzimidazol-5-yl 2,6-dichloro-4-(trifluoromethyl)benzenesulfonate
2-{[(2-morpholin-4-ylethyl)carbamoyl]amino}-1H-benzimidazol-5-yl 2,6-dichlorobenzenesulfonate
2-({[2-(4-benzylpiperazin-1-yl)ethyl]carbamoyl}amino)-1,3-benzothiazol-6-yl 2,6-dichlorobenzenesulfonate
2-{[(3-morpholin-4-ylpropyl)carbamoyl]amino}-1,3-benzothiazol-6-yl 2,6-dichlorobenzenesulfonate
2-{[(3-pyrrolidin-1-ylpropyl)carbamoyl]amino}-1,3-benzothiazol-6-yl 2,6-dichlorobenzenesulfonate
2-({[2-(4-methylpiperazin-1-yl)ethyl]carbamoyl}amino)-1,3-benzothiazol-6-yl 2,6-dichlorobenzenesulfonate
2-({[2-(1-methylpyrrolidin-2-yl)ethyl]carbamoyl}amino)-1,3-benzothiazol-6-yl 2,6-dichlorobenzenesulfonate
2-({[3-(dimethylamino)propyl]carbamoyl}amino)-1,3-benzothiazol-6-yl 2,6-dichlorobenzenesulfonate
and also the addition salts with pharmaceutically acceptable mineral and organic acids or with pharmaceutically acceptable mineral and organic bases of the said products of formula (I).

A subject of the invention is most particularly, as medicaments, products corresponding to the following formulae:
2-[3(2-morpholin-4-yl-ethyl)ureido]benzothiazol-6-yl 2,6-dichloro-benzenesulfonate
2-({[2-(4-benzylpiperazin-1-yl)ethyl]carbamoyl}amino)-1,3-benzothiazol-6-yl 2,6-dichlorobenzenesulfonate
2-{[(3-morpholin-4-ylpropyl)carbamoyl]amino}-1,3-benzothiazol-6-yl 2,6-dichlorobenzenesulfonate
2-{[(3-pyrrolidin-1-ylpropyl)carbamoyl]amino}-1,3-benzothiazol-6-yl 2,6-dichlorobenzenesulfonate
and also the addition salts with pharmaceutically acceptable mineral and organic acids or with pharmaceutically acceptable mineral and organic bases of the said product of formula (I).

The invention also relates to pharmaceutical compositions containing as active principle at least one of the products of formula (I) as defined above or a pharmaceutically acceptable salt of this product, or a prodrug of this product and, where appropriate, a pharmaceutically acceptable support.

The invention thus covers pharmaceutical compositions containing as active principle at least one of the medicaments as defined above.

Such pharmaceutical compositions of the present invention may also, where appropriate, contain active principles of other antimitotic medicaments, especially such as those based on taxol, cis-platin, DNA intercalating agents and the like.

These pharmaceutical compositions may be administered via the buccal route, via the parenteral route or via the local route by topical application to the skin and mucous membranes or by intravenous or intramuscular injection.

These compositions may be solid or liquid and may be in any pharmaceutical form commonly used in human medicine, for instance simple or sugar-coated tablets, pills, lozenges, gel capsules, drops, granules, injectable preparations, pomades, creams or gels; they are prepared according to the usual methods. The active principle may be incorporated therein into excipients usually used in these pharmaceutical compositions, such as talc, gum arabic, lactose, starch, magnesium stearate, cocoa butter, aqueous or non-aqueous vehicles, fatty substances of animal or plant origin, paraffinic derivatives, glycols, various wetting agents, dispersants or emulsifiers, and preserving agents.

The usual dosage, which is variable depending on the product used, the individual treated and the complaint under consideration, may be, for example, from 0.05 to 5 g per day per adult, or preferably from 0.1 to 2 g per day.

A subject of the present invention is also the use of the products of formula (I) as defined above or of pharmaceutically acceptable salts of these products for the preparation of a medicament for inhibiting the activity of a protein kinase.

A subject of the present invention is also the use of products of formula (I) as defined above for the preparation of a medicament for treating or preventing a disease characterized by deregulation of the activity of a protein kinase.

Such a medicament may especially be intended for treating or preventing a disease in a mammal.

A subject of the present invention is also the use defined above, in which the protein kinase is a protein tyrosine kinase.

A subject of the present invention is also the use defined above, in which the protein kinase is chosen from the following group:

AuroraA, AuroraB, members of the family of CDKs (CDK1,2,4,5,7,9), RON, Tie2, members of the family of VEGFRs (VEGFR1 or fit-1, VEGFR2 or KDR or flk-1, VEGFR3), FGFRs (FGFR1, FGFR2, FGFR3, FGFR4, FGFR5), MET and also mutants of the protein MET, EGFR, Fak, IGF-1R or PDGFR.

A subject of the present invention is also particularly the use defined above, in which the protein kinase is MET.

A subject of the present invention is also the use defined above, in which the protein kinase is in a cell culture.

A subject of the present invention is also the use defined above, in which the protein kinase is in a mammal.

A subject of the present invention is especially the use of a product of formula (I) as defined above for the preparation of a medicament for preventing or treating diseases associated with an uncontrolled proliferation.

A subject of the present invention is particularly the use of a product of formula (I) as defined above for the preparation of a medicament for treating or preventing a disease chosen from the following group: blood vessel proliferation disorders, fibrotic disorders, "mesangial" cell proliferation disorders, metabolic disorders, allergies, asthma, thrombosis, nervous system diseases, retinopathy, psoriasis, rheumatoid arthritis, diabetes, muscle degeneration and cancers.

A subject of the present invention is more particularly the use of a product of formula (I) as defined above for the preparation of a medicament for treating or preventing a disease chosen from the following group: blood vessel proliferation disorders, fibrotic disorders, "mesangial" cell proliferation disorders, retinopathy, psoriasis, rheumatoid arthritis, diabetes, muscle degeneration and cancers.

A subject of the present invention is thus most particularly the use of a product of formula (I) as defined above for the preparation of a medicament for treating or preventing diseases in oncology and especially for treating cancers.

Among these cancers, the treatment of solid or liquid tumours and the treatment of cancers that are resistant to cytotoxic agents are of interest.

The cited products of the present invention may especially be used for treating primary tumours and/or metastases, in particular in gastric, hepatic, renal, ovarian, colon, prostate and lung (NSCLC and SCLC) cancers, glioblastomas, thyroid, bladder or breast cancers, in melanomas, in myeloid or lymphoid haematopoietic tumours, in sarcomas, in brain, larynx or lymphatic system cancers and bone and pancreatic cancers.

A subject of the present invention is also the use of products of formula (I) as defined above for the preparation of medicaments for cancer chemotherapy.

Such medicaments for cancer chemotherapy may be used alone or in combination.

The products of the present patent application may especially be administered alone or in combination with chemotherapy or radiotherapy or alternatively in combination, for example, with other therapeutic agents.

Such therapeutic agents may be commonly used antitumoral agents.

Kinase inhibitors that may be mentioned include butyrolactone, flavopiridol and 2-(2-hydroxyethylamino)-6-benzylamino-9-methylpurine, also known as olomucine.

The examples that follow, which are products of formula (I), illustrate the invention without, however, limiting it.

EXPERIMENTAL SECTION

Microwave Oven Used:
Biotage, Initiator EXP-EU, 300 W max, 2450 MHz

Unless otherwise indicated, the $^1$H NMR spectra at 500 MHz, the $^1$H NMR spectra at 400 MHz and $^1$H NMR spectra at 300 MHz were acquired on a Bruker Avance DRX-500, Bruker Avance DRX-400 or Bruker Avance DPX-300 spectrometer, respectively, with the chemical shifts (δ in ppm) in the solvent d6-dimethyl sulfoxide (d6-DMSO) referenced to 2.5 ppm at a temperature of 303 K for the DRX-300 and 400, and 298 K for the DRX-500.

The mass spectra were acquired either by electron impact (EI; 70 eV; Finnigan SSQ7000 machine) or by chemical ionization (Cl; reactant gas: ammonia; Finnigan SSQ7000 machine). The electrospray (ES$^+$) spectra were acquired on a Platform II (Micromass) machine.

Example 1

2-{[(2-methoxyethyl)carbamoyl]amino}-1H-benzimidazol-5-yl 2,6-dichlorobenzenesulfonate 2-{[(2-Methoxyethyl)carbamoyl]amino}-1H-benzimidazol-5-yl 2,6-dichlorobenzenesulfonate may be prepared in the following manner:

To a solution of 175 mg of 1-(5-hydroxy-1H-benzimidazol-2-yl)-3-(2-methoxyethyl)urea in 15 cm$^3$ of 0.1N aqueous sodium hydroxide solution are added 189 mg of finely ground 2,6-dichlorobenzenesulfonyl chloride. The suspension is stirred for about 20 hours at a temperature in the region of 20° C., 10 cm$^3$ of water are then added and the mixture is cooled to about 5° C. for about 15 minutes. The precipitate is filtered off by suction, washed with three times 2 cm$^3$ of water and dried under reduced pressure (13 kPa) over phosphorus pentoxide. After flash chromatography on a column of silica [eluent: dichloromethane/methanol/acetonitrile (95/3/2 by volume)], 65 mg of 2-{[(2-methoxyethyl)carbamoyl]amino}-1H-benzimidazol-5-yl 2,6-dichlorobenzenesulfonate are obtained in the form of a cream-coloured powder, the characteristics of which are as follows:

Melting point: melting at 171° C. (Köfler block)

$^1$H NMR spectrum at 400 MHz: 3.28 (s, 3H); 3.34 (partially masked m, 2H); 3.42 (t, J=5.5 Hz, 2H); 6.75 (broad d, J=8.5 Hz, 1H); from 6.95 to 7.22 (broad m, 2H); 7.30 (broad m, 1H); from 7.68 to 7.79 (m, 3H); 9.93 (broad m, 1H); 11.75 (broad m, 1H).

Mass spectrum: LCMS: m/z 459: [M+H]+ (base peak), m/z 917: [2M+H]+, m/z 384: [M+H]+. NHC2H4OCH3

1-(5-Hydroxy-1H-benzimidazol-2-yl)-3-(2-methoxyethyl)urea is prepared as described in patent WO 03/028 721 A2.

Example 2

2-{[(2-Methoxyethyl)carbamoyl]amino}-1H-benzimidazol-5-yl 2-chloro-6-methylbenzenesulfonate 2-{[(2-Methoxyethyl)carbamoyl]amino}-1H-benzimidazol-5-yl 2-chloro-6-methylbenzenesulfonate may be prepared as in Example 1, but starting with 175 mg of 1-(5-hydroxy-1H-benzimidazol-2-yl)-3-(2-methoxyethyl)urea, 17.5 cm$^3$ of aqueous 0.1N sodium hydroxide solution and 173 mg of 2-chloro-6-methyl-benzenesulfonyl chloride. After flash chromatography on a column of silica [eluent: dichloromethane/methanol (96/4 by volume)], 45 mg of 2-{[(2-methoxyethyl)carbamoyl]amino}-1H-benzimidazol-5-yl 2-chloro-6-methylbenzenesulfonate are obtained in the form of a solid, the characteristics of which are as follows:

Melting point: melting at 138° C. (Köfler block)

$^1$H NMR spectrum at 400 MHz: 2.42 (s, 3H); 3.28 (s, 3H); 3.33 (partially masked m, 2H); 3.41 (t, J=5.5 Hz, 2H); 6.70 (dd, J=2.5 and 8.5 Hz, 1H); from 6.91 to 7.31 (broad m, 2H); 7.27 (broad d J=8.5 Hz, 1H); 7.40 (broad d, J=8.0 Hz, 1H); 7.60 (t, J=8.0 Hz, 1H); 7.66 (broad d, J=8.0 Hz, 1H); 9.90 (broad m, 1H); 11.75 (broad m, 1H).

Mass spectrum: LCMS: m/z 439: [M+H]+

CI: m/z 439: [M+H]+

Example 3

2-{[(2-Methoxyethyl)carbamoyl]amino}-1H-benzimidazol-5-yl 2,4,6-trimethylbenzenesulfonate 2-{[(2-Methoxyethyl)carbamoyl]amino}-1H-benzimidazol-5-yl 2,4,6-trimethylbenzenesulfonate may be prepared in the following manner:

To a suspension of 200 mg of 1-(5-hydroxy-1H-benzimidazol-2-yl)-3-(2-methoxyethyl)urea in 50 cm$^3$ of acetone are added 0.162 cm$^3$ of triethylamine and 192 mg of 2,4,6-trimethylbenzenesulfonyl chloride. After stirring for about 20 hours at a temperature in the region of 20° C., 95 mg of 2,4,6-trimethylbenzenesulfonyl chloride and 0.08 cm$^3$ of triethylamine are added. After stirring for a further 3 hours at the same temperature, 95 mg of 2,4,6-trimethylbenzenesulfonyl chloride are added and the suspension is stirred for about 20 hours. After concentrating to dryness under reduced pressure (13 kPa), the residue is taken up in 50 cm$^3$ of water and extracted with three times 40 cm$^3$ of ethyl acetate. The organic phases are dried over magnesium sulfate, filtered and concentrated under reduced pressure. After flash chromatography on a column of silica [eluent: dichloromethane/methanol (95/5 by volume)], 134 mg of a resin are obtained, which resin is solidified in 7 cm$^3$ of diisopropyl ether and 7 cm$^3$ of diethyl ether. After filtration and drying under reduced pressure (13 kPa) over phosphorus pentoxide, 123 mg of 2-{[(2-methoxyethyl)carbamoyl]amino}-1H-benzimidazol-5-yl 2,4,6-trimethylbenzenesulfonate are obtained in the form of a solid, the characteristics of which are as follows:

Melting point: melting at 140° C. then 162° C. (Köfler block)

$^1$H NMR spectrum at 300 MHz: 2.29 (s, 3H); 2.44 (s, 6H); from 3.22 to 3.39 (partially masked m, 5H); 3.42 (t, J=5.5 Hz, 2H); 6.60 (dd, J=2.5 and 8.5 Hz, 1H); 6.93 (broad m, 1H); 7.12 (s, 2H); 7.25 (broad d, J=8.5 Hz, 2H); 9.90 (broad m, 1H); 11.75 (broad m, 1H)

Mass spectrum: LCMS: m/z 433: [M+H]+ (base peak) m/z 865: [2M+H]+, m/z 431: [M−H]−, m/z 863: [2M−H]

Example 4

2-{[(2-Methoxyethyl)carbamoyl]amino}-1H-benzimidazol-5-yl 2,6-dichloro-4-(trifluoromethyl)benzenesulfonate 2-{[(2-Methoxyethyl)carbamoyl]amino}-1H-benzimidazol-5-yl 2,6-dichloro-4-(trifluoromethyl)benzenesulfonate may be prepared as in Example 1, but starting with 200 mg of 1-(5-hydroxy-1H-benzimidazol-2-yl)-3-(2-methoxyethyl) urea, 16 cm$^3$ of aqueous 0.1N sodium hydroxide solution and 276 mg of 2,6-dichloro-4-trifluoromethylbenzenesulfonyl chloride. After flash chromatography on a column of silica [eluent: dichloromethane/methanol (95/5 by volume)], 45 mg of 2-{[(2-methoxyethyl)carbamoyl]amino}-1H-benzimidazol-5-yl 2,6-dichloro-4-(trifluoromethyl)benzenesulfonate are obtained in the form of a resin, the characteristics of which are as follows:

Rf TLC silica=0.15 [eluent: dichloromethane/methanol (95/5 by volume)

$^1$H NMR spectrum at 400 MHz: 3.29 (s, 3H); 3.33 (partially masked m, 2H); 3.42 (t, J=5.5 Hz, 2H); 6.79 (broad m, 1H); from 7.06 to 7.20 (broad m, 2H); 7.32 (broad m, 1H); 8.23 (s, 2H); 9.95 (broad m, 1H); from 11.7 to 11.8 (broad m, 1H)

Mass spectrum: LCMS: m/z 527 [M+H]+ (base peak), m/z 1053: [2M+H]+, m/z 525: [M−H]−, m/z 1051: [2M−H]− (base peak).

Example 5

2-{[(2-Morpholin-4-ylethyl)carbamoyl]amino}-1H-benzimidazol-5-yl 2,6-dichlorobenzenesulfonate 2-{[(2-Morpholin-4-ylethyl)carbamoyl]amino}-1H-benzimidazol-5-yl 2,6-dichlorobenzenesulfonate may be prepared as in Example 1, but starting with 250 mg of 1-(5-hydroxy-1H-benzimidazol-2-yl)-3-(2-morpholin-4-ylethyl) urea, 20.5 cm$^3$ of aqueous 0.1N sodium hydroxide solution and 221 mg of 2,6-dichlorobenzenesulfonyl chloride. After flash chromatography on a column of silica [eluent: dichloromethane/methanol (92/8 by volume)], 114 mg of 2-{[(2-morpholin-4-ylethyl)carbamoyl]amino}-1H-benzimidazol-5-yl 2,6-dichlorobenzenesulfonate are obtained in the form of a white powder, the characteristics of which are as follows:

Melting point: melting at 149° C. (Köfler block)

$^1$H NMR spectrum at 400 MHz: from 2.33 to 2.46 (m, 6H); from 3.22 to 3.38 (masked m, 2H); 3.60 (m, 4H); 6.75 (dd, J=2.5 and 8.5 Hz, 1H); 7.08 (broad m, 1H); 7.29 (broad d, J=8.5 Hz, 2H); from 7.67 to 7.79 (m, 3H); 10.0 (broad m, 1H); 11.75 (broad m, 1H)

Mass spectrum: LCMS: m/z 514: [M+H]+, m/z 512: [M−H]−

EI: m/z 100 (base peak): C4H8NO—CH2+, m/z 146: C6H3Cl2

1-(5-Hydroxy-1H-benzimidazol-2-yl)-3-(2-morpholin-4-ylethyl)urea is prepared as described in patent WO 03/028 721 A2.

Example 6

2-{[(2-Morpholin-4-ylethyl)carbamoyl]amino}-1,3-benzothiazol-6-yl 2,6-dichlorobenzenesulfonate a) 2-{[(2-Morpholin-4-yl ethyl)carbamoyl]amino}-1,3-benzothiazol-6-yl 2,6-dichlorobenzenesulfonate may be prepared in the following manner:

To a solution of 260 mg of 1-(6-hydroxy-1,3-benzothiazol-2-yl)-3-(2-morpholin-4-ylethyl)urea in 19.4 cm³ of aqueous 0.1N sodium hydroxide solution are added 209 mg of finely ground 2,6-dichlorobenzenesulfonyl chloride. After stirring for about 5 hours at a temperature in the region of 20° C., a further 70 mg of 2,6-dichlorobenzenesulfonyl chloride are added. After stirring for about 18 hours at the same temperature, the reaction mixture is concentrated under reduced pressure (13 kPa) to a volume of about 5 cm³. The suspension obtained is cooled for about one hour at a temperature in the region of 5° C. The solid is filtered off by suction, washed with three times 2 cm³ of water precooled to about 5° C., and dried under reduced pressure (13 kPa) over phosphorus pentoxide. 216 mg of 2-{[(2-morpholin-4-ylethyl)carbamoyl]amino}-1,3-benzothiazol-6-yl 2,6-dichlorobenzenesulfonate are thus obtained in the form of a cream-coloured powder, the characteristics of which are as follows:

Melting point: melting at 130 to 135° C. (Köfler block)

¹H NMR spectrum at 300 MHz: from 2.33 to 2.47 (m, 6H); from 3.22 to 3.38 (masked m, 2H); 3.59 (m, 4H); 6.79 (broad t, J=5.5 Hz, 1H); 7.01 (dd, J=2.5 and 9.0 Hz, 1H); 7.56 (d, J=9.0 Hz, 1H); from 7.69 to 7.81 (m, 4H); 10.95 (broad m, 1H)

Mass spectrum: LCMS: m/z 531: [M+H]+, m/z 529: [M−H]− b) 1-(6-Hydroxy-1,3-benzothiazol-2-yl)-3-(2-morpholin-4-ylethyl)urea 1-(6-Hydroxy-1,3-benzothiazol-2-yl)-3-(2-morpholin-4-ylethyl)urea may be prepared in the following manner:

In a 10 cm³ tube, 200 mg of methyl(6-hydroxy-1,3-benzothiazol-2-yl)carbamate are suspended in 6 cm³ of 1-methyl-pyrrolidin-2-one, and 580 mg of 2-morpholin-4-ylethylamine are added. After closing, the tube is placed in the microwave oven at a temperature in the region of 150° C. for about 25 minutes. After concentrating to dryness under reduced pressure, the residue obtained is purified by flash chromatography on a column of silica [eluent: dichloromethane/methanol (95/5 by volume)]. 270 mg of 1-(6-hydroxy-1,3-benzothiazol-2-yl)-3-(2-morpholin-4-ylethyl)urea are thus obtained in the form of a resin, the characteristics of which are as follows:

Rf TLC silica=0.23 [eluent: dichloromethane/methanol (90/10 by volume)]

Mass spectrum: EI: m/z 322 [M+.], m/z 100 (base peak): C4H8NO—CH2+ m/z 166: [M+.]− CONH(CH2)2-morpholine.

LCMS: m/z 323 [M+H]+ (base peak), m/z 167: [M+H]+. CONH(CH2)2-C4H8NO m/z 157: C4H8NO(CH2)2NHCO+-morpholine, m/z 321: [M−H]-m/z 643: [2M−H c) Methyl(6-hydroxy-1,3-benzothiazol-2-yl)carbamate Methyl(6-hydroxy-1,3-benzothiazol-2-yl)carbamate may be prepared in the following manner:

To a solution of 3 g of 2-amino-1,3-benzothiazol-6-ol in 50 cm³ of pyridine are added dropwise, while maintaining the temperature in the region of 25° C., 1.7 g of methyl chloroformate. After stirring for about 3 hours after the end of the addition in the region of 25° C., 0.37 g of methyl chloroformate is added. After stirring for 18 hours at the same temperature, a further 1.7 g of methyl chloroformate are added and the mixture is stirred for a further 2 hours. The reaction mixture is poured into 100 cm³ of water and stirred for about 15 minutes. The precipitate is filtered off by suction, washed with three times 30 cm³ of water and dried under reduced pressure (13 kPa) over phosphorus pentoxide.

3.5 g of a mixture of methyl 2-[(methoxycarbonyl)amino]-1,3-benzothiazol-6-yl carbonate and methyl(6-hydroxy-1,3-benzothiazol-2-yl)carbamate are thus obtained, the characteristics of which are as follows:

Mass spectrum: LCMS: m/z 225: [M+H]+ (base peak), m/z 193: [M+H]+—OCH3

+50% disubstituted: m/z 283: [M+H]+ (base peak), m/z 251: MH+—OCH3

This mixture is dissolved in 140 cm³ of aqueous 5N potassium hydroxide solution and stirred at a temperature in the region of 20° C. for about 18 hours, and is then cooled to about 5° C. After adjusting the pH to about 5-6 by addition of glacial acetic acid, the suspension obtained is maintained in the region of 0° C. for about 30 minutes. The solid is filtered off by suction, washed with three times 5 cm³ of water precooled to about 5° C. and dried under reduced pressure (13 kPa) over phosphorus pentoxide. 2.66 g of methyl(6-hydroxy-1,3-benzothiazol-2-yl)carbamate are thus obtained in the form of a pink powder, the characteristics of which are as follows:

Melting point: melting at 256° C. (Köfler block)

¹H NMR spectrum at 400 MHz: 3.74 (s, 3H); 6.83 (dd, J=2.5 and 9.0 Hz, 1H); 7.24 (d, J=2.5 Hz, 1H); 7.47 (d, J=8.5 Hz, 1H); 9.46 (broad s, 1H); 11.3 (broad m, 1H)

Mass spectrum: EI: m/z 224: [M+.](base peak), m/z 192: [M+H]+—OCH3 d) 2-Amino-1,3-benzothiazol-6-ol

2-Amino-1,3-benzothiazol-6-ol may be prepared in the following manner:

To a solution of 7 g of 6-ethoxy-1,3-benzothiazol-2-amine (commercial) in 65 cm³ of glacial acetic acid are added 130 cm³ of a 48% solution of hydrobromic acid in water. The solution is refluxed for about 20 hours. After concentrating to dryness under reduced pressure (13 kPa), the residue is taken up in 50 cm³ of water and the pH of the solution is brought to about 8 by addition of solid sodium hydrogen carbonate. The mixture is extracted with four times 250 cm³ of ethyl acetate and the combined organic phases are washed with three times 20 cm³ of saturated aqueous sodium chloride solution, dried over magnesium sulfate, filtered and concentrated to dryness under reduced pressure (13 kPa). The solid obtained is taken up in 20 cm³ of dichloromethane, filtered off by suction, washed with three times 10 cm³ of dichloromethane and then three times 20 cm³ of diethyl ether, and dried under reduced pressure (13 kPa) over phosphorus pentoxide. 5.3 g of 2-amino-1,3-benzothiazol-6-ol are thus obtained in the form of a pink powder, the characteristics of which are as follows:

Melting point: melting at 235-240° C. (Köfler block)

¹H NMR spectrum at 300 MHz: 6.64 (dd, J=2.5 and 9.0 Hz, 1H); 7.01 (d, J=2.5 Hz, 1H); 7.05 (broad s, 2H); 7.12 (d, J=8.5 Hz, 1H); 9.07 (broad s, 1H)

Mass spectrum: IE: m/z 166: [M+.](base peak)

Example 7

2-{[(2-Morpholin-4-ylethyl)carbamoyl]amino}-1,3-benzothiazol-6-yl 2,6-difluorobenzenesulfonate

2-{[(2-Morpholin-4-ylethyl)carbamoyl]amino}-1,3-benzothiazol-6-yl 2,6-difluorobenzenesulfonate may be prepared as in Example 6a), but starting with 330 mg of 1-(6-hydroxy-1,3-benzothiazol-2-yl)-3-(2-methoxyethyl)urea and 239 mg of 2,6-dichlorobenzenesulfonyl chloride in 25.6 cm³ of aqueous 0.1N sodium hydroxide solution. After flash chromatography on a column of silica [eluent: dichloromethane/methanol (94/6 by volume)], 460 mg of 2-{[(2-morpholin-4-ylethyl)carbamoyl]amino}-1,3-benzothiazol-6-yl 2,6-difluorobenzenesulfonate are obtained in the form of a white powder, the characteristics of which are as follows:

Melting point: melting at 195° C. (Köfler block)

¹H NMR spectrum at 400 MHz: 2.41 (m, 6H); 3.27 (partially masked m, 2H); 3.59 (m, 4H); 6.76 (broad t, J=5.5 Hz, 1H); 7.05 (dd, J=2.5 and 9.0 Hz, 1H); 7.42 (broad t, J=9.0 Hz, 2H); 7.57 (d, J=9.0 Hz, 1H); 7.79 (d, J=2.5 Hz, 1H); 7.93 (tt, J=6.0 and 9.0 Hz, 1H); 10.9 (broad m, 1H).

Example 8

2-{[(2-Methoxyethyl)carbamoyl]amino}-1,3-benzothiazol-6-yl 2,6-difluorobenzenesulfonate a) 2-{[(2-Methoxyethyl)carbamoyl]amino}-1,3-benzothiazol-6-yl 2,6-difluorobenzenesulfonate may be prepared as in Example 6a), but starting with 300 mg of 1-(6-hydroxy-1,3-benzothiazol-2-yl)-3-(2-methoxyethyl)urea and 262 mg of 2,6-dichlorobenzenesulfonyl chloride in 28 cm³ of aqueous 0.1N sodium hydroxide solution. After flash chromatography on a column of silica [eluent: dichloromethane/methanol (95/5 by volume)], 331 mg of 2-{[(2-methoxyethyl)carbamoyl]amino}-1,3-benzothiazol-6-yl 2,6-difluorobenzenesulfonate in the form of a beige-coloured resin, the characteristics of which are as follows:

Melting point: melting at 145° C. (Köfler block)

¹H NMR spectrum at 300 MHz: 3.28 (s, 3H); 3.32 (partially masked m, 2H); 3.41 (m, 2H); 6.84 (broad t, J=5.5, Hz, 1H); 7.06 (dd, J=2.5 and 9.0 Hz, 1H); 7.42 (broad t, J=8.5 Hz, 2H); 7.58 (d, J=9.0 Hz, 1H); 7.80 (d, J=2.5 Hz, 1H); 7.92 (tt, J=6.0 and 8.5 Hz, 1H); 10.8 (broad m, 1H).

b) 1-(6-Hydroxy-1,3-benzothiazol-2-yl)-3-(2-methoxyethyl)urea 1-(6-Hydroxy-1,3-benzothiazol-2-yl)-3-(2-methoxyethyl)urea may be prepared as in Example 6b), but starting with 500 mg of methyl(6-hydroxy-1,3-benzothiazol-2-yl)carbamate and 1.68 g of 2-methoxyethylamine in 10 cm³ of 1-methylpyrrolidin-2-one. 300 mg of 1-(6-hydroxy-1,3-benzothiazol-2-yl)-3-(2-methoxyethyl)urea are thus obtained in the form of a grey powder, the characteristics of which are as follows:

Melting point: melting at 225° C. (Köfler block)

¹H NMR spectrum at 400 MHz: 3.28 (s, 3H); 3.32 (partially masked m, 2H); 3.41 (t, J=5.5 Hz, 2H); 6.79 (dd, J=2.5 and 8.5 Hz, 1H); 6.81 (partially masked broad t, J=5.5 Hz, 1H); 7.18 (d, J=2.5 Hz, 1H); 7.40 (d, J=8.5 Hz, 1H); 9.35 (broad s, 1H); 10.4 (broad s, 1H).

Example 9

2-{[(2-Morpholin-4-ylethyl)carbamoyl]amino}-1H-benzimidazol-5-yl 2,6-difluorobenzenesulfonate 2-{[(2-Morpholin-4-ylethyl)carbamoyl]amino}-1H-benzimidazol-5-yl 2,6-difluorobenzenesulfonate may be prepared in the following manner:

To a solution of 250 mg of 1-(5-hydroxy-1H-benzimidazol-2-yl)-3-(2-morpholin-4-ylethyl)urea in 16.4 cm³ of aqueous 0.1N sodium hydroxide solution are added 191 mg of 2,6-difluorobenzenesulfonyl chloride. The solution is stirred for 24 hours at a temperature in the region of 20° C. After addition of 40 mg of 2,6-difluorobenzenesulfonyl chloride, the mixture is stirred for 5 hours at a temperature in the region of 20° C. The reaction medium is placed in an ice bath and the precipitate is then filtered off by suction, washed with three times 5 cm³ of ice-cold water and dried under reduced pressure over phosphorus pentoxide. After flash chromatography on a column of silica [eluent: dichloromethane/methanol (93/7 by volume)], 167 mg of 2-{[(2-morpholin-4-ylethyl)carbamoyl]amino}-1H-benzimidazol-5-yl 2,6-difluorobenzenesulfonate are obtained in the form of a pale yellow powder, the characteristics of which are as follows:

Melting point: melting at 190-192° C. (Köfler block)

¹H NMR spectrum at 400 MHz: 2.41 (m, 6H); 3.28 (partially masked m, 2H); 3.59 (m, 4H); 6.75 (dd, J=2.0 and 8.5 Hz, 1H); from 6.98 to 7.35 (broad m, 3H); 7.41 (t, J=9.0 Hz, 2H); 7.90 (m, 1H); 10.05 (broad m, 1H); 11.75 (broad m, 1H)

Mass spectrum: MS (CI): m/z 482: [MH]⁺

Example 10

2-{[(2-Morpholin-4-yl ethyl)carbamoyl]amino}-1H-benzimidazol-5-yl 2-(trifluoromethyl)benzenesulfonate 2-{[(2-Morpholin-4-ylethyl)carbamoyl]amino}-1H-benzimidazol-5-yl 2-(trifluoromethyl)benzenesulfonate may be prepared as in Example 9, but starting with 250 mg of 1-(5-hydroxy-1H-benzimidazol-2-yl)-3-(2-morpholin-4-ylethyl)urea in 13.5 cm³ of aqueous 0.1N sodium hydroxide solution and 335 mg of 2-trifluoromethyl-benzenesulfonyl chloride. After stirring for 5 days at a temperature in the region of 20° C., the reaction medium is evaporated to dryness under reduced pressure (2 kPa). After flash chromatography on silica [eluent: dichloromethane/methanol (90/10 by volume)], the product obtained is solidified in 5 cm³ of diisopropyl ether and then filtered off, washed with three times 3 cm³ of diisopropyl ether and dried under reduced pressure over phosphorus pentoxide. 128 mg of 2-{[(2-morpholin-4-ylethyl)carbamoyl]amino}-1H-benzimidazol-5-yl 2-(trifluoromethyl)benzenesulfonate are obtained in the form of a cream-coloured powder, the characteristics of which are as follows:

Melting point: melting at 140-145° C. (Köfler block)

¹H NMR spectrum at 400 MHz: from 2.36 to 2.45 (m, 6H); 3.28 (partially masked m, 2H); 3.58 (m, 4H); 6.65 (dd, J=2.5 and 9.0 Hz, 1H); 6.98 (broad m, 1H); 7.27 (broad m, 2H); 7.86 (t, J=7.5 Hz, 1H); from 7.97 to 8.04 (m, 2H); 8.18 (d, J=2.5 Hz, 1H); 10.05 (broad m, 1H); 11.7 (broad m, 1H)

Mass spectrum: MS (ES⁺): m/z=514 [MH⁺]

Example 11

2-{[(2-Morpholin-4-ylethyl)carbamoyl]amino}-1H-benzimidazol-5-yl 2-chloro-6-methylbenzenesulfonate 2-{[(2-Morpholin-4-ylethyl)carbamoyl]amino}-1H-benzimidazol-5-yl 2-chloro-6-methylbenzenesulfonate may be prepared as in Example 9, but starting with 200 mg of 1-(5-hydroxy-1H-benzimidazol-2-yl)-3-(2-morpholin-4-ylethyl)urea in 13 cm³ of aqueous 0.1N sodium hydroxide solution and 162 mg of 2-chloro-6-methyl-benzenesulfonyl chloride. After stirring for 3 days at a temperature in the region of 20° C., the reaction medium is immersed in an ice bath and the precipitate is filtered off by suction, washed with four times 5 cm³ of water and dried under reduced pressure over phosphorus pentoxide. After flash chromatography on a column of silica [eluent: dichloromethane/methanol (95/5 by volume)], the product obtained is solidified in 5 cm³ of diisopropyl ether and then filtered off by suction, washed with three times 2 cm³ of diisopropyl ether and dried under reduced pressure over phosphorus pentoxide. 63 mg of 2-{[(2-morpholin-4-ylethyl)carbamoyl]amino}-1H-benzimidazol-5-yl 2-chloro-6-methylbenzenesulfonate are obtained in the form of a cream-coloured powder, the characteristics of which are as follows:

Melting point: melting at 168° C. (Köfler block)

$^1$H NMR spectrum at 300 MHz: 2.40 (m, 6H); 2.42 (s, 3H); 3.28 (partially masked m, 2H); 3.59 (m, 4H); 6.71 (dd, J=2.5 and 8.5 Hz, 1H); 7.04 (broad m, 1H); 7.27 (d, J=8.5 Hz, 1H); 7.31 (broad m, 1H); 7.39 (broad d, J=7.5 Hz, 1H); 7.60 (t, J=7.5 Hz, 1H); 7.65 (dd, J=2.0 and 7.5 Hz, 1H); 10.0 (broad m, 1H); 11.7 (broad m, 1H)

Mass spectrum: MS (ES$^+$): m/z=494 [MH$^+$]

Example 12

2-[(Cyclopropylcarbamoyl)amino]-1H-benzimidazol-5-yl 2,6-dichlorobenzenesulfonate a) 2-[(Cyclopropylcarbamoyl)amino]-1H-benzimidazol-5-yl 2,6-dichlorobenzenesulfonate may be prepared in the following manner:

To a suspension of 300 mg of 1-cyclopropyl-3-(5-hydroxy-1H-benzimidazol-2-yl)urea in 100 cm³ of acetone are added 186 mg of triethylamine and 349 mg of 2,6-dichlorobenzenesulfonyl chloride. After stirring overnight at a temperature in the region of 20° C., 90 mg of 2,6-dichlorobenzenesulfonyl chloride are added and the mixture is stirred for a further 24 hours. The reaction medium is evaporated to dryness under reduced pressure (2 kPa). The residue is taken up in 50 cm³ of water and then extracted with three times 40 cm³ of ethyl acetate. The combined organic phases are dried over magnesium sulfate, filtered and evaporated to dryness under reduced pressure (0.5 kPa). After flash chromatography on a column of silica [eluent: dichloromethane/methanol (96.5/3.5 by volume)], the product obtained is solidified in 10 cm³ of diethyl ether and then filtered off, washed with three times 5 cm³ of diethyl ether and dried under reduced pressure over phosphorus pentoxide. 130 mg of 2-[(cyclopropylcarbamoyl)amino]-1H-benzimidazol-5-yl 2,6-dichlorobenzenesulfonate are obtained in the form of a cream-coloured powder, the characteristics of which are as follows:

Melting point: melting at 160-165° C. (Köfler block)

$^1$H NMR spectrum at 400 MHz: 0.47 (m, 2H); 0.68 (m, 2H); 2.62 (m, 1H); 6.75 (dd, J=2.5 and 8.5 Hz, 1H); 7.09 (broad m, 1H); 7.24 (broad m, 1H); 7.30 (broad d, J=8.5 Hz, 1H); from 7.68 to 7.79 (m, 3H); 9.82 (broad m, 1H); 11.75 (broad m, 1H)

Mass spectrum: MS (ES$^+$): m/z=441 [MH$^+$]

b) 1-Cyclopropyl-3-(5-hydroxy-1H-benzimidazol-2-yl)urea may be prepared in the following manner:

3 g of methyl(5-hydroxy-1H-benzimidazol-2-yl)carbamate are placed in 15 cm³ of 1-methyl-2-pyrrolidinone and 4.19 g of cyclopropylamine in a 20 cm³ microwave reactor. After the reaction has been hermetically closed, it is placed in the microwave cavity at 130° C. for 25 minutes. The reaction medium is evaporated to dryness under reduced pressure (0.2 to 0.4 kPa) with a bath temperature of 85° C. The residue is taken up in 100 cm³ of water, solidified, filtered off by suction and washed with three times 80 cm³ of water. The cake is taken up in 30 cm³ of a dichloromethane/methanol mixture (90/10 by volume) and the insoluble material is filtered off. This operation is repeated ten times. The filtrates are evaporated to dryness under reduced pressure (2 kPa) at a bath temperature of 50° C. After flash chromatography on a column of silica [eluent: dichloromethane/methanol (90/10 by volume)], 300 mg of 1-cyclopropyl-3-(5-hydroxy-1H-benzimidazol-2-yl)urea are obtained in the form of cream-coloured crystals, the characteristics of which are as follows:

Melting point: melting at 320° C.

$^1$H NMR spectrum at 300 MHz: 0.47 (m, 2H); 0.67 (m, 2H); 2.62 (m, 1H); 6.48 (dd, J=2.5 and 8.5 Hz, 1H); 6.74 (broad m, 1H); 7.10 (d, J=8.5 Hz, 1H); 7.51 (broad m, 1H); 8.78 (broad m, 1H); 9.57 (very broad m, 1H); 12.65 (very broad m, 1H)

Mass spectrum: MS (ES$^+$): m/z=233 [MH$^+$]

c) Methyl(5-hydroxy-1H-benzimidazol-2-yl)carbamate was prepared as described in U.S. Pat. No. 6,900,235.

Example 13

2-({[2-(1-Benzylpiperidin-4-yl)ethyl]carbamoyl}amino)-1H-benzimidazol-5-yl 2,6-dichlorobenzenesulfonate a) 2-({[2-(1-Benzylpiperidin-4-yl)ethyl]carbamoyl}amino)-1H-benzimidazol-5-yl 2,6-dichlorobenzenesulfonate may be prepared in the following manner: 300 mg of 2-[(methoxycarbonyl)amino]-1H-benzimidazol-5-yl 2,6-dichlorobenzenesulfonate are placed in 5 cm³ of 1-methyl-2-pyrrolidinone and 787 mg of 2-(1-benzylpiperidin-4-yl)ethanamine in a microwave reactor. After the reactor has been hermetically closed, it is placed in the microwave cavity at 120° C. for 20 minutes. The reaction medium is evaporated to dryness under reduced pressure (0.2 kPa) with a bath temperature of 85° C. The residue is taken up in 50 cm³ of water and then extracted with three times 40 cm³ of ethyl acetate. The combined organic phases are dried over magnesium sulfate, filtered and evaporated under reduced pressure (2 kPa). After flash chromatography on a column of silica [eluent: dichloromethane/methanol (95/5 by volume)], the product obtained is solidified in 5 cm³ of diisopropyl ether, filtered off, washed with twice 2 cm³ of diisopropyl ether and dried under reduced pressure over phosphorus pentoxide. 193 mg of 2-({[2-(1-benzylpiperidin-4-yl)ethyl]carbamoyl}amino)-1H-benzimidazol-5-yl 2,6-dichlorobenzenesulfonate are obtained in the form of a white powder, the characteristics of which are as follows:

Melting point: melting at 130° C. (Köfler block)

$^1$H NMR spectrum at 400 MHz: 1.16 (m, 2H); 1.28 (m, 1H); 1.41 (m, 2H); 1.64 (m, 2H); 1.88 (m, 2H); 2.77 (m, 2H); 3.19 (q, J=7.0 Hz, 2H); 3.42 (s, 2H); 6.75 (dd, J=2.5 and 9.0 Hz, 1H); 7.08 (broad m, 2H); from 7.18 to 7.34 (m, 6H); from 7.68 to 7.77 (m, 3H); 9.90 (broad m, 1H); 11.7 (broad m, 1H)

Mass spectrum: MS (ES$^+$): m/z=602 [MH$^+$]

b) 2-[(Methoxycarbonyl)amino]-1H-benzimidazol-5-yl 2,6-dichlorobenzenesulfonate may be prepared in the following manner:

To a solution of 5.5 g of 3,4-diaminophenyl 2,6-dichlorobenzenesulfonate in a mixture of 153 cm³ of methanol and 991 mg of pure acetic acid are added 3.4 g of dimethyl[(Z)-(methylthio)methylylidene]biscarbamate. The mixture is refluxed for 4 hours. After cooling to a temperature in the region of 20° C., the precipitate is filtered off by suction, washed with three times 10 cm³ of methanol and dried under reduced pressure over potassium hydroxide. 5.8 g of 2-[(methoxycarbonyl)amino]-1H-benzimidazol-5-yl 2,6-dichlorobenzenesulfonate are obtained in the form of a white powder, the characteristics of which are as follows:

Melting point: melting at 261° C. (Köfler block)

Mass spectrum: MS (EI): m/z=415 [M+]

c) 3,4-Diaminophenyl 2,6-dichlorobenzenesulfonate may be prepared in the following manner:

To a solution of 2 g of 4-amino-3-nitrophenyl 2,6-dichlorobenzenesulfonate in 85 cm$^3$ of methanol and 33 cm$^3$ of pure acetic acid are added 2.25 g of iron powder. The reaction medium is refluxed for three hours. The insoluble material is filtered off and washed with three times 10 cm$^3$ of preheated methanol. The filtrate is evaporated to dryness under reduced pressure (2 kPa) at a bath temperature of 50° C. The residue is taken up in 50 cm$^3$ of water and then brought to pH 8-9 with sodium hydrogen carbonate and extracted with five times 80 cm$^3$ of dichloromethane. The combined organic phases are dried over magnesium sulfate, filtered and evaporated to dryness under reduced pressure (2 kPa). After flash chromatography on a column of silica [eluent: dichloromethane/methanol (98/2 by volume)], 900 mg of 3,4-diaminophenyl 2,6-dichlorobenzenesulfonate are obtained in the form of orange crystals, the characteristics of which are as follows:

Melting point: melting at 100° C. (Köfler block)
Mass spectrum: MS (EI): m/z=332 [M+]

d) 4-Amino-3-nitrophenyl 2,6-dichlorobenzenesulfonate may be prepared in the following manner:

To a solution of 3.14 g of 4-amino-3-nitrophenol in 50 cm$^3$ of acetone are added 5 g of 2,6-dichlorobenzenesulfonyl chloride. The reaction medium is stirred for five minutes and then placed in a bath of ice-water so as not to exceed 30° C. during the addition of 2.9 cm$^3$ of triethylamine. The formation of a precipitate is observed, and the mixture is stirred for twenty-four hours at a temperature in the region of 20° C. 500 mg of 2,6-dichlorobenzenesulfonyl chloride are added and, after stirring for two hours, the insoluble material is filtered off, washed with three times 30 cm$^3$ of acetone and set aside*. The filtrate is evaporated to dryness under reduced pressure (2 kPa) and the residue is taken up in 1 L of dichloromethane and then washed with three times 40 cm$^3$ of water. The organic phase is dried over magnesium sulfate, filtered and evaporated to dryness under reduced pressure (2 kPa). 3.28 g of 4-amino-3-nitrophenyl 2,6-dichlorobenzenesulfonate are obtained in the form of orange crystals, the characteristics of which are as follows:

Melting point: melting at 180° C. (Köfler block)
Mass spectrum: MS: ES−: m/z=361 [MH−]

The insoluble material is taken up 50 cm$^3$ of water, filtered again, washed with three times 30 cm$^3$ of water, filtered off by suction and dried under reduced pressure over phosphorus pentoxide. 3.72 g of 4-amino-3-nitrophenyl 2,6-dichlorobenzenesulfonate are obtained in the form of a yellow powder, the characteristics of which are as follows:

Melting point: melting at 180° C. (Köfler block)
Mass spectrum: MS: ES−: m/z=361 [MH−]

Example 14

2-({[2-(4-Benzylpiperazin-1-yl)ethyl]carbamoyl}amino)-1H-benzimidazol-5-yl 2,6-dichlorobenzenesulfonate 2-({[2-(4-Benzylpiperazin-1-yl)ethyl]carbamoyl}amino)-1H-benzimidazol-5-yl 2,6-dichlorobenzenesulfonate may be prepared as in Example 13a, but starting with 300 mg of 2-[(methoxycarbonyl)amino]-1H-benzimidazol-5-yl 2,6-dichlorobenzenesulfonate in 4.5 cm$^3$ of 1-methyl-2-pyrrolidinone and 500 mg of 2-(4-benzylpiperazin-1-yl)ethanamine. After flash chromatography on a column of silica [eluent: dichloromethane/methanol (95/5 by volume)], the product obtained is recrystallized while hot from 15 cm$^3$ of acetonitrile and filtered off by suction at a temperature in the region of 20° C., washed with twice 2 cm$^3$ of acetonitrile and three times 4 cm$^3$ of diethyl ether and then dried under reduced pressure over phosphorus pentoxide. 241 mg of 2-({[2-(4-benzylpiperazin-1-yl)ethyl]carbamoyl}amino)-1H-benzimidazol-5-yl 2,6-dichlorobenzenesulfonate are obtained in the form of a powder with a violet tint, the characteristics of which are as follows:

Melting point: melting at 190° C.-192° C. (Köfler block)
$^1$H NMR spectrum at 400 MHz: from 2.34 to 2.47 (broad m, 10H); 3.26 (partially masked m, 2H); 3.47 (s, 2H); 6.74 (dd, J=2.5 and 8.5 Hz, 1H); 7.09 (broad m, 1H); from 7.20 to 7.35 (m, 7H); from 7.68 to 7.78 (m, 3H); 10.0 (very broad m, 1H); 11.75 (very broad m, 1H)
Mass spectrum MS (ES$^+$): m/z=937 [MH$^+$]

Example 15

2-{[(Pyridin-2-ylmethyl)carbamoyl]amino}-1H-benzimidazol-5-yl 2,6-dichlorobenzenesulfonate 2-{[(Pyridin-2-ylmethyl)carbamoyl]amino}-1H-benzimidazol-5-yl 2,6-dichlorobenzenesulfonate may be prepared as in Example 13a, but starting with 200 mg of 2-[(methoxycarbonyl)amino]-1H-benzimidazol-5-yl 2,6-dichlorobenzenesulfonate in 7 cm$^3$ of 1-methyl-2-pyrrolidinone and 260 mg of 1-pyridin-2-ylmethanamine for 25 minutes at 130° C. After flash chromatography on a column of silica [eluent: dichloromethane/methanol (95/5 by volume)], the solid obtained is solidified in 10 cm$^3$ of diisopropyl ether, filtered off by suction, washed with three times 5 cm$^3$ of diisopropyl ether and then dried under reduced pressure over phosphorus pentoxide. 160 mg of 2-{[(pyridin-2-ylmethyl)carbamoyl]amino}-1H-benzimidazol-5-yl 2,6-dichlorobenzenesulfonate are obtained in the form of a white powder, the characteristics of which are as follows:

Melting point: melting at 204° C. (Köfler block)
$^1$H NMR spectrum at 300 MHz: 4.49 (d, J=5.5 Hz, 2H); 6.73 (dd, J=2.5 and 8.5 Hz, 1H); 7.07 (broad s, 1H); from 7.24 to 7.31 (m, 2H); 7.37 (broad d, J=8.0 Hz, 1H); from 7.67 to 7.81 (m, 4H); 7.93 (broad m, 1H); 8.53 (broad d, J=5.5 Hz, 1H); 10.1 (broad m, 1H); 11.85 (broad m, 1H)
Mass spectrum MS (ES+): m/z=492 [MH+]

Example 16

2-{[(Pyridin-3-ylmethyl)carbamoyl]amino}-1H-benzimidazol-5-yl 2,6-dichlorobenzenesulfonate 2-{[(Pyridin-3-ylmethyl)carbamoyl]amino}-1H-benzimidazol-5-yl 2,6-dichlorobenzenesulfonate may be prepared as in Example 13a, but starting with 200 mg of 2-[(methoxycarbonyl)amino]-1H-benzimidazol-5-yl 2,6-dichlorobenzenesulfonate in 6 cm$^3$ of 1-methyl-2-pyrrolidinone and 260 mg of 1-pyridin-3-ylmethanamine for 25 minutes at 130° C. After flash chromatography on a column of silica [eluent: dichloromethane/methanol (90/10 by volume)], the solid obtained is solidified in 10 cm$^3$ of diisopropyl ether, filtered off by suction, washed with three times 5 cm$^3$ of diisopropyl ether and dried under reduced pressure over phosphorus pentoxide. 169 mg of 2-{[(pyridin-3-ylmethyl)carbamoyl]amino}-1H-benzimidazol-5-yl 2,6-dichlorobenzenesulfonate are obtained in the form of a white powder, the characteristics of which are as follows:

Melting point: melting at 210° C. (Köfler block)
$^1$H NMR spectrum at 400 MHz: 4.41 (d, J=6.0 Hz, 2H); 6.75 (dd, J=2.5 and 8.5 Hz, 1H); 7.09 (broad s, 1H); 7.29 (d, J=8.5 Hz, 1H); 7.38 (dd, J=5.0 and 8.0 Hz, 1H); from 7.68 to 7.76 (m, 5H); 8.46 (dd, J=2.0 and 5.0 Hz, 1H); 8.55 (d, J=2.5 Hz, 1H); 10.15 (broad m, 1H); 11.7 (broad m, 1H)

Mass spectrum MS (ES+): m/z=492 [MH+]

Example 17

2-{[(Pyridin-4-ylmethyl)carbamoyl]amino}-1H-benzimidazol-5-yl 2,6-dichlorobenzenesulfonate 2-{[(Pyridin-4-ylmethyl)carbamoyl]amino}-1H-benzimidazol-5-yl 2,6-dichlorobenzenesulfonate may be prepared as in Example 13a, but starting with 200 mg of 2-[(methoxycarbonyl)amino]-1H-benzimidazol-5-yl 2,6-dichlorobenzenesulfonate in 7 cm³ of 1-methyl-2-pyrrolidinone and 260 mg of 1-pyridin-4-ylmethanamine for 25 minutes at 130° C. After flash chromatography on a column of silica [eluent: dichloromethane/methanol (95/5 by volume)], the solid obtained is solidified in 10 cm³ of diisopropyl ether, filtered off by suction, washed with three times 5 cm³ of diisopropyl ether and dried under reduced pressure over phosphorus pentoxide. 175 mg of 2-{[(pyridin-4-ylmethyl)carbamoyl]amino}-1H-benzimidazol-5-yl 2,6-dichlorobenzenesulfonate are obtained in the form of a white powder, the characteristics of which are as follows:

Melting point: melting at 165-170° C. (Köfler block)

¹H NMR spectrum at 400 MHz: 4.42 (d, J=6.0 Hz, 2H); 6.75 (dd, J=2.5 and 8.5 Hz, 1H); 7.08 (broad s, 1H); from 7.26 to 7.32 (m, 3H); from 7.66 to 7.78 (m, 3H); 7.85 (broad m, 1H); 8.50 (broad d, J=5.5 Hz, 2H); 10.35 (broad m, 1H); 11.7 (broad m, 1H)

Mass spectrum MS (ES+): m/z=492 [MH+]

Example 18

2-[(Benzylcarbamoyl)amino]-1H-benzimidazol-5-yl 2,6-dichlorobenzenesulfonate

2-[(Benzylcarbamoyl)amino]-1H-benzimidazol-5-yl 2,6-dichlorobenzenesulfonate may be prepared as in Example 13a, but starting with 200 mg of 2-[(methoxycarbonyl)amino]-1H-benzimidazol-5-yl 2,6-dichlorobenzenesulfonate in 10 cm³ of 1-methyl-2-pyrrolidinone and 0.114 cm³ of benzylamine, for 25 minutes at 130° C. 181 mg of 2-[(benzylcarbamoyl)amino]-1H-benzimidazol-5-yl 2,6-dichlorobenzenesulfonate are obtained in the form of a cream-coloured powder, the characteristics of which are as follows:

Melting point: melting at 195° C. (Köfler block)

¹H NMR spectrum at 400 MHz: 4.39 (d, J=6.0 Hz, 2H); 6.74 (dd, J=2.5 and 8.5 Hz, 1H); 7.09 (broad s, 1H); from 7.20 to 7.39 (m, 6H); from 7.60 to 7.80 (m, 4H); 10.1 (broad m, 1H); 11.8 (broad m, 1H)

Mass spectrum MS (ES+): m/z=491 [MH+]

Example 19

2-{[(2-Pyridin-3-ylethyl)carbamoyl]amino}-1H-benzimidazol-5-yl 2,6-dichlorobenzenesulfonate 2-{[(2-Pyridin-3-ylethyl)carbamoyl]amino}-1H-benzimidazol-5-yl 2,6-dichlorobenzenesulfonate may be prepared as in Example 13a, but starting with 200 mg of 2-[(methoxycarbonyl)amino]-1H-benzimidazol-5-yl 2,6-dichlorobenzenesulfonate in 6 cm³ of 1-methyl-2-pyrrolidinone and 147 mg of 2-pyridin-3-ylethanamine, for 25 minutes at 130° C. After flash chromatography on a column of silica [eluent: dichloromethane/methanol (95/5 by volume)], the solid obtained is solidified in 3 cm³ of acetonitrile, filtered off by suction, washed with twice 0.5 cm³ of acetonitrile and then with three times 5 cm³ of diisopropyl ether and evaporated to dryness under reduced pressure. 132 mg of 2-{[(2-pyridin-3-ylethyl)carbamoyl]amino}-1H-benzimidazol-5-yl 2,6-dichlorobenzenesulfonate are obtained in the form of a white powder, the characteristics of which are as follows:

Melting point: melting at 131° C. (Köfler block)

¹H NMR spectrum at 400 MHz: 2.82 (t, J=6.5 Hz, 2H); 3.44 (q, J=6.5 Hz, 2H); 6.74 (broad d, J=8.5 Hz, 1H); 7.07 (broad m, 1H); from 7.25 to 7.35 (m, 3H); from 7.64 to 7.78 (m, 4H); 8.43 (broad d, J=5.5 Hz, 1H); 8.47 (broad s, 1H); 9.97 (broad m, 1H); 11.8 (broad m, 1H)

Mass spectrum MS (ES+): m/z=506 [MH+]

Example 20

2-({[2-(4-Methylpiperazin-1-yl)ethyl]carbamoyl}amino)-1H-benzimidazol-5-yl 2,6-dichlorobenzenesulfonate 2-({[2-(4-Methylpiperazin-1-yl)ethyl]carbamoyl}amino)-1H-benzimidazol-5-yl 2,6-dichlorobenzenesulfonate may be prepared as in Example 13a, but starting with 200 mg of 2-[(methoxycarbonyl)amino]-1H-benzimidazol-5-yl 2,6-dichlorobenzenesulfonate in 6 cm³ of 1-methyl-2-pyrrolidinone and 172 mg of 2-(4-methylpiperazin-1-yl)ethanamine for 25 minutes at 130° C. After flash chromatography on a column of silica [eluent: dichloromethane/methanol (80/20 by volume)], the solid obtained is solidified in 10 cm³ of diisopropyl ether, filtered off by suction, washed with twice 3 cm³ of diisopropyl ether and evaporated to dryness under reduced pressure over phosphorus pentoxide. 196 mg of 2-({[2-(4-methylpiperazin-1-yl)ethyl]carbamoyl}amino)-1H-benzimidazol-5-yl 2,6-dichlorobenzenesulfonate are obtained in the form of a white powder, the characteristics of which are as follows:

Melting point: melting at 180° C. (Köfler block)

¹H NMR spectrum at 400 MHz: 2.16 (s, 3H); from 2.22 to 2.54 (partially masked m, 10H); 3.27 (partially masked m, 2H); 6.75 (dd, J=2.5 and 9.0 Hz, 1H); 7.08 (broad m, 1H); 7.28 (d, J=9.0 Hz, 1H); 7.34 (broad m, 1H); from 7.67 to 7.79 (m, 3H); 10.0 (broad m, 1H); 11.8 (broad m, 1H)

Mass spectrum MS (ES+): m/z=527 [MH+]

Example 21 a) 2-{[(2-piperazin-1-ylethyl)carbamoyl]amino}-1H-benzimidazol-5-yl 2,6-dichlorobenzenesulfonate a) 2-{[(2-piperazin-1-ylethyl)carbamoyl]amino}-1H-benzimidazol-5-yl 2,6-dichlorobenzenesulfonate may be prepared in the following manner:

To a solution of 340 mg of tert-butyl 4-(2-{[(5-{[(2,6-dichlorophenyl)sulfonyl]oxy}-1H-benzimidazol-2-yl)carbamoyl]amino}ethyl)-piperazine-1-carboxylate in 60 cm³ of dichloromethane are added 631 mg of trifluoroacetic acid. The mixture is stirred for 24 hours at a temperature in the region of 20° C., and 590 mg of trifluoroacetic acid are then added. The reaction medium is stirred for three days and then evaporated to dryness under reduced pressure (2 kPa). The residue is taken up in 25 cm³ of water, brought to pH 9 with potassium carbonate and then extracted with three times 50 cm³ of ethyl acetate. The combined organic phases are dried over magnesium sulfate, filtered and evaporated to dryness under reduced pressure (2 kPa). After flash chromatography on a column of silica [eluent: chloroform/methanol/28% aqueous ammonia (12/6/0.5 by volume)], the resin obtained is solidified in 25 cm³ of diisopropyl ether, filtered, washed with three times 2 cm³ of diisopropyl ether and then dried under reduced pressure over phosphorus pentoxide. 165 mg of 2-{[(2-piperazin-1-ylethyl)carbamoyl]amino}-1H-benzimidazol-5-yl 2,6-dichlorobenzenesulfonate are obtained in the form of a white powder, the characteristics of which are as follows:

Melting point: melting at 145° C.-150° C. (Köfler block)
¹H NMR spectrum at 300 MHz: 2.34 (m, 4H); 2.39 (t, J=6.5 Hz, 2H); 2.71 (m, 4H); 3.26 (partially masked m, 2H); 6.75 (dd, J=2.5 and 9.0 Hz, 1H); 7.09 (broad m, 1H); 7.21 (broad m, 1H); 7.29 (d, J=9.0 Hz, 1H); from 7.66 to 7.79 (m, 3H); 9.98 (very broad m, 1H)
Mass spectrum MS (ES+): m/z=513 [MH+]

b) tert-Butyl 4-(2-{[(5-{[(2,6-dichlorophenyl)sulfonyl]oxy}-1H-benzimidazol-2-yl)carbamoyl]amino}ethyl)piperazine-1-carboxylate may be prepared as in Example 13a, but starting with 300 mg of 2-[(methoxycarbonyl)amino]-1H-benzimidazol-5-yl 2,6-dichlorobenzenesulfonate in 8 cm³ of 1-methyl-2-pyrrolidinone and 827 mg of tert-butyl 4-(2-aminoethyl)piperazine-1-carboxylate. After flash chromatography on a column of silica [eluent: dichloromethane/methanol (92.5/7.5 by volume)], the orange-coloured resin obtained is solidified in 20 cm³ of diisopropyl ether and the solid is filtered off by suction, washed with three times 5 cm³ of diisopropyl ether and dried under reduced pressure over phosphorus pentoxide. 353 mg of tert-butyl 4-(2-{[(5-{[(2,6-dichlorophenyl)sulfonyl]oxy}-1H-benzimidazol-2-yl)carbamoyl]-amino}ethyl)piperazine-1-carboxylate are obtained in the form of a white powder, the characteristics of which are as follows:

Rf TLC silica=0.307 [eluent: dichloromethane/methanol (90/10 by volume)]
Mass spectrum MS (ES⁺): m/z=613 [MH⁺]

Example 22

2-{[(2-Piperidin-4-ylethyl)carbamoyl]amino}-1H-benzimidazol-5-yl 2,6-dichlorobenzenesulfonate a) 2-{[(2-Piperidin-4-ylethyl)carbamoyl]amino}-1H-benzimidazol-5-yl 2,6-dichlorobenzenesulfonate may be prepared as in Example 21a, but starting with 250 mg of tert-butyl 4-(2-{[(5-{[(2,6-dichlorophenyl)sulfonyl]oxy}-1H-benzimidazol-2-yl)carbamoyl]amino}ethyl)piperidine-1-carboxylate in 50 cm³ of dichloromethane and 835 mg of trifluoroacetic acid. After flash chromatography on a column of silica [eluent: chloroform/methanol/28% aqueous ammonia (12/3/0.5 by volume)], the resin obtained is solidified in 8 cm³ of dichloromethane and the solid is filtered off by suction, washed with twice 3 cm³ of dichloromethane and dried under reduced pressure over phosphorus pentoxide. 143 mg of 2-{[(2-piperidin-4-ylethyl)carbamoyl]amino}-1H-benzimidazol-5-yl 2,6-dichlorobenzenesulfonate are obtained in the form of a white powder, the characteristics of which are as follows:

Melting point: melting at 165° C. (Köfler block)
¹H NMR spectrum at 400 MHz: 1.02 (m, 2H); 1.38 (m, 3H); 1.61 (m, 2H); 2.43 (dt, J=2.5 and 12.0 Hz, 2H); 2.91 (m, 2H); 3.20 (q, J=6.5 Hz, 2H); 6.73 (dd, J=2.5 and 8.5 Hz, 1H); 7.07 (d, J=2.5 Hz, 1H); 7.27 (d, J=8.5 Hz, 1H); 7.30 (broad m, 1H); from 7.68 to 7.78 (m, 3H); 9.70 (very broad m, 1H)
Mass spectrum MS (ES⁺): m/z=512 [MH⁺]

b) tert-Butyl 4-(2-{[(5-{[(2,6-dichlorophenyl)sulfonyl]oxy}-1H-benzimidazol-2-yl)carbamoyl]amino}ethyl)piperidine-1-carboxylate may be prepared as in Example 13a, but starting with 300 mg of 2-[(methoxycarbonyl)amino]-1H-benzimidazol-5-yl 2,6-dichlorobenzenesulfonate in 8 cm³ of 1-methyl-2-pyrrolidinone and 823 mg of tert-butyl 4-(2-aminoethyl)piperidine-1-carboxylate. After flash chromatography on a column of silica [eluent: dichloromethane/methanol (95/5 by volume)], the product obtained is purified on a column of silica [eluent: dichloromethane/methanol gradient from 98/2 to 95/5 by volume]. 93 mg of tert-butyl 4-(2-{[(5-{[(2,6-dichlorophenyl)-sulfonyl]oxy}-1H-benzimidazol-2-yl)carbamoyl]amino}ethyl)piperidine-1-carboxylate are obtained in the form of a white solid, the characteristics of which are as follows:

Rf TLC silica=0.416 [eluent: dichloromethane/methanol (90/10 by volume)]
Mass spectrum MS (ES+): m/z=612 [MH+]

Example 23

2-[(tert-Butoxycarbonyl)amino]-1H-benzimidazol-5-yl 2,6-dichlorobenzenesulfonate 2-[(tert-Butoxycarbonyl)amino]-1H-benzimidazol-5-yl 2,6-dichlorobenzenesulfonate may be prepared as in Example 13b, but starting with 900 mg of 3,4-diaminophenyl 2,6-dichlorobenzenesulfonate in 25 cm³ of methanol, 162 mg of acetic acid and 784 mg of di-tert-butyl[(Z)-(methylthio)methylylidene]biscarbamate. After refluxing for three heures, the solution is cooled and evaporated to dryness under reduced pressure (2 kPa), and the residue is taken up in 60 cm³ of saturated aqueous sodium hydrogen carbonate solution and then extracted with three times 50 cm³ of dichloromethane. The combined organic phases are washed with three times 20 cm³ of water and then dried over magnesium sulfate, filtered and evaporated to dryness under reduced pressure. After flash chromatography on a column of silica [eluent: dichloromethane], the solid obtained is recrystallized from 5 cm³ of hot acetonitrile. The mixture is then placed in a water bath at a temperature in the region of 5° C., and the precipitate is then filtered off, washed with three times 2 cm³ of acetonitrile and dried under reduced pressure. 193 mg of 2-[(tert-butoxycarbonyl)amino]-1H-benzimidazol-5-yl are obtained in the form of a white powder, the characteristics of which are as follows:

Melting point: melting at 205° C. (Köfler block)
¹H NMR spectrum at 400 MHz: 1.51 (s, 9H); 6.79 (dd, J=2.0 and 8.5 Hz, 1H); 7.10 (broad m, 1H); 7.33 (d, J=8.5 Hz, 1H); from 7.68 to 7.78 (m, 3H); 11.05 (very broad m, 1H); 11.95 (very broad m, 1H)
Mass spectrum MS (ES⁺): m/z=458 [MH⁺]

Example 24

2-[(Cyclopropylcarbonyl)amino]-1H-benzimidazol-5-yl 2,6-dichlorobenzenesulfonate a) 2-[(Cyclopropylcarbonyl)amino]-1H-benzimidazol-5-yl 2,6-dichlorobenzenesulfonate may be prepared in the following manner:

To a solution of 468 mg of N-[(dimethylamino)(3H-[1,2,3]triazolo[4,5-b]pyridin-3-yloxy)methylene]-N-methylmethanaminium hexafluorophosphate in 5 cm³ of dimethylformamide are added 159 mg of diisopropylethylamine and 106 mg of cyclopropanecarboxylic acid. After stirring the reaction medium for one hour at a temperature in the region of 20° C., 220 mg of 2-amino-1H-benzimidazol-5-yl 2,6-dichlorobenzenesulfonate are obtained. The mixture is stirred overnight at a temperature in the region of 20° C. The reaction medium is diluted with 50 cm³ of water and the insoluble material is filtered off, washed with three times 5 cm³ of water, filtered off by suction and dried under a stream of air. The solid obtained is solidified in 10 cm³ of a mixture of diethyl ether and acetonitrile (7/3 by volume) and then filtered off by suction, washed with three times 2 cm³ of diethyl ether and dried under reduced pressure over phosphorus pentoxide. 98 mg of 2-[(cyclopropylcarbonyl)amino]-1H-benzimidazol-5-yl 2,6-dichlorobenzenesulfonate are obtained in the form of a white powder, the characteristics of which are as follows:

Melting point: melting at 242° C. (Köfler block)
¹H NMR spectrum at 400 MHz: from 0.86 to 0.96 (m, 4H); 1.96 (m, 1H); 6.80 (broad d, J=9.0 Hz, 1H); 7.17 (broad m, 1H); 7.37 (broad d, J=9.0 Hz, 1H); from 7.68 to 7.79 (m, 3H); 11.9 (broad m, 1H); 12.15 (broad m, 1H)
Mass spectrum MS (ES⁺): m/z=426 [MH⁺]

b) 2-amino-1H-benzimidazol-5-yl 2,6-dichlorobenzenesulfonate may be prepared in the following manner:

To a solution of 250 mg of 2-[(tert-butoxycarbonyl)amino]-1H-benzimidazol-5-yl 2,6-dichlorobenzenesulfonate in 20 cm³ of dichloromethane are added 746 mg of trifluoroacetic acid. After stirring overnight at a temperature in the region of 20° C., 746 mg of trifluoroacetic acid are added. After stirring for 24 hours, the reaction medium is concentrated to dryness under reduced pressure (2 kPa) and then taken up in 40 cm³ of saturated aqueous sodium hydrogen carbonate solution. The aqueous phase is extracted with five times 60 cm³ of dichloromethane and the combined organic phases are dried over magnesium sulfate, filtered and concentrated to dryness under reduced pressure (2 kPa). After flash chromatography on a column of silica [eluent: dichloromethane/methanol (90/10 by volume)], the resin obtained is solidified in 5 cm³ of pentane and the solid obtained is filtered off by suction and then washed with three times 2 cm³ of pentane and dried under reduced pressure over phosphorus pentoxide. 80 mg of 2-amino-1H-benzimidazol-5-yl 2,6-dichlorobenzenesulfonate are obtained in the form of a beige-coloured powder, the characteristics of which are as follows:

Melting point: melting at 235° C. (Köfler block)
¹H NMR spectrum at 400 MHz: 6.32 (s, 2H); 6.56 (dd, J=2.5 and 8.5 Hz, 1H); 6.79 (broad m, 1H); 7.00 (d, J=8.5 Hz, 1H); from 7.67 to 7.77 (m, 3H); 10.8 (broad m, 1H)
Mass spectrum MS (ES+): m/z=358 [MH+]

Example 25

2-[(3-Pyridin-3-ylpropanoyl)amino]-1H-benzimidazol-5-yl 2,6-dichlorobenzenesulfonate 2-[(3-Pyridin-3-ylpropanoyl)amino]-1H-benzimidazol-5-yl 2,6-dichlorobenzenesulfonate may be prepared as in Example 24, but starting with a solution of 468 mg of N-[(dimethylamino)(3H-[1,2,3]triazolo[4,5-b]pyridin-3-yloxy)methylene]-N-methylmethanaminium hexafluorophosphate in 5 cm³ of dimethylformamide, 159 mg of diisopropylethylamine, 186 mg of 3-pyridin-3-ylpropanoic acid and 220 mg of 2-amino-1H-benzimidazol-5-yl 2,6-dichlorobenzenesulfonate. After stirring overnight, the reaction medium is diluted in 150 cm³ of water and extracted with three times 30 cm³ of ethyl acetate. The organic phases are combined, dried over magnesium sulfate, filtered and evaporated to dryness under reduced pressure. The residue is recrystallized from 3 cm³ of refluxing acetonitrile, the medium is placed in a water bath at a temperature in the region of 5° C., and the precipitate is filtered off by suction and washed with twice 1 cm³ of acetonitrile and with three times 2 cm³ of diethyl ether. The solid is dried under reduced pressure over phosphorus pentoxide. 235 mg of 2-[(3-pyridin-3-ylpropanoyl)amino]-1H-benzimidazol-5-yl 2,6-dichlorobenzenesulfonate are obtained in the form of a white powder, the characteristics of which are as follows:

Melting point: melting at 188° C. (Köfler block)
¹H NMR spectrum at 400 MHz: we observe a 50%-50% resolution of tautomers with: 2.80 (t, J=7.0 Hz, 2H); 2.96 (t, J=7.0 Hz, 2H); 6.80 (broad d, J=9.0 Hz, 0.5H); 6.83 (broad d, J=9.0 Hz, 0.5H); 7.11 (broad s, 0.5H); 7.24 (broad s, 0.5H); 7.31 (dd, J=5.0 and 8.0 Hz, 1H); 7.36 (d, J=9.0 Hz, 0.5H); 7.40 (d, J=9.0 Hz, 0.5H); 7.67 (td, J=2.0 and 8.0 Hz, 1H); from 7.69 to 7.79 (m, 3H); 8.40 (dd, J=2.0 and 5.0 Hz, 1H); 8.49 (d, J=2.0 Hz, 1H); 11.6 (broad m, 1H); 12.15 (broad s, 0.5H); 12.25 (broad s, 0.5H)
Mass spectrum MS (ES⁺): m/z=491 [MH⁺]

Example 26

2-{[3-(1-Benzoylpiperidin-4-yl)propanoyl]amino}-1H-benzimidazol-5-yl 2,6-dichlorobenzenesulfonate 2-{[3-(1-Benzoylpiperidin-4-yl)propanoyl]amino}-1H-benzimidazol-5-yl 2,6-dichlorobenzenesulfonate may be prepared as in Example 24, but starting with a solution of 468 mg of N-[(dimethylamino)(3H-[1,2,3]triazolo[4,5-b]pyridin-3-yloxy)methylene]-N-methylmethanaminium hexafluorophosphate in 10 cm³ of dimethylformamide, 159 mg of diisopropylethylamine, 321 mg of 3-(1-benzoylpiperidin-4-yl)propanoic acid and 220 mg of 2-amino-1H-benzimidazol-5-yl 2,6-dichlorobenzenesulfonate. After flash chromatography on a column of silica [eluent: dichloromethane/methanol (95/5 by volume)], the resin is solidified in 5 cm³ of ice-cold acetonitrile, filtered off by suction, washed with three times 2 cm³ of acetonitrile and three times 5 cm³ of diisopropyl ether and then dried under reduced pressure over phosphorus pentoxide. 166 mg of 2-{[3-(1-benzoylpiperidin-4-yl)propanoyl]amino}-1H-benzimidazol-5-yl 2,6-dichlorobenzenesulfonate are obtained in the form of a white powder, the characteristics of which are as follows:

Melting point: melting at 135° C. (Köfler block)
¹H NMR spectrum at 400 MHz: 1.11 (broad m, 2H); from 1.47 to 1.84 (m, 5H); 2.47 (partially masked m, 2H); 2.73 (broad m, 1H); 2.97 (broad m, 1H); 3.54 (broad m, 1H); 4.45 (broad m, 1H); 6.81 (broad d, J=8.5 Hz, 1H); 7.17 (broad s, 1H); from 7.31 to 7.46 (m, 6H); from 7.68 to 7.79 (m, 3H); 11.6 (broad m, 1H); 12.2 (broad m, 1H)
Mass spectrum MS (ES+): m/z=601 [MH+]
3-(1-Benzoylpiperidin-4-yl)propanoic acid may be prepared as described in patent EP 0 602 242 A1.

Example 27

2-[(3-Piperidin-4-ylpropanoyl)amino]-1H-benzimidazol-5-yl 2,6-dichlorobenzenesulfonate a) 2-[(3-Piperidin-4-ylpropanoyl)amino]-1H-benzimidazol-5-yl 2,6-dichlorobenzenesulfonate may be prepared as in Example 21a, but starting with 330 mg of tert-butyl 4-{3-[(5-{[(2,6-dichlorophenyl)sulfonyl]oxy}-1H-benzimidazol-2-yl)amino]-3-oxopropyl}piperidine-1-carboxylate, 40 cm³ of dichloromethane and 755 mg of trifluoroacetic acid. After bringing the reaction medium to pH 8-9 with potassium carbonate, the precipitate is filtered off and then solidified in 5 cm³ of ethyl acetate, filtered off by suction and washed with three times 1 cm³ of ethyl acetate. 91 mg of 2-[(3-piperidin-4-ylpropanoyl)amino]-1H-benzimidazol-5-yl 2,6-dichlorobenzenesulfonate are obtained in the form of a cream-coloured powder, the characteristics of which are as follows:

Melting point: melting at 135° C. (Köfler block)

$^1$H NMR spectrum at 400 MHz: 1.02 (m, 2H); 1.33 (m, 1H); 1.53 (q, J=7.0 Hz, 2H); 1.61 (m, 2H); from 2.39 to 2.52 (partially masked m, 4H); 2.94 (m, 2H); 6.82 (dd, J=2.5 and 9.0 Hz, 1H); 7.17 (broad m, 1H); 7.39 (d, J=9.0 Hz, 1H); from 7.68 to 7.79 (m, 3H); 11.5 (very broad m, 2H)

Mass spectrum MS (ES$^+$): m/z=497 [MH$^+$]

b) tert-Butyl 4-{3-[(5-{[(2,6-dichlorophenyl)sulfonyl]oxy}-1H-benzimidazol-2-yl)amino]-3-oxopropyl}piperidine-1-carboxylate may be prepared as in Example 24, but starting with 468 mg of N-[(dimethylamino)(3H-[1,2,3]triazolo[4,5-b]pyridin-3-yloxy)methylene]-N-methylmethanaminium hexafluorophosphate in 5 cm$^3$ of dimethylformamide, 159 mg of diisopropylethylamine and 316 mg of 3-[1-(tert-butoxycarbonyl)piperidin-4-yl]propanoic acid and 220 mg of 2-amino-1H-benzimidazol-5-yl 2,6-dichlorobenzenesulfonate. After flash chromatography on a column of silica [eluent: dichloromethane/methanol (97/3 by volume)], 336 mg of tert-butyl 4-{3-[(5-{[(2,6-dichlorophenyl)sulfonyl]oxy}-1H-benzimidazol-2-yl)amino]-3-oxopropyl}piperidine-1-carboxylate are obtained in the form of a translucent foam, the characteristics of which are as follows:

Rf TLC silica=0.215 [eluent: dichloromethane/methanol (95/5 by volume)]

Mass spectrum MS (ES$^+$): m/z=597 [MH$^+$]

Example 28

2-[(4-Piperidin-4-ylbutanoyl)amino]-1H-benzimidazol-5-yl 2,6-dichlorobenzenesulfonate a) 2-[(4-Piperidin-4-ylbutanoyl)amino]-1H-benzimidazol-5-yl 2,6-dichlorobenzenesulfonate may be prepared as in Example 21a, but starting with 190 mg of tert-butyl 4-{4-[(5-{[(2,6-dichlorophenyl)sulfonyl]oxy}-1H-benzimidazol-2-yl)amino]-4-oxobutyl}piperidine-1-carboxylate, 50 cm$^3$ of dichloromethane and 532 mg of trifluoroacetic acid. After flash chromatography on a column of silica [eluent: chloroform/methanol/28% aqueous ammonia (12/3/0.5 by volume)], a solid is obtained, which is solidified in 5 cm$^3$ of diisopropyl ether, filtered off by suction, washed with three times 2 cm$^3$ of diisopropyl ether and dried under reduced pressure over phosphorus pentoxide. 67 mg of 2-[(4-piperidin-4-ylbutanoyl)amino]-1H-benzimidazol-5-yl 2,6-dichlorobenzenesulfonate are obtained in the form of a white powder, the characteristics of which are as follows:

$^1$H NMR spectrum at 400 MHz: 0.98 (m, 2H); from 1.14 to 1.35 (m, 3H); from 1.53 to 1.69 (m, 4H); from 2.36 to 2.54 (partially masked m, 4H); 2.91 (m, 2H); 6.82 (dd, J=2.5 and 8.5 Hz, 1H); 7.17 (broad s, 1H); 7.38 (d, J=8.5 Hz, 1H); from 7.68 to 7.79 (m, 3H); 11.2 (very broad m, 1H)

Mass spectrum MS (ES$^+$): m/z=511 [MH$^+$]

b) tert-Butyl 4-{4-[(5-{[(2,6-dichlorophenyl)sulfonyl]oxy}-1H-benzimidazol-2-yl)amino]-4-oxobutyl}piperidine-1-carboxylate may be prepared as in Example 24, but starting with 424 mg of N-[(dimethylamino)(3H-[1,2,3]triazolo[4,5-b]pyridin-3-yloxy)methylene]-N-methylmethanaminium hexafluorophosphate in 20 cm$^3$ of dimethylformamide, 144 mg of diisopropylethylamine, 303 mg of 4-[1-(tert-butoxycarbonyl)piperidin-4-yl]butanoic acid and 200 mg of 2-amino-1H-benzimidazol-5-yl 2,6-dichlorobenzenesulfonate. After flash chromatography on a column of silica [eluent: dichloromethane/methanol (98/2 by volume)], 196 mg of tert-butyl 4-{4-[(5-{[(2,6-dichlorophenyl)sulfonyl]oxy}-1H-benzimidazol-2-yl)amino]-4-oxobutyl}piperidine-1-carboxylate are obtained in the form of a resin with a yellow tint, the characteristics of which are as follows:

$^1$H NMR spectrum at 400 MHz: 0.92 (m, 2H); 1.22 (m, 2H); 1.38 (s, 9H); 1.39 (partially masked m, 1H); 1.63 (m, 4H); 2.41 (t, J=6.5 Hz, 2H); 2.65 (broad m, 2H); 3.90 (m, 2H); 6.80 (broad d, J=9.0 Hz, 1H); 7.15 (broad m, 1H); 7.37 (d, J=9.0 Hz, 1H); from 7.67 to 7.79 (m 3H); 11.5 (broad m, 1H); 12.2 (broad m, 1H)

Mass spectrum MS (ES$^+$): m/z=611 [MH$^+$]

Example 29

2-[(Cyclopropylcarbonyl)amino]-1H-benzimidazol-5-yl 2,6-difluorobenzenesulfonate a) 2-[(Cyclopropylcarbonyl)amino]-1H-benzimidazol-5-yl 2,6-difluorobenzenesulfonate may be prepared as in Example 24, but starting with 468 mg of N-[(dimethylamino)(3H-[1,2,3]triazolo[4,5-b]pyridin-3-yloxy)methylene]-N-methylmethanaminium hexafluorophosphate in 5 cm$^3$ of dimethylformamide, 159 mg of diisopropylethylamine, 106 mg of cyclopropanecarboxylic acid and 200 mg of 2-amino-1H-benzimidazol-5-yl 2,6-difluorobenzenesulfonate. After flash chromatography on a column of silica [eluent: dichloromethane/methanol (95/5 by volume)], the solid obtained is solidified in 5 cm$^3$ of diethyl ether and then filtered off by suction, washed with three times 2 cm$^3$ of diethyl ether and dried under reduced pressure over phosphorus pentoxide. 135 mg of 2-[(cyclopropylcarbonyl)amino]-1H-benzimidazol-5-yl 2,6-difluorobenzenesulfonate are obtained in the form of cream-coloured crystals, the characteristics of which are as follows:

Melting point: melting at 174° C. (Köfler block)

$^1$H NMR spectrum at 400 MHz: we observe a 50%-50% resolution of tautomers with: from 0.91 (m, 4H); 1.96 (m, 1H); 6.80 (broad m, 1H); 7.14 (broad m, 0.5H); 7.23 (broad m, 0.5H); from 7.35 to 7.44 (m, 3H); 7.91 (m, 1H); 11.9 (broad s, 1H); from 12.1 to 12.25 (broad m, 1H)

Mass spectrum MS (ES+): m/z=394 [MH+]

b) 2-Amino-1H-benzimidazol-5-yl 2,6-difluorobenzenesulfonate may be prepared as in Example 21a, but starting with 930 mg of 2-[(tertbutoxycarbonyl)amino]-1H-benzimidazol-5-yl 2,6-difluorobenzenesulfonate, 20 cm$^3$ of dichloromethane and 3 g of trifluoroacetic acid. After recrystallization from acetonitrile, 163 mg of 2-amino-1H-benzimidazol-5-yl 2,6-difluorobenzenesulfonate are obtained in the form of a cream-coloured powder, the characteristics of which are as follows:

Melting point: melting at 215° C. (Köfler block)

$^1$H NMR spectrum at 300 MHz: 6.35 (s, 2H); 6.54 (dd, J=2.5 and 8.5 Hz, 1H); 6.79 (broad m, 1H); 7.00 (d, J=8.5 Hz, 1H); 7.39 (t, J=9.0 Hz, 2H); 7.89 (m, 1H); 10.9 (broad m, 1H)

Mass spectrum MS (CI): m/z=326 [MH+]

c) 2-[(tert-Butoxycarbonyl)amino]-1H-benzimidazol-5-yl 2,6-difluorobenzenesulfonate may be prepared as in Example 13b, but starting with 900 mg of 3,4-diaminophenyl 2,6-difluorobenzenesulfonate, 14 cm$^3$ of methanol, 180 mg of acetic acid and 1.044 g of di-tert-butyl[(Z)-(methylthio)-methylylidene]biscarbamate. After refluxing for 4 hours, the mixture is concentrated to dryness under reduced pressure (2 kPa). After flash chromatography on a column of silica [eluent: dichloromethane/methanol (95/5 by volume)], 656 mg of 2-[(tert-butoxycarbonyl)amino]-1H-benzimidazol-5-yl 2,6-difluorobenzenesulfonate are obtained in the form of an orange-coloured resin, the characteristics of which are as follows:

¹H NMR spectrum at 300 MHz: 1.51 (s, 9H); 6.79 (dd, J=2.5 and 8.5 Hz, 1H); 7.11 (broad m, 1H); 7.35 (d, J=8.5 Hz, 1H); 7.40 (t, J=9.0 Hz, 2H); 7.90 (m, 1H); 11.05 (broad m, 1H); 12.0 (broad m, 1H)

Mass spectrum MS (ES+): m/z=461 [MH+]

d) 3,4-Diaminophenyl 2,6-difluorobenzenesulfonate may be prepared in the following manner:

To a solution of 2 g of 3,4-diaminophenol in 150 cm³ of acetone are added 2.264 cm³ of triethylamine and 3.425 g of 2,6-difluorobenzenesulfonyl chloride. The reaction medium is stirred at a temperature in the region of 20° C. overnight. The insoluble material is filtered off and rinsed with three times 50 cm³ of acetone, and the filtrate is evaporated to dryness under reduced pressure (3.5 kPa). The residue is taken up in 300 cm³ of dichloromethane, washed with three times 50 cm³ of water, dried over magnesium sulfate, filtered and evaporated to dryness under reduced pressure. After flash chromatography on a column of silica [eluent: dichloromethane/methanol (95/5 by volume)], 650 mg of 3,4-diaminophenyl 2,6-difluorobenzenesulfonate are obtained in the form of a black resin, the characteristics of which are as follows:

¹H NMR spectrum at 300 MHz: 4.57 (broad s, 2H); 4.77 (broad s, 2H); 6.02 (dd, J=3.0 and 8.5 Hz, 1H); 6.33 (d, J=3.0 Hz, 1H); 6.37 (d, J=8.5 Hz, 1H); 7.38 (t, J=9.0 Hz, 2H); 7.87 (m, 1H)

Mass spectrum MS (ES⁺): m/z=301 [MH⁺]

3,4-Diaminophenol may be prepared as described by A. Schmidt et al. in Organic and Biomolecular Chemistry, 2003, 1 (23), 4342.

Example 30

2-{[(Pyridin-2-ylmethyl)carbamoyl]amino}-1,3-benzothiazol-6-yl 2,6-dichlorobenzenesulfonate a) 2-{[(Pyridin-2-ylmethyl)carbamoyl]amino}-1,3-benzothiazol-6-yl 2,6-dichlorobenzenesulfonate may be prepared as in Example 9, but starting with 415 mg of 1-(6-hydroxy-1,3-benzothiazol-2-yl)-3-(pyridin-2-ylmethyl)urea in 34.5 cm³ of aqueous 0.1N sodium hydroxide solution and 678 mg of 2,6-dichlorobenzenesulfonyl chloride. After stirring overnight at a temperature in the region of 20° C., the precipitate is filtered off by suction, washed with twice 5 cm³ of water and dried under reduced pressure. 511 mg of 2-{[(pyridin-2-ylmethyl)carbamoyl]amino}-1,3-benzothiazol-6-yl 2,6-dichlorobenzene-sulfonate are obtained in the form of a sand-coloured solid, the characteristics of which are as follows:

Melting point: melting at 118° C. (Köfler block)

¹H NMR spectrum at 400 MHz: 4.51 (d, J=5.5 Hz, 2H); 7.05 (dd, J=2.5 and 9.0 Hz, 1H); from 7.18 to 7.44 (m, 3H); 7.60 (d, J=9.0 Hz, 1H); from 7.70 to 7.87 (m, 5H); 8.55 (broad d, J=5.5 Hz, 1H); 11.1 (broad m, 1H)

Mass spectrum: MS (ES+): m/z=509 [MH+]

b) 1-(6-Hydroxy-1,3-benzothiazol-2-yl)-3-(pyridin-2-ylmethyl)urea may be prepared as in Example 13a, but starting with 400 mg of methyl 6-hydroxy-2-imino-1,3-benzothiazole-3(2H)-carboxylate in 6 cm³ of 1-methyl-2-pyrrolidinone and 960 mg of 1-pyridin-2-ylmethanamine. After 25 minutes at a temperature of 150° C. in the microwave cavity, the mixture is evaporated to dryness under reduced pressure. After flash chromatography on a column of silica [eluent: dichloromethane/methanol (95/5 by volume)], 415 mg of 1-(6-hydroxy-1,3-benzothiazol-2-yl)-3-(pyridin-2-ylmethyl)urea are obtained in the form of a yellow solid, the characteristics of which are as follows:

Rf TLC silica=0.34 [eluent: dichloromethane/methanol (95/5 by volume)]

Mass spectrum: MS (EI): m/z=300 [M+°]

c) Methyl 6-hydroxy-2-imino-1,3-benzothiazole-3(2H)-carboxylate may be prepared in the following manner:

956 mg of methyl 2-imino-6-[(methoxycarbonyl)oxy]-1,3-benzothiazole-3(2H)-carboxylate are placed in 38 cm³ of aqueous 5N potassium hydroxide solution in a three-necked flask. The solution is stirred at a temperature in the region of 20° C. for 5 hours. The reaction medium is placed in a bath at 0° C., and acetic acid is then added dropwise to pH 5-6. The precipitate is filtered off by suction and then washed with twice 5 cm³ of water. The solid is taken up in 10 cm³ of water, stirred for two hours and then filtered off by suction, washed with twice 2 cm³ of water and dried under a stream of air. 270 mg of methyl 6-hydroxy-2-imino-1,3-benzothiazole-3(2H)-carboxylate are obtained in the form of a white powder, the characteristics of which are as follows:

Mass spectrum: MS (EI): m/z=224 [M+°]

d) Methyl 2-imino-6-[(methoxycarbonyl)oxy]-1,3-benzothiazole-3(2H)-carboxylate may be prepared in the following manner:

1 g of 2-amino-1,3-benzothiazol-6-ol is introduced into 15 cm³ of pyridine in a three-necked flask. 1.02 cm³ of methyl chloroformate are added dropwise, while taking care not to exceed a temperature of 25° C. After stirring for five hours, 0.5 cm³ of methyl chloroformate is added. The reaction medium is stirred at a temperature in the region of 20° C. overnight. 30 cm³ of water are added and the precipitate is then filtered off by suction, washed with three times 5 cm³ of water and then dried over phosphorus pentoxide. 956 mg of methyl 2-imino-6-[(methoxycarbonyl)oxy]-1,3-benzothiazole-3(2H)-carboxylate are obtained in the form of a white solid, the characteristics of which are as follows:

Rf TLC silica=0.53 [eluent: dichloromethane/methanol (90/10 by volume)]

Mass spectrum: MS (ES+): m/z=283 [MH+]

Example 31

2-[(Cyclopropylcarbamoyl)amino]-1,3-benzothiazol-6-yl 2,6-dichlorobenzenesulfonate a) 2-[(Cyclopropylcarbamoyl)amino]-1,3-benzothiazol-6-yl 2,6-dichlorobenzenesulfonate may be prepared as in Example 9, but starting with 144 mg of 1-cyclopropyl-3-(6-hydroxy-1,3-benzothiazol-2-yl)urea in 14.5 cm³ of aqueous 0.1N sodium hydroxide solution and 284 mg of 2,6-dichlorobenzenesulfonyl chloride. After filtering the reaction medium, the precipitate is washed with twice 5 cm³ of water and dried under reduced pressure. 229 mg of 2-[(cyclopropylcarbamoyl)amino]-1,3-benzothiazol-6-yl 2,6-dichlorobenzenesulfonate are obtained in the form of a white solid, the characteristics of which are as follows:

Melting point: melting at 128° C. (Köfler block)

¹H NMR spectrum at 400 MHz: 1.48 (m, 2H); 1.68 (m, 2H); 2.61 (m, 1H); 6.93 (broad s, 1H); 7.04 (dd, J=2.5 and 9.0 Hz, 1H); 7.58 (d, J=9.0 Hz, 1H); from 7.70 to 7.79 (m, 3H); 7.81 (d, J=2.5 Hz, 1H); 10.65 (broad m, 1H)

Mass spectrum: MS (ES+): m/z=458 [MH+]

b) 1-Cyclopropyl-3-(6-hydroxy-1,3-benzothiazol-2-yl)urea may be prepared as in Example 13a, but starting with 260 mg of methyl 6-hydroxy-2-imino-1,3-benzothiazole-3(2H)-carboxylate in 6 cm³ of 1-methyl-2-pyrrolidinone and 330 mg of cyclopropylamine, for 25 minutes at a temperature of 150° C. in the microwave cavity. After flash chromatography on a column of silica [eluent: dichlmoromethane/methanol (95/5 by volume)], 144 mg of 1-cyclopropyl-3-(6-hydroxy-1,3-benzothiazol-2-yl)urea are obtained in the form of a white solid, the characteristics of which are as follows:

Rf TLC silica=0.29 [eluent: dichloromethane/methanol (90/10 by volume)]

Mass spectrum: MS (ES+): m/z=250 [MH+]

Example 32

2-{[(2-Methoxyethyl)carbamoyl]amino}-1,3-benzothiazol-6-yl 2,6-dichlorobenzenesulfonate 2-{[(2-Methoxyethyl)carbamoyl]amino}-1,3-benzothiazol-6-yl 2,6-dichlorobenzenesulfonate may be prepared as in Example 9, but starting with 300 mg of 1-6-hydroxy-1,3-benzothiazol-2-yl-3-(2-methoxyethyl) in 22.4 cm$^3$ of aqueous 0.1N sodium hydroxide solution and 303 mg of 2,6-dichlorobenzenesulfonyl chloride. After flash chromatography on a column of silica [eluent: dichlmoromethane/methanol (95/5 by volume)], the product obtained is solidified in 10 cm$^3$ of diisopropyl ether, filtered off by suction and then washed with three times 3 cm$^3$ of diisopropyl ether and dried over phosphorus pentoxide. 315 mg of 2-{[(2-methoxyethyl)carbamoyl]amino}-1,3-benzothiazol-6-yl 2,6-dichlorobenzenesulfonate are obtained in the form of a cream-coloured powder, the characteristics of which are as follows:

Melting point: melting at 210° C. (Köfler block)

$^1$H NMR spectrum at 300 MHz: 3.28 (s, 3H); 3.32 (partially masked m, 2H); 3.40 (m, 2H); 6.83 (broad t, J=6.0 Hz, 1H); 7.04 (dd, J=2.5 and 9.0 Hz, 1H); 7.57 (d, J=9.0 Hz, 1H); from 7.69 to 7.78 (m, 3H); 7.80 (d, J=2.5 Hz, 1H); 10.75 (broad m, 1H)

Mass spectrum: MS (ES+): m/z=630 [MH+]

Example 33

2-({[2-(1-Benzylpiperidin-4-yl)ethyl]carbamoyl}amino)-1,3-benzothiazol-6-yl 2,6-dichlorobenzenesulfonate a) 2-({[2-(1-Benzylpiperidin-4-yl)ethyl]carbamoyl}amino)-1,3-benzothiazol-6-yl 2,6-dichlorobenzenesulfonate may be prepared as in Example 9, but starting with 410 mg of 1-[2-(1-benzylpiperidin-4-yl)ethyl]-3-(6-hydroxy-1,3-benzothiazol-2-yl)urea in 25 cm$^3$ of aqueous 0.1N sodium hydroxide solution and 490 mg of 2,6-dichloro-benzenesulfonyl chloride. The precipitate formed is filtered off by suction, washed with twice 5 cm$^3$ of water and dried under reduced pressure. After flash chromatography on a column of silica [eluent: dichloromethane/methanol (90/10 by volume)], the solid obtained is solidified in 10 cm$^3$ of diisopropyl ether, filtered off by suction washed with twice 2 cm$^3$ of diisopropyl ether and dried under reduced pressure. 338 mg of 2-({[2-(1-benzylpiperidin-4-yl)ethyl]carbamoyl}amino)-1,3-benzothiazol-6-yl 2,6-dichlorobenzenesulfonate are obtained in the form of a green solid, the characteristics of which are as follows:

Melting point: melting at 105° C. (Köfler block)

$^1$H NMR spectrum at 400 MHz: from 1.11 to 1.45 (broad m, 5H); 1.67 (m, 2H); 1.91 (broad m, 1H); 2.50 (masked m, 1H); 2.82 (broad m, 2H); 3.17 (q, J=6.5 Hz, 2H); from 3.23 to 3.64 (partially masked broad m, 2H); 6.70 (broad m, 1H); 7.03 (dd, J=2.5 and 9.0 Hz, 1H); from 7.22 to 7.37 (broad m, 5H); 7.57 (d, J=9.0 Hz, 1H); from 7.70 to 7.81 (m, 4H); 10.75 (broad m, 1H)

Mass spectrum: MS (ES+): m/z=619 [MH+]

b) 1-[2-(1-Benzylpiperidin-4-yl)ethyl]-3-(6-hydroxy-1,3-benzothiazol-2-yl)urea may be prepared as in Example 13a, but starting with 300 mg of methyl 6-hydroxy-2-imino-1,3-benzothiazole-3(2H)-carboxylate in 6 cm$^3$ of 1-methyl-2-pyrrolidinone and 1.46 g of 2-(1-benzylpiperidin-4-yl)ethanamine. After 25 minutes at a temperature of 150° C. in the microwave cavity, the reaction medium is concentrated to dryness under reduced pressure. After flash chromatography on a column of silica [eluent: dichloromethane/methanol (95/5 by volume)], 410 mg of 1-[2-(1-benzylpiperidin-4-yl)ethyl]-3-(6-hydroxy-1,3-benzothiazol-2-yl)urea are obtained in the form of a beige-coloured solid, the characteristics of which are as follows:

Rf TLC silica=0.14 [eluent: dichloromethane/methanol (90/10 by volume)]

Mass spectrum: MS (ES$^+$): m/z=411 [MH$^+$]

Example 34

2-({[2-(4-Benzylpiperazin-1-yl)ethyl]carbamoyl}amino)-1,3-benzothiazol-6-yl 2,6-dichlorobenzenesulfonate a) 2-({[2-(4-Benzylpiperazin-1-yl)ethyl]carbamoyl}amino)-1,3-benzothiazol-6-yl 2,6-dichlorobenzenesulfonate may be prepared as in Example 9, but starting with 421 mg of 1-[2-(4-benzylpiperazin-1-yl)ethyl]-3-(6-hydroxy-1,3-benzothiazol-2-yl)urea in 25.5 cm$^3$ of aqueous 0.1N sodium hydroxide solution and 502 mg of 2,6-dichlorobenzenesulfonyl chloride. The precipitate formed is filtered off by suction, washed with twice 5 cm$^3$ of water and dried under a stream of air. After flash chromatography on a column of silica [eluent: dichloromethane/methanol (90/10 by volume)], the solid obtained is solidified in 10 cm$^3$ of diisopropyl ether, filtered off by suction, washed with twice 5 cm$^3$ of diisopropyl ether and dried under reduced pressure. 311 mg of 2-({[2-(4-benzylpiperazin-1-yl)ethyl]carbamoyl}amino)-1,3-benzothiazol-6-yl 2,6-dichlorobenzenesulfonate are obtained in the form of a white solid, the characteristics of which are as follows:

Melting point: melting at 102° C. (Köfler block)

$^1$H NMR spectrum at 400 MHz: from 2.33 to 2.46 (m, 10H); 3.25 (q, J=6.5 Hz, 2H); 3.46 (s, 2H); 6.78 (broad m, 1H); 7.02 (dd, J=2.5 and 9.0 Hz, 1H); from 7.20 to 7.33 (m, 5H); 7.54 (d, J=9.0 Hz, 1H); from 7.70 to 7.80 (m, 4H); 11.05 (very broad m, 1H)

Mass spectrum: MS (ES+): m/z=620 [MH+]

b) 1-[2-(4-Benzylpiperazin-1-yl)ethyl]-3-(6-hydroxy-1,3-benzothiazol-2-yl)urea may be prepared as in Example 13a but starting with 300 mg of methyl 6-hydroxy-2-imino-1,3-benzothiazole-3(2H)-carboxylate in 6 cm$^3$ of 1-methyl-2-pyrrolidinone and 440 mg of 2-(4-benzylpiperazin-1-yl)ethanamine. After 25 minutes at a temperature of 150° C. in the microwave cavity, the reaction medium is concentrated to dryness under reduced pressure. After flash chromatography on a column of silica [eluent: dichloromethane/methanol (90/10 by volume)], 421 mg of 1-[2-(4-benzylpiperazin-1-yl)ethyl]-3-(6-hydroxy-1,3-benzothiazol-2-yl)urea are obtained in the form of a yellow lacquer, the characteristics of which are as follows:

Rf TLC silica=0.14 [eluent: dichloromethane/methanol (90/10 by volume)]

Mass spectrum: MS (ES+): m/z=412 [MH+]

Example 35

2-{[(2-Piperidin-4-ylethyl)carbamoyl]amino}-1,3-benzothiazol-6-yl 2,6-dichlorobenzenesulfonate in the form of the trifluoroacetic acid salt a) 2-{[(2-Piperidin-4-ylethyl)carbamoyl]amino}-1,3-benzothiazol-6-yl 2,6-dichlorobenzenesulfonate in the form of the trifluoroacetic acid salt may be prepared as in Example 21a, but starting with 120 mg of tert-butyl 4-(2-{[(6-{[(2,6-dichlorophenyl)sulfonyl]oxy}-1,3-benzothiazol-2-yl)carbamoyl]amino}-ethyl)piperidine-1-carboxylate in 5 cm$^3$ of dichloromethane and 0.174 cm$^3$ of trifluoroacetic acid. 25 mg of a trifluoroacetic acid salt of 2-{[(2-piperidin-4-ylethyl)carbamoyl]amino}-1,3-benzothiazol-6-yl 2,6-dichlorobenzenesulfonate are obtained in the form of a white solid, the characteristics of which are as follows:

Melting point: melting at 240° C. (Köfler block)

$^1$H NMR spectrum at 400 MHz: from 1.20 (m, 2H); 1.41 (m, 2H); 1.50 (m, 1H); 1.78 (m, 2H); 2.73 (m, 2H); 3.18 (m, 2H); 6.77 (broad t, J=5.5 Hz, 1H); 7.03 (dd, J=2.5 and 8.5 Hz, 1H); 7.57 (d, J=8.5 Hz, 1H); from 7.70 to 7.82 (m, 4H); 8.76 (broad m, 1H)

Mass spectrum: MS (ES+): m/z=529 [MH+]

b) tert-Butyl 4-(2-{[(6-{[(2,6-dichlorophenyl)sulfonyl]oxy}-1,3-benzothiazol-2-yl)carbamoyl]amino}ethyl)piperidine-1-carboxylate may be prepared as in Example 9, but starting with 230 mg of tert-butyl 4-(2-{[(6-hydroxy-1,3-benzothiazol-2-yl)carbamoyl]amino}ethyl)piperidine-1-carboxylate in 5.5 cm$^3$ of aqueous 0.1N sodium hydroxide solution and 149 mg of 2,6-dichlorobenzenesulfonyl chloride. After flash chromatography on a column of silica [eluent: dichloromethane/methanol (95/5 by volume)], 120 mg of tert-butyl 4-(2-{[(6-{[(2,6-dichlorophenyl)sulfonyl]oxy}-1,3-benzothiazol-2-yl)carbamoyl]-amino}ethyl)piperidine-1-carboxylate are obtained in the form of a colourless lacquer, the characteristics of which are as follows:

Rf TLC silica=0.44 [eluent: dichloromethane/methanol (90/10 by volume)]

Mass spectrum: MS (ES+): m/z=629 [MH+]

c) tert-Butyl 4-(2-{[(6-hydroxy-1,3-benzothiazol-2-yl)carbamoyl]amino}ethyl)-piperidine-1-carboxylate may be prepared as in Example 13a, but starting with 400 mg of methyl 6-hydroxy-2-imino-1,3-benzothiazole-3(2H)-carboxylate in 6 cm$^3$ of 1-methyl-2-pyrrolidinone and 1.6 g of tert-butyl 4-(2-aminoethyl)piperidine-1-carboxylate. After 25 minutes at a temperature of 150° C. in the microwave cavity, the mixture is evaporated to dryness under reduced pressure. After flash chromatography on a column of silica [eluent: dichloromethane/methanol (95/5 by volume)], 230 mg of tert-butyl 4-(2-{[(6-hydroxy-1,3-benzothiazol-2-yl)carbamoyl]amino}ethyl)piperidine-1-carboxylate are obtained in the form of a yellow lacquer, the characteristics of which are as follows:

Rf TLC silica=0.39 [eluent: dichloromethane/methanol (90/10 by volume)]

Mass spectrum: MS (ES+): m/z=421 [MH+]

Example 36

2-{[(2-piperazin-1-ylethyl)carbamoyl]amino}-1,3-benzothiazol-6-yl 2,6-dichlorobenzenesulfonate a) 2-{[(2-piperazin-1-ylethyl)carbamoyl]amino}-1,3-benzothiazol-6-yl 2,6-dichlorobenzenesulfonate may be prepared as Example 21a, but starting with 307 mg of tert-butyl 4-(2-{[(6-{[(2,6-dichlorophenyl)sulfonyl]oxy}-1,3-benzothiazol-2-yl)carbamoyl]amino}ethyl)piperazine-1-carboxylate in 5 cm$^3$ of dicholomethane and 0.443 cm$^3$ of trifluoroacetic acid. After work-up, the residue is solidified in 5 cm$^3$ of diisopropyl ether and then filtered off by suction, washed with twice 2 cm$^3$ of diisopropyl ether and dried under reduced pressure. 120 mg of 2-{[(2-piperazin-1-ylethyl)carbamoyl]amino}-1,3-benzothiazol-6-yl 2,6-dichlorobenzenesulfonate are obtained in the form of a white solid, the characteristics of which are as follows:

Melting point: melting at 158° C. (Köfler block)

$^1$H NMR spectrum at 300 MHz: 2.32 (m, 4H); 2.38 (t, J=6.5 Hz, 2H); 2.71 (m, 4H); 3.25 (partially masked m, 2H); 6.75 (broad m, 1H); 7.03 (dd, J=2.5 and 9.0 Hz, 1H); 7.56 (d, J=9.0 Hz, 1H); from 7.69 to 7.80 (m, 4H)

Mass spectrum: MS (ES+): m/z=530 [MH+]

b) tert-Butyl 4-(2-{[(6-{[(2,6-dichlorophenyl)sulfonyl]oxy}-1,3-benzothiazol-2-yl)carbamoyl]amino}ethyl)piperazine-1-carboxylate may be prepared as in Example 9, but starting with 589 mg of tert-butyl 4-(2-{[(6-hydroxy-1,3-benzothiazol-2-yl)carbamoyl]amino}ethyl)piperazine-1-carboxylate in 14 cm$^3$ of aqueous 0.1N sodium hydroxide solution and 377 mg of 2,6-dichlorobenzenesulfonyl chloride. The precipitate formed is filtered off by suction, washed with twice 5 cm$^3$ of water and dried under a stream of air. After flash chromatography on a column of silica [eluent: dichloromethane/methanol (95/5 by volume)], 229 mg of tert-butyl 4-(2-{[(6-{[(2,6-dichlorophenyl)-sulfonyl]oxy}-1,3-benzothiazol-2-yl)carbamoyl]amino}ethyl)piperazine-1-carboxylate are obtained in the form of a beige-coloured solid, the characteristics of which are as follows:

Rf TLC silica=0.45 [eluent: dichloromethane/methanol (90/10 by volume)]

Mass spectrum: MS (ES+): m/z=630 [MH+]

c) tert-Butyl 4-(2-{[(6-hydroxy-1,3-benzothiazol-2-yl)carbamoyl]amino}ethyl)-piperazine-1-carboxylate may be prepared as in Example 13a, but starting with 500 mg of methyl 6-hydroxy-2-imino-1,3-benzothiazole-3(2H)-carboxylate in 6 cm$^3$ of 1-methyl-2-pyrrolidinone and 2 g of tert-butyl 4-(2-aminoethyl)piperazine-1-carboxylate for 25 minutes at 150° C. in the microwave cavity. After flash chromatography [eluent: dichloromethane/methanol (95/5 by volume)], 589 mg of tert-butyl 4-(2-{[(6-hydroxy-1,3-benzothiazol-2-yl)carbamoyl]amino}ethyl)piperazine-1-carboxylate are obtained in the form of a pale yellow foam, the characteristics of which are as follows:

Rf TLC silica=0.166 [eluent: dichloromethane/methanol (90/10 by volume)]

Mass spectrum: MS (ES+): m/z=422 [MH+]

Example 37

2-{[(2-Methoxyethyl)carbamoyl]amino}-1,3-benzothiazol-6-yl 2-chloro-6-methylbenzenesulfonate 2-{[(2-Methoxyethyl)carbamoyl]amino}-1,3-benzothiazol-6-yl 2-chloro-6-methylbenzenesulfonate may be prepared as in Example 9, but starting with 300 mg of 1-6-hydroxy-1,3-benzothiazol-2-yl-3-(2-methoxyethyl), 22.44 cm$^3$ of aqueous 0.1N sodium hydroxide solution and 278 mg of 2-chloro-6-methylbenzenesulfonyl chloride. After flash chromatography [eluent: dichloromethane/methanol (95/5 by volume)], the solid obtained is solidified in 10 cm$^3$ of diisopropyl ether, filtered off by suction, washed with three times 3 cm$^3$ of diisopropyl ether and dried over phosphorus pentoxide. 235 mg of 2-{[(2-methoxyethyl)carbamoyl]

amino}-1,3-benzothiazol-6-yl 2-chloro-6-methylbenzenesulfonate are obtained in the form of a cream-coloured powder, the characteristics of which are as follows:

Melting point: melting at 187° C. and at more than 260° C. (Köfler block)

$^1$H NMR spectrum at 300 MHz: 2.46 (s, 3H); 3.28 (s, 3H); 3.33 (partially masked m, 2H); 3.40 (m, 2H); 6.84 (broad t, J=6.0 Hz, 1H); 6.98 (dd, J=2.5 and 9.0 Hz, 1H); 7.43 (dd, J=2.5 and 7.5 Hz, 1H); 7.55 (d, J=9.0 Hz, 1H); from 7.59 to 7.71 (m, 2H); 7.74 (d, J=2.5 Hz, 1H); 10.75 (broad m, 1H)

Mass spectrum: MS (ES+): m/z=240 [MH+]

Example 38

2-{[(2-Morpholin-4-ylethyl)carbamoyl]amino}-1,3-benzothiazol-6-yl 2-chloro-6-methylbenzenesulfonate 2-{[(2-Morpholin-4-ylethyl)carbamoyl]amino}-1,3-benzothiazol-6-yl 2-chloro-6-methylbenzenesulfonate may be prepared as in Example 9, but starting with 234 mg of 1-(6-hydroxy-1,3-benzothiazol-2-yl)-3-(2-morpholin-4-ylethyl)urea in 18.1 cm$^3$ of aqueous 0.1N sodium hydroxide solution and 329 mg of 2-chloro-6-methylbenzenesulfonyl chloride. After recrystallization from acetonitrile, 196 mg of 2-{[(2-morpholin-4-ylethyl)carbamoyl]amino}-1,3-benzothiazol-6-yl 2-chloro-6-methylbenzenesulfonate are obtained in the form of a beige-coloured solid, the characteristics of which are as follows:

Melting point: melting at 131° C. (Köfler block)

$^1$H NMR spectrum at 400 MHz: from 2.36 to 2.44 (broad m, 6H); 2.46 (s, 3H); 3.27 (partially masked m, 2H); 3.59 (m, 4H); 6.77 (broad m, 1H); 6.97 (dd, J=2.5 and 9.0 Hz, 1H); 7.43 (broad d, J=7.5 Hz, 1H); 7.54 (d, J=9.0 Hz, 1H); 7.63 (t, J=7.5 Hz, 1H); 7.67 (broad d, J=7.5 Hz, 1H); 7.74 (d, J=2.5 Hz, 1H); 10.95 (broad m, 1H)

Mass spectrum: MS (ES+): m/z=240 [MH+]

Example 39

2-{[(2-Morpholin-4-ylethyl)carbamoyl]amino}-1,3-benzothiazol-6-yl 2-amino-4,6-dichlorobenzenesulfonate 2-{[(2-Morpholin-4-yl ethyl)carbamoyl]amino}-1,3-benzothiazol-6-yl 2-amino-4,6-dichlorobenzenesulfonate may be prepared as in Example 9, but starting with 500 mg of 1-(6-hydroxy-1,3-benzothiazol-2-yl)-3-(2-morpholin-4-ylethyl)urea in 15.5 cm$^3$ of aqueous 0.1N sodium hydroxide solution and 445 mg of 2-amino-4,6-dichlorobenzenesulfonyl chloride. After flash chromatography on a column of silica [eluent: dichloromethane/methanol (95/5 by volume)], the solid obtained is solidified in 5 cm$^3$ of diisopropyl ether, filtered by suction, washed with twice 2 cm$^3$ of diisopropyl ether and then dried under reduced pressure at a temperature of 35° C. 110 mg of 2-{[(2-morpholin-4-ylethyl)carbamoyl]amino}-1,3-benzothiazol-6-yl 2-amino-4,6-dichlorobenzenesulfonate are obtained in the form of a beige-coloured solid, the characteristics of which are as follows:

Melting point: melting at 128° C. (Köfler block)

$^1$H NMR spectrum at 400 MHz: 2.40 (m, 6H); 3.27 (partially masked m, 2H); 3.59 (m, 4H); 6.75 (broad s, 2H); 6.82 (broad m, 1H); 6.87 (d, J=2.5 Hz, 1H); 6.92 (d, J=2.5 Hz, 1H); 7.04 (dd, J=2.5 and 8.5 Hz, 1H); 7.56 (d, J=8.5 Hz, 1H); 7.78 (broad s, 1H); 11.1 (broad m, 1H)

Mass spectrum: MS (ES+): m/z=546 [MH+]

Example 40

2-{[(2-Morpholin-4-ylethyl)carbamoyl]amino}-1,3-benzothiazol-6-yl 2-chlorobenzenesulfonate 2-{[(2-Morpholin-4-ylethyl)carbamoyl]amino}-1,3-benzothiazol-6-yl 2-chlorobenzenesulfonate may be prepared as in Example 9, but starting with 245 mg of 1-(6-hydroxy-1,3-benzothiazol-2-yl)-3-(2-morpholin-4-ylethyl)urea in 7.6 cm$^3$ of aqueous 0.1N sodium hydroxide solution and 0.114 cm$^3$ of 2-chlorobenzenesulfonyl chloride. 126 mg of 2-{[(2-morpholin-4-ylethyl)carbamoyl]amino}-1,3-benzothiazol-6-yl 2-chlorobenzenesulfonate are obtained in the form of a white solid, the characteristics of which are as follows:

Melting point: melting at 100° C. (Köfler block)

$^1$H NMR spectrum at 300 MHz: 2.40 (m, 6H); 3.27 (partially masked m, 2H); 3.59 (m, 4H); 6.77 (broad t, J=5.5 Hz, 1H); 6.98 (dd, J=2.5 and 8.5 Hz, 1H); from 7.48 to 7.58 (m, 2H); 7.74 (d, J=2.5 Hz, 1H); 7.81 (dt, J=1.5 and 7.5 Hz, 1H); from 7.86 to 7.93 (m, 2H); 11.0 (broad m, 1H)

Mass spectrum: MS (ES$^+$): m/z=497 [MH+]

Example 41

2-[(Cyclopropylcarbonyl)amino]-1,3-benzothiazol-6-yl 2,6-difluorobenzenesulfonate a) 2-[(Cyclopropylcarbonyl)amino]-1,3-benzothiazol-6-yl 2,6-difluorobenzenesulfonate may be prepared in the following manner:

217 mg of 1H-benzotriazol-1-ol, 308 mg of N-[3-(dimethylamino)propyl]-N'-ethylcarbodiimide hydrochloride and 151 mg of cyclopropanecarboxylic acid are introduced into 10 cm$^3$ of DMF in a three-necked flask. The solution is stirred for about 1 hour at a temperature in the region of 20° C. 500 mg of 2-amino-1,3-benzothiazol-6-yl 2,6-difluorobenzenesulfonate in 10 cm$^3$ of DMF are added to this solution. After stirring for about 20 hours at a temperature in the region of 20° C., 75 mg of cyclopropanecarboxylic acid are added and the mixture is stirred for a further 24 hours. After concentrating to dryness under reduced pressure, the residue is taken up in 50 cm$^3$ of water and extracted with three times 50 cm$^3$ of dichloromethane. The organic phases are combined, dried over magnesium sulfate, filtered and concentrated under reduced pressure (2 kPa) at a bath temperature of 50° C. After flash chromatography on a column of silica [eluent: dichloromethane/acetonitrile/methanol (95/4/1 by volume)], 213 mg of a solid are obtained, and are chromatographed on a column of silica [eluent: dichloromethane/acetonitrile (95/5 by volume)] to give 143 mg of 2-[(cyclopropylcarbonyl)amino]-1,3-benzothiazol-6-yl 2,6-difluorobenzenesulfonate in the form of a white powder, the characteristics of which are as follows:

Melting point: melting at 145° C. (Köfler block)

$^1$H NMR spectrum at 400 MHz: from 0.92 to 0.98 (m, 4H); 1.99 (m, 1H); 7.14 (dd, J=2.5 and 9.0 Hz, 1H); 7.42 (t, J=9.0 Hz, 2H); 7.72 (d, J=9.0 Hz, 1H); 7.89 (d, J=2.5 Hz, 1H); 7.93 (m, 1H); 12.7 (broad m, 1H)

Mass spectrum: CI: m/z 411: [M+H]$^+$ b) 2-Amino-1,3-benzothiazol-6-yl 2,6-difluorobenzenesulfonate may be prepared in the following manner:

To a solution of 1 g of 2-amino-1,3-benzothiazol-6-ol in 66 cm$^3$ of aqueous 0.1N sodium hydroxide solution are added 1.279 g of 2,6-difluorobenzenesulfonyl chloride. The solution is stirred for 5 days at a temperature in the region of 20°

C. After addition of 10 cm³ of water, the precipitate is filtered off by suction and then washed with twice 3 cm³ of ice-cold water and dried under reduced pressure over phosphorus pentoxide. 2.1 g of 2-amino-1,3-benzothiazol-6-yl 2,6-difluorobenzenesulfonate are obtained in the form of a pink powder, the characteristics of which are as follows:

Melting point: melting at 179° C. (Köfler block)
Mass spectrum: EI: m/z=342 [M⁺]

Example 42

2-[(Cyclopropylcarbonyl)amino]-1,3-benzothiazol-6-yl 2,6-dichlorobenzenesulfonate a) 2-[(Cyclopropylcarbonyl)amino]-1,3-benzothiazol-6-yl 2,6-dichlorobenzenesulfonate may be prepared as in Example 41a, but starting with 450 mg of 2-amino-1,3-benzothiazol-6-yl 2,6-dichlorobenzenesulfonate, 20 cm³ of DMF, 178 mg of 1H-benzotriazol-1-ol, 253 mg of N-[3-(dimethylamino)propyl]-N-ethylcarbodiimide hydrochloride and 207 mg of cyclopropanecarboxylic acid. After flash chromatography on a column of silica [eluent: dichloromethane], a white solid is obtained, which is taken up in 10 cm³ of diisopropyl ether and then filtered off by suction, washed with twice 2 cm³ of diisopropyl ether and dried under reduced pressure. 108 mg of 2-[(cyclopropylcarbonyl)amino]-1,3-benzothiazol-6-yl 2,6-dichlorobenzenesulfonate are obtained in the form of a white powder, the characteristics of which are as follows:

Melting point: melting at 245° C. (Köfler block)
$^1$H NMR spectrum at 300 MHz: from 0.92 to 0.99 (m, 4H); 1.99 (m, 1H); 7.12 (dd, J=2.5 and 9.0 Hz, 1H); 7.70 (d, J=9.0 Hz, 1H); from 7.73 to 7.81 (m, 3H); 7.88 (d, J=2.5 Hz, 1H); 10.75 (broad m, 1H)
Mass spectrum: CI: m/z=443 [MH+]

b) 2-Amino-1,3-benzothiazol-6-yl 2,6-dichlorobenzenesulfonate may be prepared as in Example 41b, but starting with 1 g of 2-amino-1,3-benzothiazol-6-ol, 66 cm³ of aqueous 0.1N sodium hydroxide solution and 1.48 g of 2,6-dichloro-benzenesulfonyl chloride. 2.06 g of 2-amino-1,3-benzothiazol-6-yl 2,6-dichlorobenzenesulfonate are obtained in the form of a brown solid, the characteristics of which are as follows:

Melting point: melting at 198° C. (Köfler block)
$^1$H NMR spectrum at 300 MHz: 6.87 (dd, J=2.5 and 9.0 Hz, 1H); 7.26 (d, J=9.0 Hz, 1H); 7.58 (d, J=2.5 Hz, 1H); 7.66 (broad s, 2H); from 7.68 to 7.79 (m, 3H)
Mass spectrum: EI: m/z=374 [M+]

Example 43

2-[(3-Pyridin-3-ylpropanoyl)amino]-1,3-benzothiazol-6-yl 2,6-dichlorobenzenesulfonate 2-[(3-Pyridin-3-ylpropanoyl)amino]-1,3-benzothiazol-6-yl 2,6-dichlorobenzenesulfonate may be prepared as in Example 41a, but starting with 375 mg of 2-amino-1,3-benzothiazol-6-yl 2,6-dichlorobenzenesulfonate, 20 cm³ of DMF, 148 mg of 1H-benzotriazol-1-ol, 211 mg of N-[3-(dimethylamino)propyl]-N-ethylcarbodiimide hydrochloride and 302 mg of 3-pyridin-3-ylpropanoic acid. After flash chromatography on a column of silica [eluent: dichloromethane/methanol (95/5 by volume)], a white solid is obtained, which is taken up in 10 cm³ of diethyl ether and then filtered off by suction, washed with twice 2 cm³ of diethyl ether and dried under reduced pressure. 60 mg of 2-[(3-pyridin-3-ylpropanoyl)amino]-1,3-benzothiazol-6-yl 2,6-dichlorobenzenesulfonate are obtained in the form of a white powder, the characteristics of which are as follows:

Melting point: melting at 240° C. (Köfler block)
$^1$H NMR spectrum at 400 MHz: 2.83 (t, J=7.5 Hz, 2H); 2.96 (t, J=7.5 Hz, 2H); 7.10 (dd, J=2.5 and 9.0 Hz, 1H); 7.31 (dd, J=5.5 and 8.5 Hz, 1H); from 7.64 to 7.80 (m, 5H); 7.89 (d, J=2.5 Hz, 1H); 8.39 (dd, J=2.0 and 5.0 Hz, 1H); 8.48 (d, J=2.0 Hz, 1H); 12.5 (broad m, 1H)
Mass spectrum: ES⁺: m/z=508 [MH⁺]

Example 44

2-[(3-Morpholin-4-ylpropanoyl)amino]-1,3-benzothiazol-6-yl 2,6-dichlorobenzenesulfonate 2-[(3-Morpholin-4-ylpropanoyl)amino]-1,3-benzothiazol-6-yl 2,6-dichlorobenzenesulfonate may be prepared as in Example 41a, but starting with 440 mg of 2-amino-1,3-benzothiazol-6-yl 2,6-dichlorobenzenesulfonate, 10 cm³ of DMF, 174 mg of 1H-benzotriazol-1-ol, 247 mg of N-[3-(dimethylamino)propyl]-N-ethylcarbodiimide hydrochloride and 562 mg of 3-morpholin-4-ylpropanoic acid. After flash chromatography on a column of silica [eluent: dichloromethane/methanol (95/5 by volume)], a white solid is obtained, which is taken up in 5 cm³ of diethyl ether and then filtered off by suction, washed with twice 2 cm³ of diethyl ether and dried under reduced pressure. 124 mg of 2-[(3-morpholin-4-ylpropanoyl)amino]-1,3-benzothiazol-6-yl 2,6-dichlorobenzenesulfonate are obtained in the form of a white powder, the characteristics of which are as follows:

Melting point: melting at 179° C. (Köfler block)
$^1$H NMR spectrum at 300 MHz: 2.39 (m, 4H); 2.65 (s, 4H); 3.55 (m, 4H); 7.11 (dd, J=2.5 and 9.0 Hz, 1H); 7.69 (d, J=9.0 Hz, 1H); from 7.70 to 7.80 (m, 3H); 7.87 (d, J=2.5 Hz, 1H); 12.3 (very broad m, 1H)
Mass spectrum: ES+: m/z=516 [MH+]

Example 45

2-[(Pyridin-3-ylacetyl)amino]-1,3-benzothiazol-6-yl 2,6-dichlorobenzenesulfonate 2-[(Pyridin-3-ylacetyl)amino]-1,3-benzothiazol-6-yl 2,6-dichlorobenzenesulfonate may be prepared as in Example 41a, but starting with 375 mg of 2-amino-1,3-benzothiazol-6-yl 2,6-dichlorobenzenesulfonate, 20 cm³ of DMF, 149 mg of 1H-benzotriazol-1-ol, 211 mg of N-[3-(dimethylamino)propyl]-N-ethylcarbodiimide hydrochloride and 274 mg of pyridine-3-acetic acid. After flash chromatography on a column of silica [eluent: dichloromethane/methanol (95/5 by volume)], a white solid is obtained, which is taken up in 10 cm³ of diisopropyl ether and then filtered off by suction and washed with twice 2 cm³ of diisopropyl ether. 330 mg of 2-[(pyridin-3-ylacetyl)amino]-1,3-benzothiazol-6-yl 2,6-dichlorobenzenesulfonate are obtained in the form of a beige-coloured powder, the characteristics of which are as follows:

Melting point: melting at 218° C. (Köfler block)
$^1$H NMR spectrum at 300 MHz: 3.90 (s, 2H); 7.13 (dd, J=2.5 and 9.0 Hz, 1H); 7.37 (dd, J=5.0 and 8.0 Hz, 1H); from 7.69 to 7.80 (m, 5H); 7.90 (d, J=2.5 Hz, 1H); 8.48 (dd, J=2.0 and 5.0 Hz, 1H); 8.53 (broad d, J=2.5 Hz, 1H); 12.75 (broad m, 1H)
Mass spectrum: ES+: m/z=494 [MH+]

Example 46

2-[(Methoxycarbonyl)amino]-1,3-benzothiazol-6-yl 2,6-dichlorobenzenesulfonate 2-[(Methoxycarbonyl)amino]-1,3-benzothiazol-6-yl 2,6-dichlorobenzenesulfonate may be prepared in the following manner:

To a solution of 1 g of 2-amino-1,3-benzothiazol-6-yl 2,6-dichlorobenzenesulfonate in 25 cm³ of pyridine is added 0.308 cm³ of methyl chloroformate. The solution is stirred at a temperature in the region of 20° C. overnight. After addition of 0.62 cm³ of methyl chloroformate, the mixture is stirred for 72 hours at a temperature in the region of 20° C. 50 cm³ of water are added, and the precipitate formed is filtered off by suction and then washed with three times 10 cm³ of water and dried under reduced pressure. 785 mg of 2-[(methoxycarbonyl)amino]-1,3-benzothiazol-6-yl 2,6-dichlorobenzenesulfonate are obtained in the form of a beige-coloured powder, the characteristics of which are as follows:

Melting point: greater than 260° C. (Köfler block)

NMR spectrum at 400 MHz: 3.78 (s, 3H); 7.09 (dd, J=2.5 and 9.0 Hz, 1H); 7.66 (d, J=9.0 Hz, 1H); from 7.71 to 7.80 (m, 3H); 7.89 (d, J=2.5 Hz, 1H); 12.2 (broad m, 1H)

Mass spectrum: ES+: m/z=433 [MH+]

Example 47

2-[(3-Piperidin-4-ylpropanoyl)amino]-1,3-benzothiazol-6-yl 2,6-dichlorobenzenesulfonate a) 2-[(3-Piperidin-4-ylpropanoyl)amino]-1,3-benzothiazol-6-yl 2,6-dichlorobenzenesulfonate may be prepared as in Example 21a, but starting with 324 mg of tert-butyl 4-{3-[(6-{[(2,6-dichlorophenyl)sulfonyl]oxy}-1,3-benzothiazol-2-yl)amino]-3-oxopropyl}piperidine-1-carboxylate in 10 cm³ of dichloromethane and 0.49 cm³ of trifluoroacetic acid. After flash chromatography on a column of silica [eluent: chloroform/methanol/28% aqueous ammonia (12/3/0.5 by volume)], the solid obtained is solidified in 5 cm³ of diethyl ether and then filtered off by suction, washed with twice 3 cm³ of diethyl ether and dried under reduced pressure. 87 mg of 2-[(3-piperidin-4-ylpropanoyl)amino]-1,3-benzothiazol-6-yl 2,6-dichlorobenzenesulfonate are obtained in the form of a white solid, the characteristics of which are as follows:

Melting point: melting at 134° C. (Köfler block)

NMR spectrum at 400 MHz: 1.03 (m, 2H); 1.33 (m, 1H); 1.54 (m, 2H); 1.61 (m, 2H); from 2.42 to 2.54 (partially masked m, 4H); 2.95 (m, 2H); 7.10 (dd, J=2.5 and 9.0 Hz, 1H); 7.67 (d, J=9.0 Hz, 1H); from 7.71 to 7.80 (m, 3H); 7.85 (d, J=2.5 Hz, 1H)

Mass spectrum: ES+: m/z=514 [MH+]

b) tert-Butyl 4-{3-[(6-{[(2,6-dichlorophenyl)sulfonyl]oxy}-1,3-benzothiazol-2-yl)amino]-3-oxopropyl}piperidine-1-carboxylate may be prepared as in Example 41a, but starting with 720 mg of 2-amino-1,3-benzothiazol-6-yl 2,6-dichlorobenzenesulfonate, 20 cm³ of DMF, 285 mg of 1H-benzotriazol-1-ol, 403 mg of N-[3-(dimethylamino)propyl]-N-ethylcarbodiimide hydrochloride and 1 g of 3-[1-(tert-butoxycarbonyl)piperidin-4-yl]propanoic acid. After flash chromatography on a column of silica [eluent: dichloromethane/methanol (98/2 by volume)], 324 mg of tert-butyl 4-{3-[(6-{[(2,6-dichlorophenyl)sulfonyl]oxy}-1,3-benzothiazol-2-yl)amino]-3-oxopropyl}piperidine-1-carboxylate are obtained in the form of a pink-beige powder, the characteristics of which are as follows:

Rf TLC silica=0.64 [eluent: dichloromethane/methanol (90/10 by volume)]

Mass spectrum: ES+: m/z=614 [MH+]; m/z=558 [MH+]-terbutyl (base peak)

Example 48

2-[(4-Piperidin-4-ylbutanoyl)amino]-1,3-benzothiazol-6-yl 2,6-dichlorobenzenesulfonate a) 2-[(4-Piperidin-4-ylbutanoyl)amino]-1,3-benzothiazol-6-yl 2,6-dichlorobenzenesulfonate may be prepared as in Example 21a, but starting with 837 mg of tert-butyl 4-{4-[(6-{[(2,6-dichlorophenyl)sulfonyl]oxy}-1,3-benzothiazol-2-yl)amino]-4-oxobutyl}piperidine-1-carboxylate in 10 cm³ of dichloromethane and 1.22 cm³ of trifluoroacetic acid. The beige-coloured solid obtained is solidified in 10 cm³ of diethyl ether, filtered off by suction, washed with three times 5 cm³ of diethyl ether and dried under reduced pressure. 157 mg of 2-[(4-piperidin-4-ylbutanoyl)amino]-1,3-benzothiazol-6-yl 2,6-dichlorobenzenesulfonate are obtained in the form of a beige-coloured solid, the characteristics of which are as follows:

Melting point: melting at 114° C. (Köfler block)

¹H NMR spectrum at 400 MHz: 1.10 (m, 2H); 1.22 (m, 2H); 1.40 (broad m, 1H); from 1.56 to 1.76 (m, 4H); 2.47 (partially masked m, 2H); 2.63 (m, 2H); 3.08 (m, 2H); 7.11 (dd, J=2.5 and 9.0 Hz, 1H); 7.70 (d, J=9.0 Hz, 1H); from 7.72 to 7.81 (m, 3H); 7.90 (d, J=2.5 Hz, 1H)

Mass spectrum: ES+: m/z=528 [MH+]

b) tert-Butyl 4-{4-[(6-{[(2,6-dichlorophenyl)sulfonyl]oxy}-1,3-benzothiazol-2-yl)amino]-4-oxobutyl}piperidine-1-carboxylate may be prepared as in Example 41a, but starting with 800 mg of 2-amino-1,3-benzothiazol-6-yl 2,6-dichlorobenzenesulfonate, 15 cm³ of DMF, 317 mg of 1H-benzotriazol-1-ol, 448 mg of N-[3-(dimethylamino)propyl]-N-ethylcarbodiimide hydrochloride and 1.15 g of 4-[1-(tert-butoxycarbonyl)piperidin-4-yl]butanoic acid. After flash chromatography on a column of silica [eluent: dichloromethane/methanol (98/2 by volume)], 837 mg of tert-butyl 4-{4-[(6-{[(2,6-dichlorophenyl)-sulfonyl]oxy}-1,3-benzothiazol-2-yl)amino]-4-oxobutyl}piperidine-1-carboxylate are obtained in the form of a beige-coloured foam, the characteristics of which are as follows Rf TLC silica=0.52 [eluent: dichloromethane/methanol (90/10 by volume)]

Mass spectrum: ES⁺: m/z=628 [MH+]

Example 49

2-[(Cyclopropylcarbonyl)amino]-1,3-benzothiazol-6-yl 2-chloro-6-methylbenzenesulfonate a) 2-[(Cyclopropylcarbonyl)amino]-1,3-benzothiazol-6-yl 2-chloro-6-methylbenzenesulfonate may be prepared as in Example 41a, but starting with 450 mg of 2-amino-1,3-benzothiazol-6-yl 2-chloro-6-methylbenzenesulfonate, 20 cm³ of DMF, 189 mg of 1H-benzotriazol-1-ol, 267 mg of N-[3-(dimethylamino)propyl]-N-ethylcarbodiimide hydrochloride and 219 mg of cyclopropanecarboxylic acid. After flash chromatography on a column of silica [eluent: dichloromethane/methanol (98/2 by volume)], a solid is obtained, which is taken up in 10 cm³ of diethyl ether and then filtered off by suction, washed with twice 2 cm³ of diethyl ether and dried under reduced pressure. 115 mg of 2-[(cyclopropylcarbonyl)amino]-1,3-benzothiazol-6-yl 2-chloro-6-methylbenzenesulfonate are obtained in the form of a beige-coloured solid, the characteristics of which are as follows:

Melting point: melting at 128° C. (Köfler block)

$^1$H NMR spectrum at 400 MHz: from 0.90 to 0.98 (m, 4H); 1.98 (m, 1H); 2.47 (s, 3H); 7.05 (dd, J=2.5 and 9.0 Hz, 1H); 7.43 (dd, J=2.0 and 7.5 Hz, 1H); 7.63 (t, J=7.5 Hz, 1H); 7.67 (dd, J=2.0 and 7.5 Hz, 1H); 7.68 (d, J=9.0 Hz, 1H); 7.82 (dd, J=2.5 Hz, 1H); 12.7 (broad m, 1H)

Mass spectrum: ES+: m/z=423 [MH+]

b) 2-amino-1,3-benzothiazol-6-yl 2-chloro-6-methylbenzenesulfonate may be prepared as in Example 41b, but starting with 800 mg of 2-aminobenzothiazol-6-ol, 53 cm$^3$ of aqueous 0.1N sodium hydroxide solution and 1.08 g of 2-chloro-6-methyl-benzenesulfonyl chloride. The precipitate obtained is filtered off and washed with three times 5 cm$^3$ of water and dried under a stream of air. 1.34 g of 2-amino-1,3-benzothiazol-6-yl 2-chloro-6-methylbenzenesulfonate are obtained in the form of a pale brown solid, the characteristics of which are as follows:

Melting point: melting at 200° C. (Köfler block)

$^1$H NMR spectrum at 400 MHz: 2.46 (s, 3H); 6.83 (dd, J=2.5 and 9.0 Hz, 1H); 7.24 (d, J=9.0 Hz, 1H); 7.42 (broad d, J=7.5 Hz, 1H); 7.54 (d, J=2.5 Hz, 1H); 7.62 (t, J=7.5 Hz, 1H); 7.65 (dd, J=1.5 and 7.5 Hz, 1H); 7.70 (broad s, 2H)

Mass spectrum: EI: m/z=354 [M+]

Example 50

2-[(Cyclopropylcarbonyl)amino]-1,3-benzothiazol-6-yl 2,4,6-trichlorobenzenesulfonate a) 2-[(Cyclopropylcarbonyl)amino]-1,3-benzothiazol-6-yl 2,4,6-trichlorobenzenesulfonate may be prepared as in Example 41a, but starting with 63 mg of 1H-benzotriazol-1-ol, 89.5 mg of N-[3-(dimethylamino)propyl]-N-ethylcarbodiimide hydrochloride, 0.067 cm$^3$ of cyclopropanecarboxylic acid and 174 mg of 2-amino-1,3-benzothiazol-6-yl 2,4,6-trichlorobenzenesulfonate dissolved in 15 cm$^3$ of DMF. After flash chromatography on a column of silica [eluent: dichloromethane/methanol (99/1 by volume)], 74 mg of 2-[(cyclopropylcarbonyl)amino]-1,3-benzothiazol-6-yl 2,4,6-trichlorobenzenesulfonate are obtained in the form of a beige-coloured foam, the characteristics of which are as follows:

Melting point: melting at 184° C. (Köfler block)

$^1$H NMR spectrum at 400 MHz: from 0.89 to 0.97 (broad m, 4H); 1.97 (m, 1H); 7.13 (dd, J=2.5 and 9.0 Hz, 1H); 7.69 (d, J=9.0 Hz, 1H); 7.86 (d, J=2.5 Hz, 1H); 8.03 (s, 2H); 12.65 (broad m, 1H)

Mass spectrum: ES+: m/z=628 [MH+]

b) 2-Amino-1,3-benzothiazol-6-yl 2,4,6-trichlorobenzenesulfonate may be prepared as in Example 41b, but starting with 400 mg of 2-amino-1,3-benzothiazol-6-ol, 26 cm$^3$ of aqueous 0.1N sodium hydroxide solution and 675 mg of 2,4,6-trichlorobenzenesulfonyl chloride. After flash chromatography [eluent dichloromethane/methanol (95/5 by volume)], 174 mg of 2-amino-1,3-benzothiazol-6-yl 2,4,6-trichlorobenzenesulfonate are obtained in the form of a colourless lacquer, the characteristics of which are as follows:

Rf TLC silica=0.36 [eluent: dichloromethane/methanol (90/10 by volume)]

Mass spectrum: EI: m/z=408 [M+]

Example 51

2-{[(2-Morpholin-4-ylethyl)carbamoyl]amino}-1,3-benzothiazol-6-yl 2,4-difluoro-6-bromobenzenesulfonate 2-{[(2-Morpholin-4-ylethyl)carbamoyl]amino}-1,3-benzothiazol-6-yl 2,4-difluoro-6-bromobenzenesulfonate may be prepared as in Example 6a, but starting with 375 mg of 1-(6-hydroxy-1,3-benzothiazol-2-yl)-3-(2-morpholin-4-ylethyl)urea in 11.6 cm$^3$ of aqueous 0.1N sodium hydroxide solution and 372 mg of 2,4-difluoro-6-bromobenzenesulfonyl chloride.

After flash chromatography on a column of silica [eluent: dichloromethane/methanol (95/15 by volume)], the solid obtained is solidified in 10 cm$^3$ of diisopropyl ether, filtered off by suction, washed with twice 5 cm$^3$ of diisopropyl ether and dried under reduced pressure. 348 mg of 2-{[(2-morpholin-4-ylethyl)carbamoyl]amino}-1,3-benzothiazol-6-yl 2,4-difluoro-6-bromobenzenesulfonate are obtained in the form of a white solid, the characteristics of which are as follows:

Melting point: melting at 103° C. (Köfler block)

400 MHz $^1$H NMR spectrum: 2.40 (m: 6H); from 3.20 to 3.35 (partially masked m: 2H); 3.59 (m: 4H); 6.76 (m: 1H); 7.05 (dd, J=3 and 9 Hz, 1H); 7.57 (d, J=9 Hz: 1H); 7.70 (m: 1H); 7.77 (d, J=3 Hz: 1H); 7.93 (broad d, J=9 Hz: 1H); from 10.50 to 10.70 (broad m: 1H).

Mass spectrum: MS: 577 [MH$^+$]

Examples 52 to 79 a) The derivatives of Examples 52 to 79 were prepared in parallel synthesis in the following manner:

A solution of 100 mg of 2-[(phenoxycarbonyl)amino]-1,3-benzothiazol-6-yl 2,6-dichlorobenzenesulfonate in 1 cm$^3$ of tetrahydrofuran is placed in each tube of a Stem, with stirring. To each tube is added 1 equivalent of amine and 0.279 cm$^3$ of triethylamine in cases 66 and 79; the mixture is then stirred for about 18 hours at a temperature in the region of 20° C.

| Amine No. | Name | Mass | Volume |
|---|---|---|---|
| G52 | 1-[4-(4-methylpiperazin-1-yl)phenyl]methanamine | 41.47 mg | |
| G53 | 3-morpholin-4-ylpropan-1-amine | 29.13 mg | |
| G54 | N-methyl-N-phenylpropane-1,3-diamine | 33.18 mg | |
| G55 | 2-(4-benzylpiperidin-1-yl)ethanamine | 44.1 mg | |
| G56 | 2-pyrrolidin-1-ylethanamine | 23.07 mg | |
| G57 | 1-[(2R)-pyrrolidin-2-ylmethyl]pyrrolidine | 31.16 mg | |
| G58 | 1-[(2S)-pyrrolidin-2-ylmethyl]pyrrolidine | 31.16 mg | |
| G59 | 3-pyrrolidin-1-ylpropan-1-amine | 25.9 mg | |
| G60 | 2-(4-methylpiperazin-1-yl)ethanamine | 28.93 mg | |
| G61 | 2-(1-methylpyrrolidin-2-yl)ethanamine | | 0.029 cm$^3$ |
| G62 | N,N-dimethylpropane-1,3-diamine | | 0.025 cm$^3$ |
| G63 | 2-(2,6-dimethylpiperidin-1-yl)ethanamine | 61.57 mg | |
| G64 | 2-piperidin-1-ylethanamine | | 0.028 cm$^3$ |

-continued

| Amine No. | Name | Mass | Volume |
|---|---|---|---|
| G65 | 1-(3-aminopropyl)pyrrolidin-2-one | 28.72 mg | |
| G66 | 4-(aminomethyl)-N,N-dimethylaniline dihydrochloride | 45.08 mg | |
| G67 | 3-[4-(2-chloro-6-fluorobenzyl)piperazin-1-yl]propan-1-amine | 57.73 mg | |
| G68 | 3-(4-benzylpiperazin-1-yl)propan-1-amine | 41.14 mg | |
| G69 | 3-(4-methylpiperazin-1-yl)propan-1-amine | 31.77 mg | |
| G70 | 1-(4-morpholin-4-ylphenyl)methanamine | 38.84 mg | |
| G71 | 2M methanamine in THF | | 0.101 cm$^3$ |
| G72 | cycloheptanamine | 22.87 mg | |
| G73 | cyclopentanamine | 17.2 mg | |
| G74 | propan-2-amine | 11.94 mg | |
| G75 | cyclobutanamine | 14.37 mg | |
| G76 | 2-azepan-1-ylethanamine | 28.73 mg | |
| G77 | 2M N-methylmethanamine in THF | | 0.101 cm$^3$ |
| G78 | 1-pyridin-3-ylmethanamine | | 0.020 cm$^3$ |
| G79 | 2-(4-benzylpiperazin-1-yl)-2-oxoethanamine dihydrochloride | 49.95 mg | |

5 cm$^3$ of dichloromethane and 3 cm$^3$ of aqueous 0.1N sodium hydroxide solution are added to each tube. After stirring for about 2 minutes, the aqueous phase is removed; 3 cm$^3$ of water are added and, after stirring for 2 minutes, the aqueous phase is removed and this operation is repeated. The organic phase is dried over magnesium sulfate, filtered and concentrated under reduced pressure. The residues are purified by flash chromatography on a column of silica and the following compounds are obtained:

| Example | Nomenclature | Amount | Melting point (Köfler) or Rf TLC |
|---|---|---|---|
| 52 | 2-({[4-(4-methylpiperazin-1-yl)benzyl]carbamoyl}amino)-1,3-benzothiazol-6-yl 2,6-dichlorobenzene-sulfonate | 60.8 mg | 88° C. |
| 53 | 2-{[(3-morpholin-4-ylpropyl)carbamoyl]-amino}-1,3-benzothiazol-6-yl 2,6-dichlorobenzenesulfonate | 50.8 mg | 94° C. |
| 54 | 2-[({3-[methyl(phenyl)amino]propyl}-carbamoyl)amino]-1,3-benzothiazol-6-yl 2,6-dichlorobenzenesulfonate | 49.5 mg | 68° C. |
| 55 | 2-({[2-(4-benzylpiperidin-1-yl)ethyl]-carbamoyl}amino)-1,3-benzothiazol-6-yl 2,6-dichlorobenzenesulfonate | 15.4 mg | 95° C. |
| 56 | 2-{[(2-pyrrolidin-1-ylethyl)carbamoyl]-amino}-1,3-benzothiazol-6-yl 2,6-dichlorobenzenesulfonate | 38.9 mg | 99° C. |
| 57 | 2-({[(2R)-2-(pyrrolidin-1-ylmethyl)-pyrrolidin-1-yl]carbonyl}amino)-1,3-benzothiazol-6-yl 2,6-dichlorobenzene-sulfonate | 27.5 mg | 204° C. |
| 58 | 2-({[(2S)-2-(pyrrolidin-1-ylmethyl)pyrrolidin-1-yl]carbonyl}amino)-1,3-benzothiazol-6-yl 2,6-dichlorobenzene-sulfonate | 60.1 mg | 210° C. |
| 59 | 2-{[(3-pyrrolidin-1-ylpropyl)carbamoyl]-amino}-1,3-benzothiazol-6-yl 2,6-dichlorobenzenesulfonate | 52.5 mg | 96° C. |
| 60 | 2-({[2-(4-methylpiperazin-1-yl)ethyl]-carbamoyl}amino)-1,3-benzothiazol-6-yl 2,6-dichlorobenzenesulfonate | 33.8 mg | 100° C. |
| 61 | 2-({[2-(1-methylpyrrolidin-2-yl)ethyl]-carbamoyl}amino)-1,3-benzothiazol-6-yl 2,6-dichlorobenzenesulfonate | 26.8 mg | 178° C. |
| 62 | 2-({[3-(dimethylamino)propyl]-carbamoyl}amino)-1,3-benzothiazol-6-yl 2,6-dichlorobenzenesulfonate | 45 mg | 100° C. |
| 63 | 2-({[2-(2,6-dimethylpiperidin-1-yl)ethyl]-carbamoyl}amino)-1,3-benzothiazol-6-yl 2,6-dichlorobenzenesulfonate | 48.1 mg | 122° C. |
| 64 | 2-{[(2-piperidin-1-ylethyl)carbamoyl]-amino}-1,3-benzothiazol-6-yl 2,6-dichlorobenzenesulfonate | 76.5 mg | 172° C. |

-continued

| Example | Nomenclature | Amount | Melting point (Köfler) or Rf TLC |
|---|---|---|---|
| 65 | 2-({[3-(2-oxopyrrolidin-1-yl)propyl]-carbamoyl}amino)-1,3-benzothiazol-6-yl 2,6-dichlorobenzenesulfonate | 45.2 mg | 195° C. |
| 66 | 2-({[4-(dimethylamino)benzyl]-carbamoyl}amino)-1,3-benzothiazol-6-yl 2,6-dichlorobenzenesulfonate | 51 mg | 154.5° C. |
| 67 | 2-[({3-[4-(2-chloro-6-fluorobenzyl)-piperazin-1-yl]propyl}carbamoyl)amino]-1,3-benzothiazol-6-yl 2,6-dichloro-benzenesulfonate | 57 mg | 93° C. |
| 68 | 2-({[3-(4-benzylpiperazin-1-yl)propyl]-carbamoyl}amino)-1,3-benzothiazol-6-yl 2,6-dichlorobenzenesulfonate | 67.6 mg | 218° C. |
| 69 | 2-({[3-(4-methylpiperazin-1-yl)propyl]-carbamoyl}amino)-1,3-benzothiazol-6-yl 2,6-dichlorobenzenesulfonate | 55 mg | 96.5° C. |
| 70 | 2-{[(4-morpholin-4-ylbenzyl)carbamoyl]-amino}-1,3-benzothiazol-6-yl 2,6-di-chlorobenzenesulfonate | 35 mg | 177° C. |
| 71 | 2-[(methylcarbamoyl)amino]-1,3-benzo-thiazol-6-yl 2,6-dichlorobenzene-sulfonate | 12 mg | Rf TLC silica = 0.38 [eluent: dichloro-methane/ methanol (90/10 by volume)] |
| 72 | 2-[(cycloheptylcarbamoyl)amino]-1,3-benzothiazol-6-yl 2,6-dichlorobenzene-sulfonate | 40 mg | 163° C. |
| 73 | 2-[(cyclopentylcarbamoyl)amino]-1,3-benzothiazol-6-yl 2,6-dichlorobenzene-sulfonate | 35 mg | 249° C. |
| 74 | 2-[(isopropylcarbamoyl)amino]-1,3-benzothiazol-6-yl 2,6-dichlorobenzene-sulfonate | 57 mg | 169° C. |
| 75 | 2-[(cyclobutylcarbamoyl)amino]-1,3-benzothiazol-6-yl 2,6-dichlorobenzene-sulfonate | 20 mg | Rf TLC silica = 0.32 [eluent: dichloro-methane/ methanol (90/10) by volume)] |
| 76 | 2-{[(2-azepan-1-ylethyl)carbamoyl]-amino}-1,3-benzothiazol-6-yl 2,6-di-chlorobenzenesulfonate | 60 mg | 146° C. |
| 77 | 2-[(dimethylcarbamoyl)amino]-1,3-benzothiazol-6-yl 2,6-dichlorobenzene-sulfonate | 15 mg | Rf TLC silica = 0.36 [eluent: dichloro-methane/ methanol (95/5) by volume)] |
| 78 | 2-{[(pyridin-3-ylmethyl)carbamoyl]-amino}-1,3-benzothiazol-6-yl 2,6-di-chlorobenzenesulfonate | 60 mg | 227° C. |
| 79 | 2-({[2-(4-benzylpiperazin-1-yl)-2-oxo-ethyl]carbamoyl}amino)-1,3-benzothiazol-6-yl 2,6-dichlorobenzene-sulfonate | 7 mg | Rf TLC silica = 0.27 [eluent: dichloro-methane/ methanol (95/5) by volume)] | b) 2-[(Phenoxycarbonyl)amino]-1,3-benzothiazol-6-yl 2,6-dichlorobenzenesulfonate may be prepared in the following manner:

A solution of 2 g of 2-amino-1,3-benzothiazol-6-yl 2,6-dichlorobenzenesulfonate, 3.34 g of phenyl chloroformate, 1.79 g of sodium hydrogen carbonate in 40 cm³ of tetrahydrofuran and 4 cm³ of water is stirred for about 60 hours at a temperature in the region of 20° C. After concentrating the reaction mixture to dryness, the residue is taken up in 20 cm³ of water. The solid is filtered off by suction and washed with twice 5 cm³ of water, and then dried in an oven at 50° C. 2.5 g of 2-[(phenoxycarbonyl)amino]-1,3-benzothiazol-6-yl 2,6-dichlorobenzenesulfonate are thus obtained in the form of a brown solid, the characteristics of which are as follows:

Rf TLC silica=0.77 [eluent: dichloromethane/methanol (95/5 by volume)]

Mass spectrum: 495 [MH+] (2 Cl present)

The NMR results obtained for the products of Examples 52 to 79 are indicated as follows:

Example 52

¹H NMR spectrum at 500 MHz: 2.20 (s, 3H); 2.42 (m, 4H); 3.09 (m, 4H); 4.24 (d, J=6.0 Hz, 2H); 6.90 (d, J=9.0 Hz, 2H); 7.02 (dd, J=2.5 and 9.0 Hz, 1H); 7.10 (broad m, 1H); 7.15 (d, J=9.0 Hz, 2H); 7.56 (d, J=9.0 Hz, 1H); from 7.71 to 7.81 (m, 4H); 10.9 (broad m, 1H).

Example 53

¹H NMR spectrum at 500 MHz: 1.61 (m, 2H); 2.29 (t, J=6.5 Hz, 2H); 2.33 (m, 4H); 3.18 (q, J=6.5 Hz, 2H); 3.57 (m, 4H); 6.77 (broad m, 1H); 7.02 (dd, J=2.5 and 9.0 Hz, 1H); 7.56 (d, J=9.0 Hz, 1H); from 7.71 to 7.81 (m, 4H); 10.9 (broad s, 1H).

Example 54

¹H NMR spectrum at 500 MHz: 1.70 (m, 2H); 2.52 (partially masked m, 2H); 2.86 (s, 3H); 3.19 (q, J=6.5 Hz, 2H); 6.58 (t, J=7.5 Hz, 1H); 6.69 (d, J=7.5 Hz, 2H); 6.81 (broad m, 1H); 7.03 (dd, J=2.5 and 9.0 Hz, 1H); 7.15 (t, J=7.5 Hz, 2H); 7.57 (d, J=9.0 Hz, 1H); from 7.71 to 7.82 (m, 4H); 10.85 (broad, 1H)

Example 55

¹H NMR spectrum at 500 MHz: For this lot, all signals are broad: 1.20 (m, 2H); 1.48 (m, 1H); 1.53 (m, 2H); 1.85 (m, 2H); 2.36 (m, 2H); 2.52 (partially masked m, 2H); 2.84 (m, 2H); 3.22 (q, J=6.5 Hz, 2H); 6.67 (broad m, 1H); 6.99 (broad m, 1H); 7.16 (m, 3H); 7.27 (t, J=7.5 Hz, 2H); 7.51 (broad m, 1H); from 7.69 to 7.80 (m, 4H); 10.95 (broad m, 1H).

Example 56

¹H NMR spectrum at 500 MHz: 1.71 (m, 4H); 2.51 (partially masked m, 6H); 3.30 (partially masked m, 2H); 6.82 (broad m, 1H); 7.02 (dd, J=2.5 and 9.0 Hz, 1H); 7.57 (d, J=9.0 Hz, 1H); from 7.71 to 7.79 (m, 3H); 7.81 (d, J=2.5 Hz, 1H); 10.85 (broad m, 1H).

Example 57

¹H NMR spectrum at 500 MHz: From 1.55 to 2.17 (m, 8H); from 2.38 to 2.68 (partially masked m, 4H); from 2.86 to 3.01 (m, 3H); 3.69 (m, 1H); 3.98 (m, 1H); 6.97 (broad d, J=9.0 Hz, 1H); 7.46 (d, J=9.0 Hz, 1H); from 7.70 to 7.79 (m, 4H).

Example 58

¹H NMR spectrum at 500 MHz: From 1.53 to 2.16 (m, 8H); from 2.40 to 2.70 (partially masked m, 4H); from 2.85 to 3.04 (m, 3H); 3.66 (m, 1H); 3.98 (m, 1H); 6.97 (broad d, J=9.0 Hz, 1H); 7.46 (d, J=9.0 Hz, 1H); from 7.70 to 7.79 (m, 4H).

Example 59

¹H NMR spectrum at 400 MHz: 1.62 (m, 2H); 1.68 (m, 4H); 2.42 (m, 6H); 3.20 (q, J=6.5 Hz, 2H); 6.77 (broad m, 1H); 7.03 (dd, J=2.5 and 9.0 Hz, 1H); 7.56 (d, J=9.0 Hz, 1H); from 7.70 to 7.79 (m, 4H); 10.8 (broad m, 1H).

Example 60

¹H NMR spectrum at 400 MHz: 2.15 (s, 3H); from 2.25 to 2.54 (partially masked m, 10H); 3.24 (partially masked m, 2H); 6.72 (broad m, 1H); 7.02 (dd, J=2.5 and 9.0 Hz, 1H); 7.55 (d, J=9.0 Hz, 1H); from 7.70 to 7.79 (m, 4H); 11.0 (broad m, 1H).

Example 61

¹H NMR spectrum at 400 MHz: 1.42 (m, 2H); 1.61 (m, 2H); 1.75 (m, 1H); 1.88 (m, 1H); 2.04 (m, 2H); 2.20 (s, 3H); 2.95 (m, 1H); 3.18 (q, J=6.5 Hz, 2H); 6.80 (broad, 1H); 7.02 (dd, J=2.5 and 9.0 Hz, 1H); 7.54 (d, J=9.0 Hz, 1H); from 7.69 to 7.80 (m, 4H); 10.85 (broad m, 1H).

Example 62

¹H NMR spectrum at 400 MHz: 1.59 (m, 2H); 2.13 (s, 6H); 2.24 (t, J=6.5 Hz, 2H); 3.18 (q, J=6.5 Hz, 2H); 6.84 (broad m, 1H); 7.03 (dd, J=2.5 and 9.0 Hz, 1H); 7.56 (d, J=9.0 Hz, 1H); from 7.69 to 7.80 (m, 4H); 10.85 (broad m, 1H).

Example 63

¹H NMR spectrum at 400 MHz: 1.08 (d, J=6.5 Hz, 6H); 1.12 (m, 2H); 1.26 (m, 1H); 1.50 (m, 2H); 1.58 (m, 1H); 2.45 (m, 2H); 2.64 (t, J=6.5 Hz, 2H); 3.15 (q, J=6.5 Hz, 2H); 6.73 (broad, 1H); 7.03 (dd, J=2.5 and 9.0 Hz, 1H); 7.56 (d, J=9.0 Hz, 1H); from 7.69 to 7.79 (m, 4H); 10.95 (broad m, 1H).

Example 64

¹H NMR spectrum at 400 MHz: 1.39 (m, 2H); 1.51 (m, 4H); 2.36 (m, 6H); 3.25 (q, J=6.5 Hz, 2H); 6.73 (broad m, 1H); 7.02 (dd, J=2.5 and 9.0 Hz, 1H); 7.57 (d, J=9.0 Hz, 1H); from 7.71 to 7.82 (m, 4H); 10.95 (broad m, 1H).

Example 65

¹H NMR spectrum at 500 MHz: 1.63 (m, 2H); 1.91 (m, 2H); 2.22 (t, J=6.5 Hz, 2H); 2.52 (partially masked m, 2H); 3.11 (q, J=6.5 Hz, 2H); 3.20 (t, J=6.5 Hz, 2H); 6.79 (broad m, 1H); 7.02 (dd, J=2.5 and 9.0 Hz, 1H); 7.56 (d, J=9.0 Hz, 1H); from 7.71 to 7.80 (m, 4H); 10.95 (broad m, 1H).

Example 66

¹H NMR spectrum at 500 MHz: 2.86 (s, 6H); 4.22 (d, J=6.0 Hz, 2H); 6.69 (d, J=9.0 Hz, 2H); 7.00 (broad d, J=9.0 Hz, 1H), 7.04 (broad m, 1H); 7.13 (d, J=9.0 Hz, 2H); 7.52 (broad d, J=9.0 Hz, 1H); from 7.70 to 7.80 (m, 4H); 10.85 (broad, 1H).

Example 67

¹H NMR spectrum at 500 MHz: 1.58 (m, 2H); from 2.19 to 2.56 (partially masked broad m, 8H); 2.26 (t, J=6, Hz, 2H); 3.15 (q, J=6.5 Hz, 2H); 3.57 (s, 2H); 6.75 (broad m, 1H); 7.01 (broad dd J=2.5 and 9.0 Hz, 1H), 7.21 (t, J=8.5 Hz, 1H); 7.32 (broad d, J=8.5 Hz, 1H); 7.3 (m, 1H); 7.53 (broad d, J=9.0 Hz, 1H); from 7.70 a 7.79 (m, 4H); 10.85 (broad m 1H).

Example 68

¹H NMR spectrum at 500 MHz: 1.58 (m, 2H); from 2.19 to 2.55 (partially masked broad m, 8H); 2.29 (t, J=6, Hz, 2H);

3.17 (q, J=6.5 Hz, 2H); 3.44 (s, 2H); 6.72 (broad m, 1H); 7.02 (dd, J=2.5 and 9.0 Hz, 1H), from 7.21 to 7.36 (m, 5H); 7.57 (broad d, J=9.0 Hz 1H); from 7.7 to 7.82 (m, 4H); 10.8 (broad m, 1H).

Example 69

$^1$H NMR spectrum at 500 MHz: 1.60 (m, 2H); from 2.05 to 2.70 (partially masked broad m, 8H); 2.13 (s, 3H); 2.28 (t, J=6.5 Hz, 2H); 3.16 (q, J=6.5 Hz, 2H); 6.75 (broad m, 1H); 7.02 (dd, J=2.5 and 9.0 Hz, 1H), 7.55 (d, J=9.0 Hz, 1H); from 7.70 to 7.81 (m, 4H); 10.9 (broad m, 1H).

Example 70

$^1$H NMR spectrum at 500 MHz: 3.06 (m, 4H); 3.72 (m, 4H); 4.25 (d, J=6.0 Hz, 2H); 6.91 (d, J=9.0 Hz, 2H); 6.98 (broad d, J=9.0 Hz, 1H); 7.11 (broad m, 1H); 7.17 (d, J=9.0 Hz, 2H); 7.50 (broad m, 1H); from 7.70 to 7.79 (m, 4H); 10.9 (broad m, 1H).

Example 71

$^1$H NMR spectrum at 500 MHz: 2.71 (d, J=5.0 Hz, 3H); 6.62 (broad m, 1H); 7.02 (dd, J=2.5 and 9.0 Hz, 1H); 7.56 (d, J=9.0 Hz, 1H); from 7.71 to 7.81 (m, 4H); 10.95 (broad m, 1H).

Example 72

$^1$H NMR spectrum at 500 MHz: From 1.36 to 1.65 (m, 10H); 1.83 (m, 2H); 3.72 (m, 1H); 6.74 (broad doublet, J=8.0 Hz, 1H); 7.01 (dd, J=2.5 and 9.0 Hz, 1H); 7.56 (d, J=9.0 Hz, 1H); from 7.71 to 7.81 (m, 4H); 10.6 (broad m, 1H).

Example 73

$^1$H NMR spectrum at 500 MHz: 1.40 (m, 2H); 1.55 (m, 2H); 1.64 (m, 2H); 1.87 (m, 2H); 3.98 (m, 1H); 6.76 (broad d, J=6.5 Hz, 1H); 7.02 (dd, J=2.5 and 9.0 Hz, 1H); 7.57 (d, J=9.0 Hz, 1H); from 7.71 to 7.82 (m, 4H); 10.5 (broad m, 1H).

Example 74

$^1$H NMR spectrum at 500 MHz: 1.13 (d, J=6.5 Hz, 6H); 3.81 (m, 1H); 6.81 (broad d, J=7.0 Hz, 1H); 7.02 (dd, J=2.5 and 9.0 Hz, 1H); 7.56 (d, J=9.0 Hz, 1H); from 7.70 to 7.81 (m, 4H); 10.5 (broad m, 1H).

Example 75

$^1$H NMR spectrum at 500 MHz: 1.62 (m, 2H); 1.91 (m, 2H); 2.21 (m, 2H); 4.16 (m, 1H); 6.98 (broad m, 1H); 7.01 (dd, J=2.5 and 9.0 Hz, 1H); 7.55 (d, J=9.0 Hz, 1H); from 7.70 to 7.80 (m, 4H); 10.7 (broad m, 1H).

Example 76

$^1$H NMR spectrum at 500 MHz: From 1.50 to 1.68 (m, 8H); from 2.46 to 2.69 (partially masked broad m, 6H); 3.22 (broad m, 2H); 6.70 (broad m, 1H); 7.03 (dd, J=2.5 and 9.0 Hz, 1H); 7.57 (d, J=9.0 Hz, 1H); from 7.71 to 7.79 (m, 3H); 7.81 (broad s, 1H); 11.05 (broad m, 1H).

Example 77

$^1$H NMR spectrum at 500 MHz: 2.98 (s, 6H); 7.04 (dd, J=2.5 and 9.0 Hz, 1H); 7.53 (broad m, 1H); from 7.70 to 7.81 (m, 4H); 11.25 (broad m, 1H).

Example 78

$^1$H NMR spectrum at 500 MHz: 4.40 (d, J=6.5 Hz, 2H); 7.03 (dd, J=2.5 and 9.0 Hz, 1H); 7.35 (masked broad m, 1H); 7.36 (dd, J=5.0 and 8.0 Hz, 1H); 7.56 (d, J=9.0 Hz, 1H); from 7.70 to 7.79 (m, 5H); 8.46 (dd, J=1.5 and 5.0 Hz, 1H); 8.53 (broad d, J=2.5 Hz, 1H); 11.0 (broad m, 1H).

Example 79

$^1$H NMR spectrum at 500 MHz: From 2.31 to 2.43 (m, 4H); 3.36 to 3.52 (m, 6H); 4.05 (d, J=5.0 Hz, 2H); 6.88 (broad m, 1H); 6.99 (broad d, J=9.0 Hz, 1H); 7.26 (m, 1H); 7.33 (m, 4H); 7.52 (broad m, 1H); from 7.69 to 7.79 (m, 4H); 11.1 (broad m, 1H).

Pharmacological Section:

Experimental Protocols

A) HTRF Met Test in 96-Well Format c-MET 5 nM final is incubated in a final volume of 50 µl of enzymatic reaction in the presence of the test molecule (for a final concentration range of from 0.17 nM to 10 µM, 3% DMSO final) in 10 mM pH 7.4 MOPS buffer, 1 mM DTT, 0.01% Tween 20. The reaction is initiated with the substrate solution to obtain final concentrations of 1 µg/ml poly-(GAT), 10 µM ATP and 5 mM $MgCl_2$. After incubating for 10 minutes at room temperature, the reaction is stopped with a 30 µl mix to obtain a final solution of 50 mM pH 7.5 Hepes, 500 mM potassium fluoride, 0.1% BSA and 133 mM EDTA in the presence of 80 ng of Streptavidin 61SAXLB Cis-Bio Int. and 18 ng anti-Phosphotyrosine Mab PT66-Europium Cryptate per well. After incubating for 2 hours at room temperature, the reading is taken at 2 wavelengths: 620 nm and 665 nm, on a reader for the TRACE/HTRF technique and the % inhibition is calculated from the 665/620 ratios.

B) Inhibition of the Autophosphorylation of MET; ELISA Technique (pppY1230, 1234, 1235)

a) Cell lysates: Inoculate MKN45 cells into a 96-well plate (Cell coat BD polylysine) at 20 000 cells/well at 200 µl in RPMI medium+10% FCS+1% L-glutamine. Leave to adhere for 24 hours in an incubator. The cells are treated the day after inoculation with the products at 6 concentrations in duplicate for 1 hour. At least 3 control wells are treated with the same amount of final DMSO.

Product dilution: Store at 10 mM in pure DMSO—range from 10 mM to 30 µM with an increment of 3 as pure DMSO—intermediate 1/50 dilutions in the culture medium and then removal of 10 µl added directly to the cells (200 µl): final range from 10 000 to 30 nM.

At the end of the incubation, remove the supernatant carefully and rinse with 200 µl of PBS. Next, place 100 µl of lysis buffer directly in the wells over ice and incubate at 4° C. for 30 minutes. Lysis buffer: 10 mM Tris HCl, pH 7.4, 100 mM NaCl, 1 mM EDTA, 1 mM EGTA, 1% Triton X-100, 10% glycerol, 0.1% SDS, 0.5% deoxycholate, 20 mM NaF, 2 mM $Na_3VO_4$, 1 mM PMSF and antiproteases cocktail.

The 100 µl of lysates are transferred into a V-bottomed polypropylene plate and the ELISA is performed immediately, or the plate is frozen at −80° C.

b) PhosphoMET ELISA BioSource Kit KHO0281

Into each well of the kit plate, add 70 μl of kit dilution buffer+30 μL of cell lysate or 30 μl of lysis buffer for the blanks. Incubate for 2 hours with gentle stirring at room temperature.

Rinse the wells 4 times with 400 μl of kit washing buffer. Incubate with 100 μl of antiphospho MET antibody for 1 hour at room temperature.

Rinse the wells 4 times with 400 μl of kit washing buffer. Incubate with 100 μl of anti-rabbit HRP antibody for 30 minutes at room temperature (except for the wells of chromogen alone).

Rinse the wells 4 times with 400 μl of kit washing buffer. Introduce 100 μL of chromogen and incubate for 30 minutes in darkness at room temeprature.

Stop the reaction with 100 μl of stop solution. Read without delay at 450 nM 0.1 second on a Wallac Victor plate reader.

c) Measurement of the cell proliferation by 14C-thymidine pulse

The cells are inoculated into 96-well Cytostar plates in 180 μl for 4 hours at 37° C. and 5% $CO_2$: HCT116 cells at a rate of 2500 cells per well in DMEM medium+10% foetal calf serum+1% L-glutamine and the MKN45 cells at a rate of 7500 cells per well in RPMI medium+10% foetal calf serum+1% L-glutamine. After these 4 hours of incubation, the products are added in 10 μl as a 20-fold concentrated solution according to the dilution method cited for the ELISA. The products are tested at 10 concentrations in duplicate from 10 000 nM to 0.3 nM with an increment of 3.

After treatment for 72 hours, add 10 μl of 14C-thymidine at 10 μCi/ml to obtain 0.1 μCi per well. The incorporation of 14C-thymidine is measured on a Micro-Beta machine (Perkin-Elmer) after 24 hours of pulse and 96 hours of treatment.

All the steps of the test are automated on BIOMEK 2000 or TECAN stations.

What is claimed is:

1. A compound of formula (I)

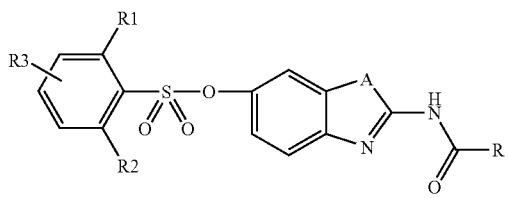

wherein:
A represents NH or S;
R1 and R2, which may be identical or different, are chosen from a hydrogen atom, halogen atoms, and alkyl radicals optionally substituted with one or more halogen atoms;
R3 represents a hydrogen atom or is chosen from the values of R1 and R2;
it being understood that at least one from among R1, R2 and R3 does not represent hydrogen;
R is NR4R5 in which R4 and R5 are such that one from among R4 and R5 is hydrogen or alkyl and the other from among R4 and R5 is alkyl substituted with one or more groups, which may be identical or different, chosen from hydroxyl, alkoxy and NR6R7, with R6 and R7, which may be identical or different, representing hydrogen or alkyl, or alternatively R6 and R7 form, with the nitrogen atom to which they are attached, a nitrogen containing heterocyclic optionally containing one or more other heteroatoms chosen from 0, S, N and NH, this heterocyclic, including the possible NH it contains, being optionally substituted; and
all the alkyl and alkoxy groups of R containing from 1 to 4 carbon atoms;
said heterocyclic which R6 and R7 may form with the nitrogen atom to which they are attached being optionally substituted with one or more radicals chosen from halogen atoms, hydroxyl, oxo, alkoxy, $NH_2$; NHalk, N(alk)$_2$ radicals and alkyl, $CH_2$-heterocycloalkyl, $CH_2$-phenyl and CO-phenyl radicals, such that in these latter radicals the alkyl, heterocycloalkyl and phenyl radicals are themselves optionally substituted with one or more radicals chosen from halogen atoms and hydroxyl, oxo, alkyl and alkoxy containing from 1 to 4 carbon atoms, $NH_2$; NHalk and N(alk)$_2$ radicals, and all the alkyl and alkoxy radicals of R1, R2 and R3 containing from 1 to 6 carbon atoms; or an inorganic or organic acid addition salt thereof, or an inorganic or organic base addition salt thereof.

2. The compound according to claim 1 wherein:
R1 and R2, which may be identical or different, are chosen from fluorine and chlorine atoms and alkyl radicals; and R3 represents a hydrogen atom or an alkyl radical optionally substituted with one or more fluorine atoms; and
all the alkyl and alkoxy radicals containing from 1 to 4 carbon atoms;
or an inorganic or organic acid addition salt thereof, or an inorganic or organic base addition salt thereof.

3. The compound according to claim 1 wherein:
R1 and R2, which may be identical or different, are chosen from fluorine and chlorine atoms and a methyl radical; and R3 represents a hydrogen atom, a methyl radical or $CF_3$; and
all the alkyl and alkoxy radicals containing from 1 to 4 carbon atoms;
or an inorganic or organic acid addition salt thereof, or an inorganic or organic base addition salt thereof.

4. The compound according to claim 1 wherein:
R is NHalkyl with alkyl containing 1 or 2 carbon atoms substituted with an alkoxy or morpholino radical;
or an inorganic or organic acid addition salt thereof, or an inorganic or organic base addition salt thereof.

5. The compound according to claim 1 wherein:
A represents NH;
or an inorganic or organic acid addition salt thereof, or an inorganic or organic base addition salt thereof.

6. The compound according to claim 1 wherein:
A represents S; or
or an inorganic or organic acid addition salt thereof, or an inorganic or organic base addition salt thereof.

7. The compound according to claim 1 which is:
2-({[2-(4-benzylpiperazin-1-yl)ethyl]carbamoyl}amino)-1,3-benzothiazol-6-yl-2,6-dichlorobenzenesulfonate;
2-{[(3-morpholin-4-ylpropyl)carbamoyl]amino}-1,3-benzothiazol-6-yl-2,6-dichlorobenzenesulfonate;
2-{[(2-pyrrolidin-1-ylethyl)carbamoyl]amino}-1,3-benzothiazol-6-yl-2,6-dichlorobenzenesulfonate;
2-{[(3-pyrrolidin-1-ylpropyl)carbamoyl]amino}-1,3-benzothiazol-6-yl-2,6-dichlorobenzenesulfonate;
2-({[2-(4-methylpiperazin-1-yl)ethyl]carbamoyl}amino)-1,3-benzothiazol-6-yl 2,6-dichlorobenzenesulfonate;
2-({[2-(1-methylpyrrolidin-2-yl)ethyl]carbamoyl}amino)-1,3-benzothiazol-6-yl-2,6-dichlorobenzenesulfonate;

2-({[3-(dimethylamino)propyl]carbamoyl}amino)-1,3-benzothiazol-6-yl 2,6-dichlorobenzenesulfonate;
2-({[2-(2,6-dimethylpiperidin-1-yl)ethyl]carbamoyl}amino)-1,3-benzothiazol-6-yl 2,6-dichlorobenzenesulfonate;
2-{[(2-piperidin-1-ylethyl)carbamoyl]amino}-1,3-benzothiazol-6-yl 2,6-dichlorobenzenesulfonate;
2-({[3-(2-oxopyrrolidin-1-yl)propyl]carbamoyl}amino)-1,3-benzothiazol-6-yl 2,6-dichlorobenzenesulfonate;
2-({[3-(4-benzylpiperazin-1-yl)propyl]carbamoyl}amino)-1,3-benzothiazol-6-yl 2,6-dichlorobenzenesulfonate;
2-({[3-(4-methylpiperazin-1-yl)propyl]carbamoyl}amino)-1,3-benzothiazol-6-yl 2,6-dichlorobenzenesulfonate; or
2-{[(2-azepan-1-ylethyl)carbamoyl]amino}-1,3-benzothiazol-6-yl 2,6-dichlorobenzenesulfonate; or
an inorganic or organic acid addition salt, or an inorganic or organic base addition salt thereof.

8. The compound according to claim 1 which is:
2-[3-(2-methoxyethyl)ureido]-1H-benzimidazol-5-yl 2,6-dichloro-benzenesulfonate;
2-[3-(2-methoxyethyl)ureido]-1H-benzimidazol-5-yl 2-chloro-6-methyl-benzenesulfonate;
2-[3-(2-methoxyethyl)ureido]-1H-benzimidazol-5-yl 2,4,6-trimethylbenzenesulfonate;
2-[3-(2-methoxyethyl)ureido]-1H-benzimidazol-5-yl 2,6-dichloro-4-trifluoromethylbenzenesulfonate;
2-[3-(2-morpholin-4-yl-ethyl)ureido]-1H-benzimidazol-5-yl 2,6-dichlorobenzenesulfonate;
2-[3-(2-morpholin-4-yl-ethyl)ureido]-benzothiazol-6-yl 2,6-dichlorobenzenesulfonate;
2-[3-(2-morpholin-4-yl-ethyl)ureido]-benzothiazol-6-yl 2,6-difluorobenzenesulfonate; or
2-[3-(2-methoxyethyl)ureido]-benzothiazol-6-yl 2,6-difluorobenzenesulfonate; or
an inorganic or organic acid addition salt, or an inorganic or organic base addition salt thereof.

9. The compound according to claim 1 which is:
2-{[(2-methoxyethyl)carbamoyl]amino}-1H-benzimidazol-5-yl 2,6-dichlorobenzenesulfonate;
2-{[(2-methoxyethyl)carbamoyl]amino}-1H-benzimidazol-5-yl 2-chloro-6-methylbenzenesulfonate;
2-{[(2-methoxyethyl)carbamoyl]amino}-1H-benzimidazol-5-yl 2,6-dichloro-4-(trifluoromethyl)benzenesulfonate;
2-{[(2-morpholin-4-ylethyl)carbamoyl]amino}-1H-benzimidazol-5-yl 2,6-dichlorobenzenesulfonate;
2-{[(2-morpholin-4-ylethyl)carbamoyl]amino}-1,3-benzothiazol-6-yl-2,6-dichlorobenzenesulfonate;
2-({[2-(4-benzylpiperazin-1-yl)ethyl]carbamoyl}amino)-1,3-benzothiazol-6-yl 2,6-dichlorobenzenesulfonate;
2-{[(3-morpholin-4-ylpropyl)carbamoyl]amino}-1,3-benzothiazol-6-yl 2,6-dichlorobenzenesulfonate;
2-{[(3-pyrrolidin-1-ylpropyl)carbamoyl]amino}-1,3-benzothiazol-6-yl 2,6-dichlorobenzenesulfonate;
2-({[2-(4-methylpiperazin-1-yl)ethyl]carbamoyl}amino)-1,3-benzothiazol-6-yl 2,6-dichlorobenzenesulfonate;
2-({[3-(dimethylamino)propyl]carbamoyl}amino)-1,3-benzothiazol-6-yl 2,6-dichlorobenzenesulfonate; or
2-{[(2-azepan-1-ylethyl)carbamoyl]amino}-1,3-benzothiazol-6y; 2,6-dichlorobenzenesulfonate; or
an inorganic or organic acid addition salt, or an inorganic or organic base addition salt thereof.

10. The compound according to claim 1 which is:
2-{[(2-methoxyethyl)carbamoyl]amino}-1H-benzimidazol-5-yl 2,6-dichlorobenzenesulfonate;
2-{[(2-methoxyethyl)carbamoyl]amino}-1H-benzimidazol-5-yl 2-chloro-6-methylbenzenesulfonate;
2-{[(2-methoxyethyl)carbamoyl]amino}-1H-benzimidazol-5-yl 2,6-dichloro-4-(trifluoromethyl)benzenesulfonate;
2-{[(2-morpholin-4-ylethyl)carbamoyl]amino}-1H-benzimidazol-5-yl-2,6-dichlorobenzenesulfonate;
2-({[2-(4-benzylpiperazin-1-yl)ethyl]carbamoyl}amino)-1,3-benzothiazol-6-yl 2,6-dichlorobenzenesulfonate;
2-{[(3-morpholin-4-ylpropyl)carbamoyl]amino}-1,3-benzothiazol-6-yl-2,6-dichlorobenzenesulfonate;
2-{[(3-pyrrolidin-1-ylpropyl)carbamoyl]amino}-1,3-benzothiazol-6-yl-2,6-dichlorobenzenesulfonate;
2-({[2-(4-methylpiperazin-1-yl)ethyl]carbamoyl}amino)-1,3-benzothiazol-6-yl-2,6-dichlorobenzenesulfonate;
or
2-({[3-(dimethylamino)propyl]carbamoyl}amino)-1,3-benzothiazol-6-yl 2,6-dichlorobenzenesulfonate; or
an inorganic or organic acid addition salt, or an inorganic or organic base addition salt thereof.

11. The compound according to claim 1 which is:
2-[3(2-morpholin-4-yl-ethyl)-ureido]-benzothiazol-6-yl-2,6-dichloro-benzenesulfonate;
2-({[2-(4-benzylpiperazin-1-yl)ethyl]carbamoyl}amino)-1,3-benzothiazol-6-yl-2,6-dichlorobenzenesulfonate;
2-{[(3-morpholin-4-ylpropyl)carbamoyl]amino}-1,3-benzothiazol-6-yl-2,6-dichlorobenzenesulfonate; or
2-{[(3-pyrrolidin-1-ylpropyl)carbamoyl]amino}-1,3-benzothiazol-6-yl-2,6-dichlorobenzenesulfonate;
or an inorganic or organic acid addition salt thereof, or an inorganic or organic base addition salt thereof.

12. A process for preparing a compound according to claim 1, wherein a compound of formula (A):

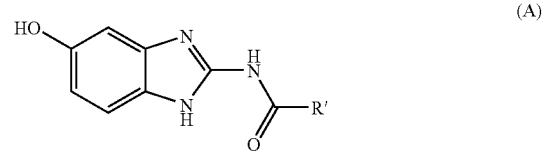

(A)

in which R' has the meaning indicated in claim 1 for R in which the potentially reactive functions are optionally protected,
is reacted with a compound of formula (B):

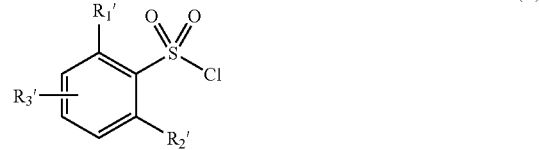

(B)

in which R1', R2' and R3' have the meanings indicated in claim 1, respectively, for R1, R2 and
R3 in which the potentially reactive functions are optionally protected, to obtain a product of formula (Ia):

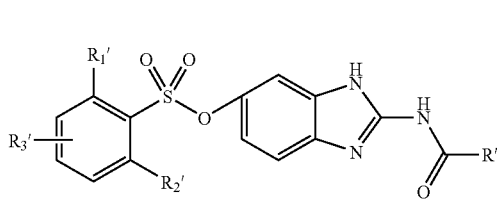

in which R1', R2', R3' and R' have the meanings given above,
which products of formula (Ia) thus obtained are products of formula (I) in which A represents NH and which, in order to obtain products or other products of formula (I), are subjected, to one or more of the following conversion reactions, in any order:
a) an esterification reaction of an acid function,
b) a saponification reaction of an ester function to an acid function,
c) a reduction reaction of the free or esterified carboxyl function to an alcohol function,
d) a conversion reaction of an alkoxy function to a hydroxyl function, or alternatively of a hydroxyl function to an alkoxy function,
e) a reaction for removal of the protecting groups that the protected reactive functions may bear,
f) a salification reaction with a mineral or organic acid or with a base to obtain the corresponding salt,
g) a reaction for resolution of racemic forms as resolved products, the said products of formula (I) thus obtained being in any possible racemic, enantiomeric or diastereoisomeric isomer form.

13. A process for preparing a compound according to claim 1 wherein the compound of formula (D):

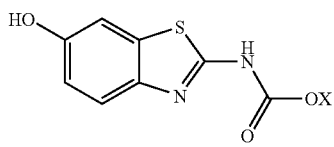

in which COOX represents an NH$_2$ protecting group, is reacted with an amine of formula (G):

 (G)

in which R4' and R5' have the meanings indicated in claim 1 for R4 and R5 in which the potentially reactive functions are optionally protected,
to obtain a compound of formula (F):

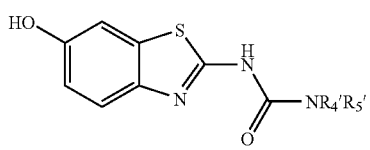

in which R4' and R5' have the meanings given above, which compound of formula F is reacted with a compound of formula (B):

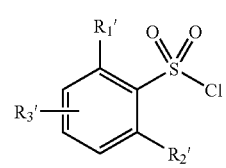

in which R1', R2' and R3' have the meanings indicated in claim 1, respectively, for R1, R2 and R3 in which the potentially reactive functions are optionally protected,
to obtain a product of formula (Ib):

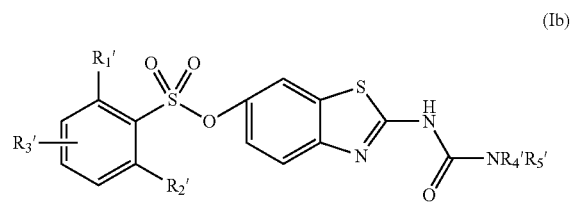

in which R1', R2', R3', R4' and R5' have the meanings given above,
which products of formula (Ib) thus obtained are products of formula (I) in which A represents S and which, in order to obtain products or other products of formula (I), are subjected, to one or more of the following conversion reactions, in any order:
a) an esterification reaction of an acid function,
b) a saponification reaction of an ester function to an acid function,
c) a reduction reaction of the free or esterified carboxyl function to an alcohol function,
d) a conversion reaction of an alkoxy function to a hydroxyl function, or alternatively of a hydroxyl function to an alkoxy function,
e) a reaction for removal of the protecting groups that the protected reactive functions may bear,
f) a salification reaction with a mineral or organic acid or with a base to obtain the corresponding salt,
g) a reaction for resolution of racemic forms as resolved products,
the said products of formula (I) thus obtained being in any possible racemic, enantiomeric or diastereoisomeric isomer form.

14. A pharmaceutical composition comprising a pharmaceutically effective amount of a compound according to claim 1 or an inorganic or organic acid addition salt, or an inorganic or organic base addition salt thereof, and a pharmaceutically acceptable excipient.

15. A method of inhibiting the activity of a protein kinase, in a patient in need thereof, comprising administering to such a patient a pharmaceutically effective amount of a compound according to claim 1.

* * * * *